United States Patent [19]
Ohno et al.

[11] Patent Number: 5,807,673
[45] Date of Patent: Sep. 15, 1998

[54] PROBE FOR DIAGNOSING INFECTIOUS DISEASE

[75] Inventors: Tsuneya Ohno, 16-15, Kita-Aoyama 3 chome, Minato-ku, Tokyo 107; Akio Matsuhisa, Nara; Hirotsugu Uehara, Kobe; Soji Eda, Osaka, all of Japan

[73] Assignees: Tsuneya Ohno, Tokyo; Fuso Pharmaceutical Industries, Ltd., Osaka, both of Japan

[21] Appl. No.: 362,577

[22] PCT Filed: Jul. 7, 1993

[86] PCT No.: PCT/JP93/00936
§ 371 Date: Mar. 27, 1995
§ 102(e) Date: Mar. 27, 1995

[87] PCT Pub. No.: WO94/01583
PCT Pub. Date: Jan. 20, 1994

[30] Foreign Application Priority Data

Jul. 7, 1992 [JP] Japan ................................. 4-179719

[51] Int. Cl.[6] .............................. C12Q 1/68; C07H 21/04
[52] U.S. Cl. .......................... 435/6; 536/24.32; 536/23.7; 536/24.33; 935/6; 935/8; 935/9; 935/78
[58] Field of Search .............................. 435/6; 536/24.32, 536/24.33, 23.7; 935/6, 8, 9, 78

[56] References Cited

PUBLICATIONS

Alberts et al., *Molecular Biology of the Cell*, Second Edition, Garland Publishing Inc., New York, NY, pp. 182 and 188–193 (1989).

Cano et al., *Microbiology*, West Publishing Company, Minneapolis, MN, pp. 264–268, 279, 293, 296, 297, and 801 (1986).

Lehninger, A.L., *Principles of Biochemistry*, Worth Publishers, Inc., New York, pp. 809–811 (1982).

Maniatis et al., *Molecular Cloning: A Laboratory Manual*, Cold Spring Harbor Laboratory, Cold Spring Harbor, NY, pp. 309–330, 374 and 375 (1982).

Sambrook et al., *Molecular Cloning: A Laboratory Manual*, Second Edition, Cold Spring Harbor Laboratory Press, Cold Spring Harbor, NY, pp. 5.10, 5.11, and 12.21–12.23 (1989).

Smith et al., *Principles of Biochemistry: General Aspects*, Seventh Edition, McGraw–Hill Book Company, New York, NY, p. 723 (1983).

Watson et al., *Molecular Biology of the Gene*, Fourth Edition, The Benjamin/Cummings Publishing Company, Inc., Menlo Park, CA, pp. 89, 208–210, and 608 (1987).

Watson et al., *Recombinant DNA: A Short Course*, Scientific American Books, USA, pp. 58–60 (1983).

Gerberding et al. Antimicrobial and Chemotherapy. 35(12): 2574–2579 Dec. 1991.

*Primary Examiner*—Carla J. Myers
*Attorney, Agent, or Firm*—Marshall, O'Toole, Gerstein, Murray & Borun

[57] ABSTRACT

DNA probes for diagnosing infectious diseases involving *Staphylococcus aureus* and methods of using such probes are provided.

2 Claims, 6 Drawing Sheets

//PROBE FOR DIAGNOSING INFECTIOUS DISEASE

TECHNICAL FIELD

The present invention relates to probes, prepared by making use of causative bacteria of infectious diseases, which are useful for detecting and identifying the causative bacteria.

BACKGROUND ART

In pathology, infection is defined as invasion and establishment of a foothold for growth in an organism by a pathogenic organism (hereinafter referred to as "bacteria"), then the outbreak of disease depends upon the interrelationship between the resistance of host and the virulence of bacteria.

In the infectious diseases, improvement in treatment methods of bateremia have been raised as an important issue. That is to say, bacteremia is not a disease caused by a particular bacterium, but is caused by emergence and habitancy of the various bacteria in blood, then onset thereof is clinically suspected when fever of about 40° C. persists for two or more days. If a patient is an infant or is suffering from terminal cancer with weakened resistance, the patient may die in one or two days, therefore, the bacteremia is a serious and urgent disease, and the improvement in treatment methods thereof have been awaited.

In the infectious disease, phagocytes including neutrophils, monocytes and macrophages primarily work in defense of the body. Emergence of bacteria in the blood is thought as invasion of predominant bacteria which have emerged from the tissue of the phagocyte. Bacteremia is a state wherein the bacteria is emerged into the blood, and a large amount of antibiotic is administrated to treat it wherein the causative bacteria is sensitive to the antibiotic. Generally, since antibiotics lower the functions of the internal organs such as liver, it is necessary to pay an attention to reduce an administration of an ineffective antibiotic to a patient in a serious state.

When bacteremia is defined as a case wherein phagocytesis of cells can not overcome the virulence of bacteria, then the bacteria spread in the body through the blood, bacteremia with serious symptoms due to toxins produced by the bacteria is called as sepsis. Proof of sepsis, in the other word, establishment of the diagnosis requires a check on the items of 1) clinical symptoms, 2) culturing of specimen, 3) gram-staining of the bacteria contained in the specimen, and 4) shock state, then, upon completing the check of these items, the treatment method is determined. Accordingly, to quickly and reliably identify the bacteria have been awaited in the art.

In the present method for detecting and identifying bacteria in a bacteremia-specimen, it is a common procedure to identify in selective medium a specimen which have positive signal in a routine process of culture bottle. However, to successfuly culture the bacteria from these blood specimen is quite difficult, then, if a large dose of antibiotics is administrated when bacteremia was suspected, bacteria in the blood will not be cultured and grown in many cases, therefore, the rate of culture bottle positive case become extremely low.

Although available sub-routine methods include instrumental analysis of constituents and metabolic products of bacteria (Yoshimi Benno, "Quick identification of bacteria with gas chromatography", Rinsho Kensa, Vol. 29, No.12, November 1985, Igaku Shoin ed.), a method utilizing specific antibody (Japanese Patent Provisional Publication No. 60-224068), and a hybridization method utilizing specificity of DNA (Japanese Phase Patent Provisional Publication No. 61-502376) have been developed, any of which are required to separate the bacteria and culture it. On the other hand, as a method established based on the function of phagocytes in infectious diseases, there is a method to examine, under an optical microscope, a stained smear of buffy coat wherein leukocyte of the blood sample is concentrated. Generally speaking, although the rate of detection of bacteria in buffy coat specimens from adult bacteremia patients is 30% at most, which is similar to that in earlobe blood specimens, it was reported that bacteria had been detected in seven cases of ten cases (70%) in newborn patients, therefore, an information concerning the presence of a bacteria in peripheral blood to be obtained by microscope examination on smear is an important for treatment.

Since the conventional methods necessiate the pretreatment which requires at least three to four days in total containing one to two day(s) for selective isolation of bacteria from a specimen, one day for cultivation, and one or more day(s) for fixation, and the culture thereof is continued in practice until the bacteria grow, the culture will needs one week or more even for C.B.-positive cases, therefore, this was a factor in high mortality of C.B.-positive patients being treated by the conventional methods. For example, according to the a report published in "The Journal of the Japanese Association for Infectious Diseases", Vol.58, No.2, p.122, 1984, even though the blood culture positive rate was 28.6% (163 cases/569 cases), the mortality was as high as 84.6% (138 cases/163 cases).

Further, it may be impossible to distinguish contamination at the cultivation by indigenous bacteria. For example, *Staphylococcus epidermides*, which is one of Staphylococci and is the causative bacterium of bacteremia, stayed in the skin of the normal person, then, there is a risk on contamination of a specimen with this bacterium when a needle is inserted into the skin.

As an important matter, under such circumstances above, since many bacteria in a specimen to be cultured have been incorporated into said phagocyte and are dead or stationary immobilized, the number of growable bacteria is small even under appropriate conditions for cultivation, thereby, the actual detection rate of bacteria through culture specimen is as low as about 10%. In the other word, at this moment, 90% of the examined blood, which have been cultured for further one or more day(s), of the patient suspected clinically as suffering with bacteremia can not clarify the presence of bacteria.

In light of the situation above, the present practice depends on a treatment to be started when bacteremia is clinically suspected without awaiting the detection results, that is to say, a trial and error method wherein an antibiotic having broad spectrum is administrated first, and if the antibiotic is not effective after one or two day(s), another antibiotic will be tried.

According to the method to stain the bacteria in the specimen, the constituents of the living body are also stained together with bacteria, therefore, experience to quickly identify bacteria according to thier image through microscope is required, then there may be cases that can be hardly diagnosed as bacteremia.

Although bacteremia is a disease wherein a rapid and exact diagnosis have been required, the conventional diagnosis method can not respond to such requirements.

DISCLOSURE OF INVENTION

The present invention was established in view of the problems in the art, and is directed to a probe having a specific reactivity with DNA or RNA obtained from primary causative bacteria of the infectious diseases, then provide a genetic information by analyzing the base sequence of DNA in the probe.

By the probe of the present invention, for example, a causative bacteria of the infectious diseases is detected rapidly and exactly, without cultivating/proliferating the bacteria, through a detection of DNA held in the causative bacteria digested and incorporated gradually with the phagocyte. Then, if primers are designed by referring to an information on base sequence of these probes, causative bacteria can identify, without the hybridization, by amplifying the DNA with PCR technique.

When non-radioactive probe, for example, biotinylated probe is used for hybridization, since such probe can be detected with an optical microscope in a conventional laboratory without radio isotope handling facilities, the detection process would be rapid and simple.

BEST MODE FOR CARRYING OUT THE INVENTION

Figure 1:
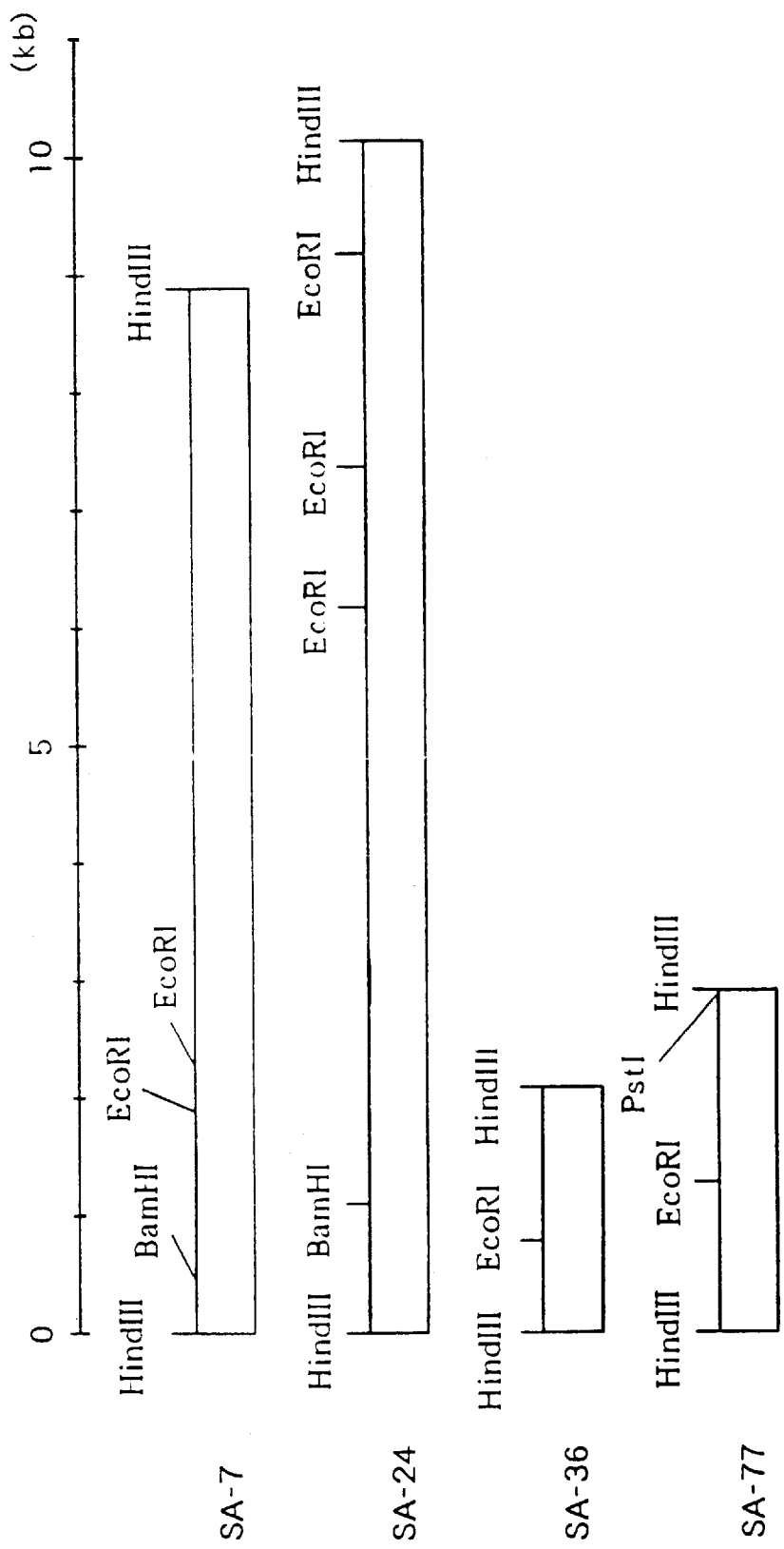
FIG. 1 is a restriction enzyme map of HindIII fragment on probe for detecting *Staphylococcus aureus*.
Figure 2:
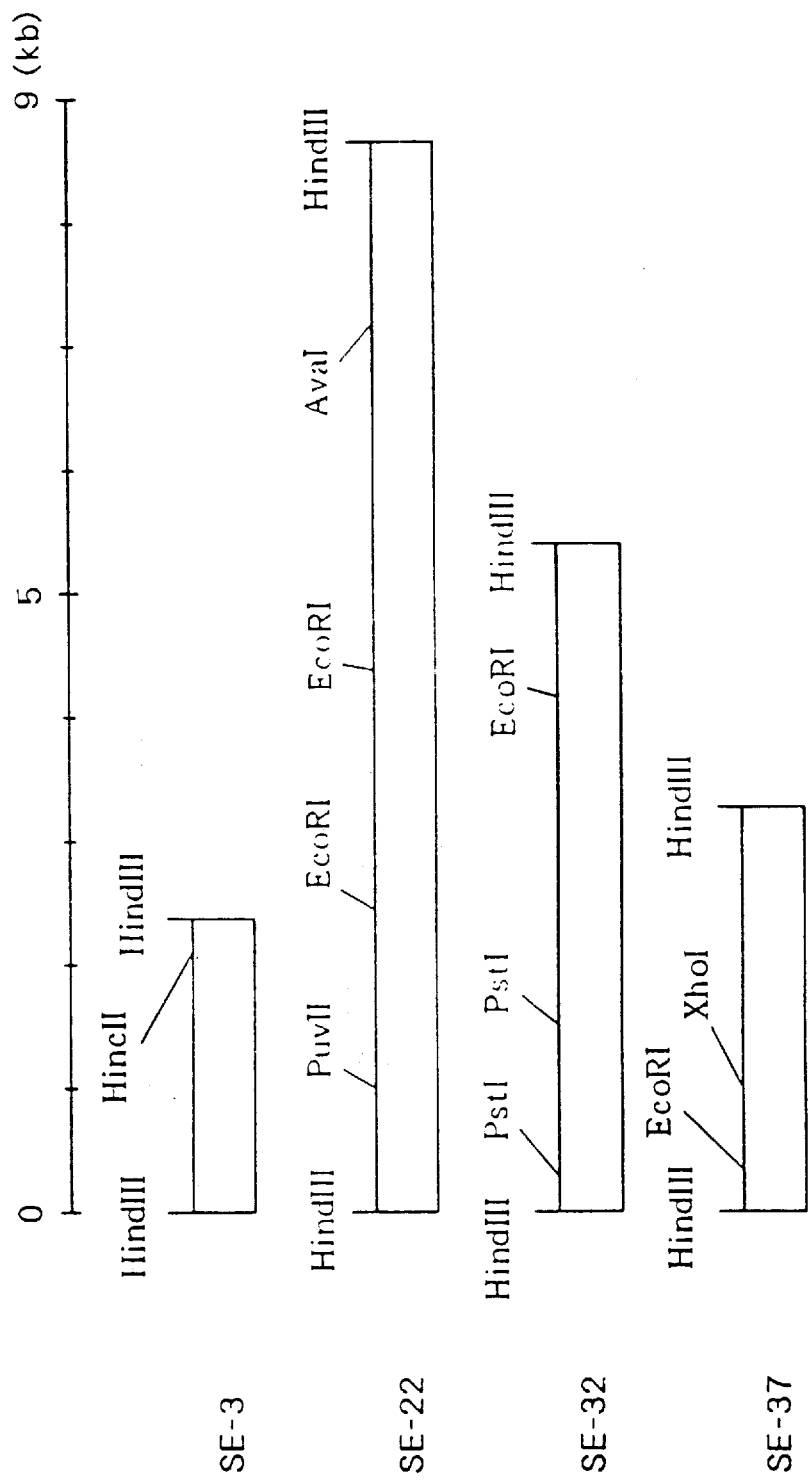
FIG. 2 is a restriction enzyme map of HindIII fragment on probe for detecting *Staphylococcus epidermidis*.
Figure 3:
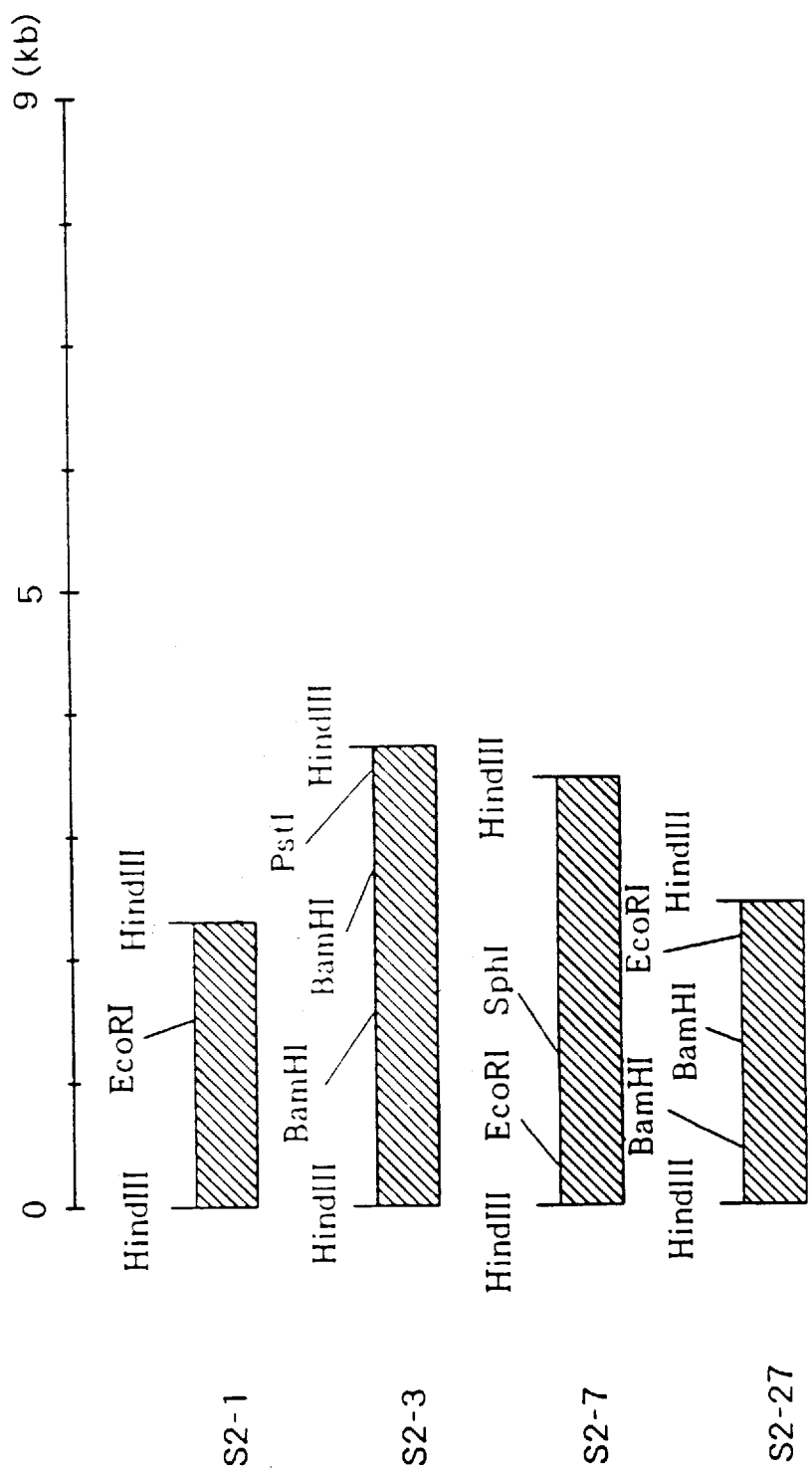
FIG. 3 is a restriction enzyme map of HindIII fragment on probe for detecting *Enterococcus faecalis*.
Figure 4:
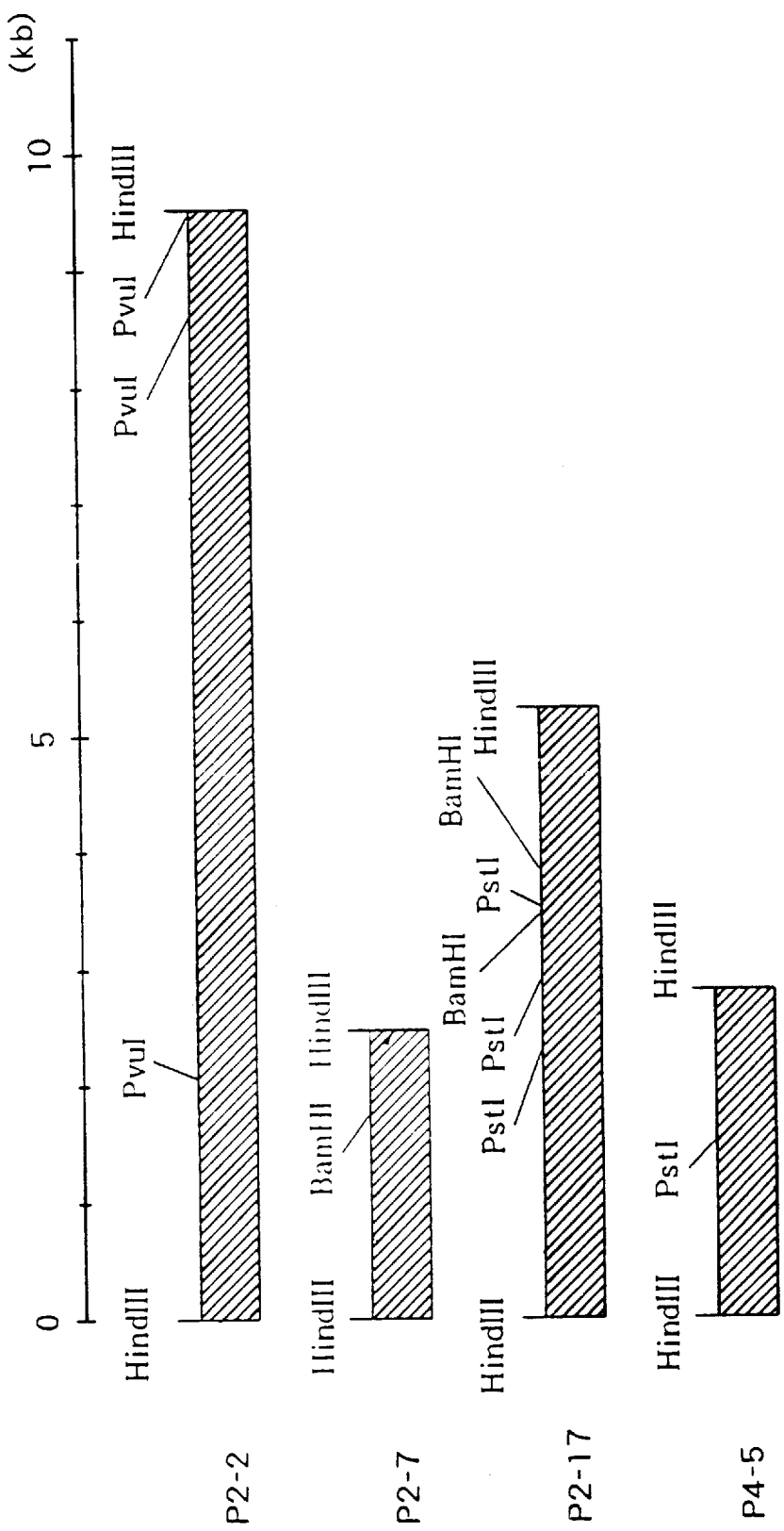
FIG. 4 is a restriction enzyme map of HindIII fragment on probe for detecting *Pseudomonas aeruginosa*.

Examples on probes prepared from *Staphylococcus aureus, Staphylococcus epidermidis, Enterococcus faecalis, Pseudomonas aeruginosa, Escherichia coli, Klebsiella pneumoniae* and *Enterobacter cloacae* (J. Infection, vol. 26, pp.159–170 (1993), J. Clin. Microbiol., vol.31., pp.552–557 (1993)), respectively listed as relatively popular causative bacteria of the infectious diseases, especially bacteremia were described as follows.

EXAMPLE 1

Preparation of DNA Probe from Causative Bacteria of Infectious Diseases (1) Isolation of Causative Bacteria of Infectious Diseases Blood collected from the patient who have been suffered with targeted diseases were applied to Blood Culture Method (BBC System: Blood Culture System; Roche) and to a conventional identification kit (Api 20, Apistaf, Apistlep 20: Bio-Meryu), and the each causative bacterium was isolated and identified according to the manual of said kit.

(2) Extraction and Purification of Genomic DNA from Isolated Strain

Strains isolated in the above (1) was cultivated overnight in BHI (Brain Heart Infusion) medium, collected the cultivated bacteria, added thereto achromopeptidase in stead of lysozyme, then, Genomic DNA was extracted according to Saito-Miura Method ("Preparation of Transforming Deoxyribonucleic Acid by Phenol Treatment", Biochem. Biophys. Arta. vol. 72, pp.619–629), and extracted DNA was digested with restriction enzyme HindIII and was random cloned into vector pBR322.

(3) Selection of Probe having Specificity to Species of Origin Bacteria

*Escherichia coli* containing each clone prepared according to Manual of Maniatis (T. Maniatis, et al., "Molecular Cloning (A Laboratory Manual)", Cold Spring Harbour Laboratory (1982)) was cultivated with small scale culture, and obtained plasmids containing each clone.

These plasmids were digested with restriction enzyme HindIII, thereby inserts were separated completely from plasmids with 1% agarose-gel electrophoresis (Myupid: Cosmo-Bio), then, were transcribed to nylon membrane with Southern-Transfer Technique (Paul Biodine A: Paul), and were cross-hybridized with a probe prepared by labelling $^{32}$P-dCTP (Amersham) through nick-translation to chromosome DNA from each bacteria species aforelisted.

In this hybridization, a probe which did not cross-react with any insert except for a probe prepared from the origin species thereof was selected as a probe containing DNA fragment which is specific to causative bacteria of the infectious diseases.

With regard to probes prepared from *Escherichia coli, Klebsiella pneumoniae, Enterobacter cloacae*, since these bacteria are belonged to the same group (enteric bacteria; Gram negative aerobic bacillus) as a causative bacteria of bacteremia (See, J. Infection, vol. 26, pp.159–170 (1993), J. Clin. Microbiol., vol.31., pp. 552–557 (1993), supra), and the cross-reaction had been confirmed among said three bacteria in the foregoing series experiments on the specificity, each probe prepared from one of said three bacteria was designated as a probe for detecting all these bacteria as a relevant bacteria.

Probes (denotation) selected from each species through the foregoing methods are listed in the following Table 1.

TABLE 1

| SPECIES | DENOTATION |
| --- | --- |
| *Staphylococcus aureus* | SA-7, SA-24, SA-36, SA-77 |
| *Staphylococcus epidermidis* | SE-3, SE-22, SE-32, SE-37 |
| *Enterococcus faecalis* | S2-1, S2-3, S2-7, S2-27 |
| *Pseudomonas aeruginosa* | P2-2, P2-7, P2-17, P4-5 |
| *Escherichia coli* | EC-24, EC-34, EC-39, EC-625 |
| *Klebsiella pneumoniae* | KI-50 |
| *Enterobacter cloacae* | ET-12, ET-49 |

Restriction enzyme maps of each probe were also illustrated in FIGS. 1–6 respectively.

EXAMPLE 2

Evaluation on Species-Specificity of Each DNA Probe

Reactivity between each probe and DNA from causative bacteria of infectious diseases were examined acooding to the following method. po First of all, as subject strains for an examination, clinical isolates of *Staphylococcus aureus, Staphylococcus epidermidis, Enterococcus faecalis, Pseudomonas aeruginosa, Escherichia coli, Klebsiella pneumoniae*, and *Enterobacter cloacae* were isolated according to the method of Example 1 (1) above.

Then, DNA of each clinical isolate were extracted according to the method of Example 1 (2), and samples for dot-blot-hybridization were obtained by spotting certain amount (e.g., 5 µl) of DNA to nylon filter and selecting the isolates denatured with alkaline. Hybridization on DNA probes prepared from each subjected bacterium and labelled with biotin (Bio-dUTP; BRL) were performed overnight according to Manual of Maniatis, supra, under the condition of 45% formamide, 5×SSC, 42° C.

Samples obtained through overnight hybridization were washed twice with 0.1×SSC, 0.1% SDS for 20 minutes at 55° C., then, were detected the color reaction with Streptavidin-ALP conjugates (BRL), and evaluated the hybridization.

Experimental results on reactivity between each probe and DNA of each clinical isolate are illustrated in the following table 2 (i)–(vi). With regard to a denotation in the tables, denotation of "+" refers to the presence of a signal on hybridization, while that of "−" refers to the absence of a signal on hybridization.

TABLE 2 (i)

|  | SA-7 | SA-24 | SA-36 | SA-77 |
|---|---|---|---|---|
| Staphylococcus aureus | + | + | + | + |
| Staphylococcus epidermidis | − | − | − | − |
| Enterococcus faecalis | − | − | − | − |
| Pseudomonas aeruginosa | − | − | − | − |
| Escherichia coli | − | − | − | − |
| Klebsiella pneumoniae | − | − | − | − |
| Enterobacter cloacae | − | − | − | − |

TABLE 2 (ii)

|  | SE-3 | SE-22 | SE-32 | SE-37 |
|---|---|---|---|---|
| Staphylococcus aureus | − | − | − | − |
| Staphylococcus epidermidis | + | + | + | + |
| Enterococcus faecalis | − | − | − | − |
| Pseudomonas aeruginosa | − | − | − | − |
| Escherichia coli | − | − | − | − |
| Klebsiella pneumoniae | − | − | − | − |
| Enterobacter cloacae | − | − | − | − |

TABLE 2 (iii)

|  | S2-1 | S2-3 | S2-7 | S2-27 |
|---|---|---|---|---|
| Staphylococcus aureus | − | − | − | − |
| Staphylococcus epidermidis | − | − | − | − |
| Enterococcus faecalis | + | + | + | + |
| Pseudomonas aeruginosa | − | − | − | − |
| Escherichia coli | − | − | − | − |
| Klebsiella pneumoniae | − | − | − | − |
| Enterobacter cloacae | − | − | − | − |

TABLE 2 (iv)

|  | P2-2 | P2-7 | P2-17 | P4-5 |
|---|---|---|---|---|
| Staphylococcus aureus | − | − | − | − |
| Staphylococcus epidermidis | − | − | − | − |
| Enterococcus faecalis | − | − | − | − |
| Pseudomonas aeruginosa | + | + | + | + |
| Escherichia coli | − | − | − | − |
| Klebsiella pneumoniae | − | − | − | − |
| Enterobacter cloacae | − | − | − | − |

TABLE 2 (v)

|  | EC-24 | EC-34 | EC-39 | EC-625 |
|---|---|---|---|---|
| Staphylococcus aureus | − | − | − | − |
| Staphylococcus epidermidis | − | − | − | − |
| Enterococcus faecalis | − | − | − | − |
| Pseudomonas aeruginosa | − | − | − | − |
| Escherichia coli | + | + | + | + |
| Klebsiella pneumoniae | + | + | + | + |
| Enterobacter cloacae | + | + | + | + |

TABLE 2 (vi)

|  | ET-12 | ET-49 | KI-50 |
|---|---|---|---|
| Staphylococcus aureus | − | − | − |
| Staphylococcus epidermidis | − | − | − |
| Enterococcus faecalis | − | − | − |
| Pseudomonas aeruginosa | − | − | − |
| Escherichia coli | + | + | + |
| Klebsiella pneumoniae | + | + | + |
| Enterobacter cloacae | + | + | + |

Apparently from Table 2 above, each probe have reacted only with DNA obtained from origin strain (or relative strain thereof) and not reacted (hybridized) with any DNA obtained from strains except for strains from the origin strain, therefore, their specificity have been confirmed.

EXAMPLE 3

Analysis of Base Sequence

Base sequence of DNA probes (total 23 probes) of the present invention, which have been confirmed their specificity to the origin species in the Examples 1 and 2, were sequenced according to the following method.

(1) Preparation of Plasmid DNA

*Escherichia coli* K-12, JM109 transformants, wherein the subcloned insert fragments (to be seqeuenced) is contained in pGem-3Z (Promega), was inoculated in 5 ml of Luria-Bactani Medium (bacto-tryptone, 10 g/lL; bacto-yeast extract, 5 g/lL; NaCl, 10 g/lL; adjusted pH to 7.0 with 5N NaOH) and cultivated overnight.

Culture liquid was centrifuged (5,000 rpm, 5 min.) and collected the bacteria. 100 µl of solution of 50 mM glucose/ 50 mM Tris-HCl (pH8.0)/10 mM EDTA containing 2.5 mg/ml of lysozyme (Sigma) was added to precipitate, and left at room temperature for five minutes. 0.2M NaOH solution containing 1% of sodium dodecyl sulfate (Sigma) was added to the suspension so obtained and mixed therewith. 150 µl of 5M pottasium acetate solution (pH 4.8) was further added thereto and mixed therewith, then iced for 15 minutes.

Supernatant obtained by centrifugation (15,000 rpm, 15 min.) was treated with phenol/CHCl$_3$ and added thereto ethanol of two times volume, then precipitate was obtained by centrifugation (12,000 rpm, 5 min.). This precipitate was dissolved in 100 µl of solution of 10 mM Tris-HCl (pH7.5) /0.1 mM EDTA and added thereto 10 mg/ml RNaseA (Sigma) solution, then left it at room temperature for 15 minutes.

300 µl of 0.1M sodium acetate solution (pH 4.8) was added to this preparation and treated with phenol/CHCl$_3$, then precipitate was obtained by adding ethanol to supernatant. DNA samples were prepared by drying this precipitate and dissolving in 10 µl distilled water.

(2) Pretreatment for Sequencing

Pretreatment for sequencing was performed with Auto-Read™ Sequencing Kit (Pharmasia).

Concentration of DNA to become a template was adjusted to 5–10 μg in 32 μl. 32 μl of template DNA was transferred to 1.5 ml mini-tube (Eppendolf), and added thereto 8 μl of 2M NaOH solution, then mixed gently therewith. After instant centrifugation, it was left at room temperature for 10 minutes.

7 μl of 3M sodium acetate (pH 4.8) and 4 μl of distilled water, then 120 μl of ethanol were added thereto then mixed therewith, and left for 15 minutes on dry ice. DNA which have been precipitated by centrifugation for 15 minutes were collected, and supernatant was removed carefully. The precipitate so obtained were washed with 70% ethanol and centrifuged for 10 minutes. Then, the supernatant was removed carefully again and dried the precipitate under the reduced pressure.

The precipitate was dissolved in 10 μl of distilled water, then 2 μl of fluorescent primer (0.42 $A_{260}$ unit/10 ml, 4–6 pmol) [M13 Universal Primer; 5'-Fluorescein-d[CGACGTTGTAAAACGACGGCCAGT]-3' (SEQ ID NO:24) (1.6 pmol/μl; 0.42 $A_{260}$ unit/ml); M13 Reverse Primer, 5'-Fluorescein-d[CAGGAAACAG CTATGAC]-3' (SEQ ID NO:25) (2.1 pmol/μl; 0.42 $A_{260}$ unit/ml)] and 2 μl of saline for annealing were added thereto, and mixed gently.

After instant centrifugation, they were heat-treated at 65° C. for 5 minutes and rapidly transferred it to a circumstance of 37° C. and kept the temperature for 10 minutes. After keeping the temperature, it was left at room temperature for 10 minutes or more and centrifugated instantly. Then, samples were prepared by adding thereto 1 μl of an elongation saline and 3 μl of dimethyl sulfoxide.

Four mini-tubes have been identified with one of marks of "A", "C", "G" and "T", and, according to the mark, 2.5 μl of A Mix (dissolved ddATP with dATP, dCTP, $c^7$dGTP and dTTP), C Mix (dissolved ddCTP with dATP, dCTP, $c^7$dGTP and dTTP), G Mix (dissolved ddGTP with dATP, dCTP, $c^7$dGTP and dTTP), or T Mix (dissolved ddTTP with dATP, dCTP, $c^7$dGTP and dTTP) were poured into each identified tube. Each solution was preserved in freezed condition, and the solution was heated at 37° C. for one minute or more to use it.

2 μl of diluted T7DNA polymerase (Pharmacia; 6–8 units/2 μl) was added to DNA sample, and completely mixed by pipetting or mixing it gently. Immediately after completing the mixing, these mixed solution was poured into 4.5 μl of four-types solution respectively which have kept the certain temperature. Fresh tips were used at the time of pouring.

The solution have been kept for five minutes at 37° C., then 5 μl of termination solution were poured into each reaction-solution. Fresh tips were used for pouring. Immediately after keeping the solution for 2–3 minutes at 90° C., it was cooled on ice. 4–6 μl/lane of the solution was applied to the electrophoresis.

(3) Sequencing on Base Sequence

Sequencing on each base sequence of probes, disclosed in Examples 1 and 2, having the specificity against *Staphylococcus aureus* or *Staphylococcus epidermidis* were performed with A.L.F. DNA Sequencer System (Pharmacia) under an electrophoresis condition of 45° C. for 6 hours.

Then, base sequences of the probes (SEQ ID.No.) prepared from each causative bacteria of the infectious diseases and listed in the following table 3 were disclosed in the sequence listing attached hereto.

TABLE 3

| SPECIES | Probes (SEQ ID. No.) |
| --- | --- |
| *Staphylococcus aureus* | SA-7 (1), SA-24 (2) |
|  | SA-36 (3), SA-77 (4) |
| *Staphylococcus epidermidis* | SE-3 (5), SE-22 (6) |
|  | SE-32 (7), SE-37 (8) |
| *Enterococcus faecalis* | S2-1 (9), S2-3 (10) |
|  | S2-7 (11), S3-27 (12) |
| *Pseudomonas aeruginosa* | P-2 (13), S2-7 (14) |
|  | P2-17 (15), P4-5 (16) |
| *Escherichia coli* | EC-24 (17), EC-34 (18), |
|  | EC-39 (19), EC-625 (20) |
| *Klebsiella pneumoniae* | KI-50 (23) |
| *Enterobacter cloacae* | ET-12 (21), ET-49 (22) |

Thereby, genetic information concerning the specific site of each causative bacteria of the infectious diseases (or relative bacteria thereof) have been clarified.

According to probes of the present invention, for example, causative bacteria of the infectious diseases which have incorporated into the phagocyte can be directly detected, and rapidly and exactly identified without proliferating the bacteria. That is to say, according to the diagnosis using the probe of the present invention, identification of the bacteria can be realized with single specimen, then, reduced the necessary time for diagnosis to about one to two day(s), while the conventional method (with low detection rate) required 3–4 days, and improved remarkably the detection rate. Therefore, this invention can provide an objective factors for the treatment of bacteremia, then realize the effective treatment in the early stage of the infectious diseases, and expect to reduce the mortality.

Then, by clarifying the base sequences of probes which specifically react with primary bacteria of the infectious diseases, these probes can be prepared artifically. Further, a part of information on the analyzed base sequences may be used for rapidly diagnosing the causative bacteria by amplifying DNA of causative bacteria of the infectious diseases in the clinical specimen with PCR technique and primers prepared by making use of said information.

Further, by comparing base sequences of Genomic DNA in the clinical specimen with that of the present invention, rapid identification of the species of the causative bacteria of infectious diseases can be realized.

As stated above, the present invention provide desirable probes for diagnosing the infectious diseases, then expect utilities as a factor to prepare primers for PCR and standard sequence for a comparison with Genomic DNA in the clinical specimen, and further expect an effect to provide valuable hints for preparing and developing the other probes which specifically react with causative bacteria of the infectious diseases.

Then, since the base sequences disclosed in the present application was obtained by random-cloning the Genomic DNA of clinical isolates, utilities of the base sequences of the present invention should be extended to the complementary strands thereof.

Further, although it may be thought that DNA obtained from the wild strains contain the mutated portion, apparently from the disclosure of the Examples above, said mutated DNA portion would not affects the utilities to be derived by the present invention comprising the specificity of the probes of the present invention in the hybridization for a diagnosis of the infectious diseases, and an usage of the information on the base sequences disclosed in the present application to design the primers for PCR technique to realize a rapid diagnosis of the infectious diseases.

We claim:

1. A probe composition for detecting *Staphylococcus aureus*, wherein the probe composition consists essentially of
    (a) the DNA of any one of SEQ ID NOS:1 through 4, or
    (b) the complement of (a).

2. A method for detecting the presence of *Staphylococcus aureus* in a sample comprising the steps of contacting nucleic acid from said sample with the probe composition of claim 1 and detecting hybridization of the nucleic acid from said sample with DNA in said probe composition as an indication of the presence of *Staphylococcus aureus*.

* * * * *

UNITED STATES PATENT AND TRADEMARK OFFICE
CERTIFICATE OF CORRECTION

PATENT NO.    : 5,807,673
DATED         : September 15, 1998
INVENTOR(S)   : Ohno et al.

It is certified that error appears in the above-identified patent and that said Letters Patent is hereby corrected as shown below:

<u>Title page,</u>
Item [56], References Cited, OTHER PUBLICATIONS, after "Antimicrobial" please insert -- Agents -- therefore.

Figure 5:
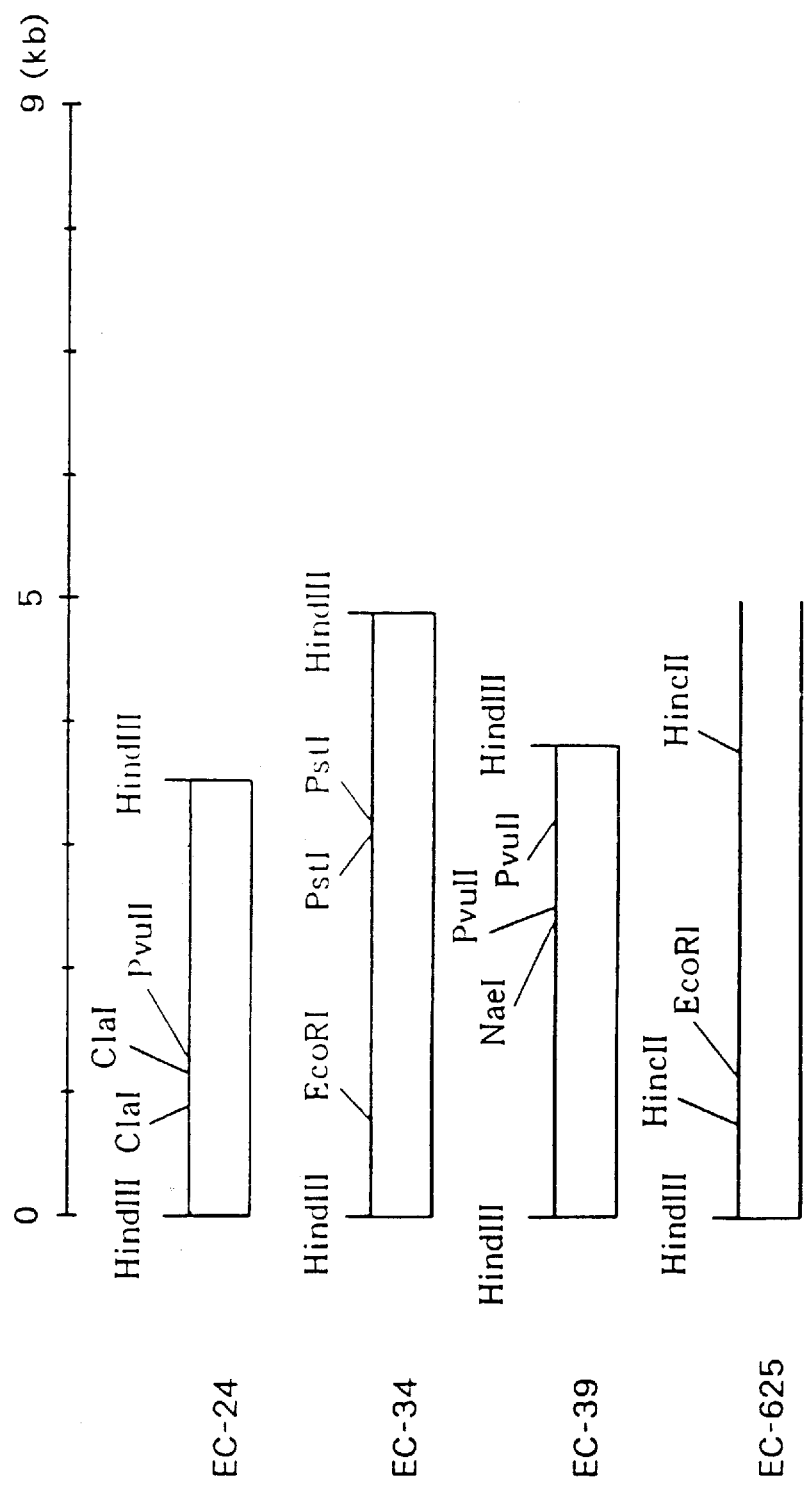
FIG. 5 is a restriction enzyme map of HindIII fragment on probe for detecting *Escherichia coli*.
Figure 6:
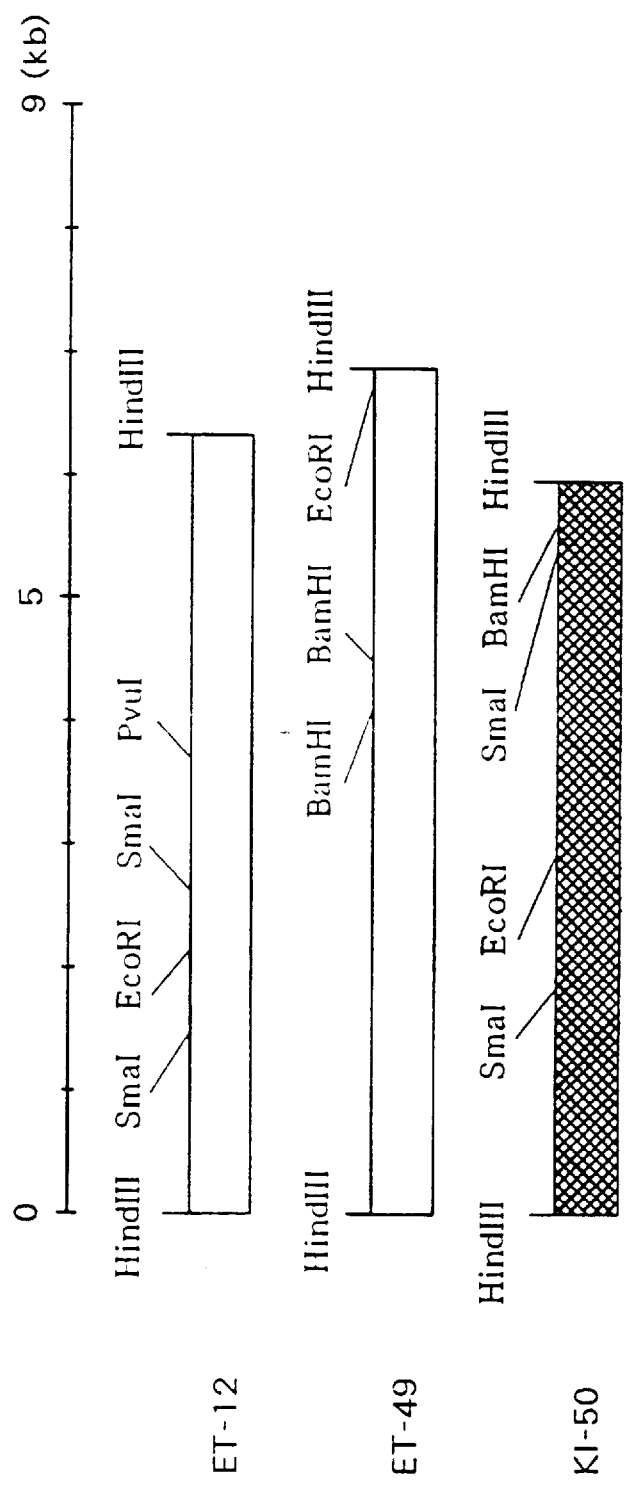
FIG. 6 is a restriction enzyme map of HindIII fragment on probe for detecting *Enterobacter cloacae* and *Klebsiella pneumonia*.

<u>Drawings,</u>
FIG. 5, please delete

"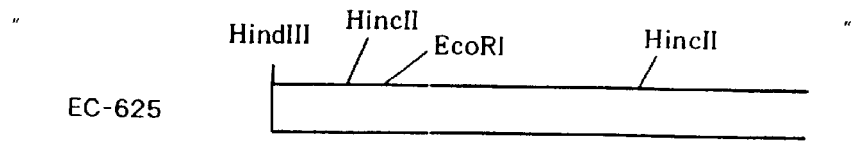"

and insert

-- 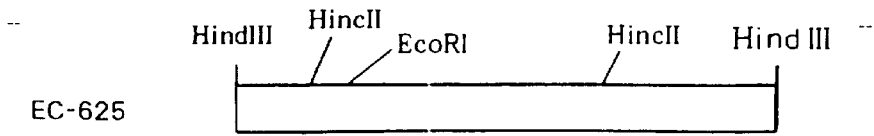 -- therefor.

<u>Column 1,</u>
Line 19, please delete "bateremia" and insert -- bacteremia -- therefor.

<u>Column 2,</u>
Line 36, please delete "*epidermides*" and insert -- *epidermidis* -- therefor.
Line 63, please delete "their" and insert -- their -- therefor.

<u>Column 4,</u>
Line 5, please delete "Arta" and insert -- Acta -- therefor.
Line 61, please delete "acooding" and insert -- according -- therefor.
Line 62, after "method." please delete "po" therefor.
Line 62, before "First of all" begin new paragraph.

UNITED STATES PATENT AND TRADEMARK OFFICE
CERTIFICATE OF CORRECTION

PATENT NO.   : 5,807,673
DATED        : September 15, 1998
INVENTOR(S)  : Ohno et al.

It is certified that error appears in the above-identified patent and that said Letters Patent is hereby corrected as shown below:

<u>Column 6,</u>
Line 39, please delete "seqeuenced" and insert -- sequenced -- therefor.
Line 52, please delete "pottasium" and insert -- potassium -- therefor.

<u>Column 7,</u>
Line 3, please delete "(Pharmasia)" and insert -- (Pharmacia) -- therefor.

<u>Column 8,</u>
Line 16, please delete "S2-7(11), S3-27 (12)" and insert -- S2-7(11), S2-27(12) -- therefor.

Signed and Sealed this

Twelfth Day of November, 2002

*Attest:*

*Attesting Officer*

JAMES E. ROGAN
*Director of the United States Patent and Trademark Office*

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
( A ) LENGTH: 8959 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Staphylococcus aureus
( B ) STRAIN: Clinical Isolate SA- 7

( x i ) SEQUENCE DESCRIPTION: SEQ ID NO:1:

| | | | | | | |
|---|---|---|---|---|---|---|
| AAGCTTTATC | TGCTGAATAT | ACCGCATTTT | TTATCTTGTT | AATTGTCGGC | ACATTTCTT | 60 |
| CAATAGTTAA | ACCTGCTTTG | TTAGCTTCTT | CTAATAATGC | TCGAGTTACT | GTTTATTAAA | 120 |
| TGTTCATTCG | CTTTTCAACG | ACAACTGACG | AACCAGTATC | TGTTAGCTTA | GACGCAACAG | 180 |
| CGTTAATCTT | CTGATTCACC | TTAAATTCTA | CATCTGCTTT | TTGAGGCTGC | TTACGTAGTG | 240 |
| TCCCGGTAAT | TTCATGTGTA | AACTTAGATG | GGATGTAAAT | ACCTGCAAAA | TATTTACCCA | 300 |
| TTTTTATCTC | ATGATCAGCT | TTCTCTCTAC | TTACAAACTG | CCAATCAAAA | CTTTTATTTT | 360 |
| TCTTGAGTGT | ATTAACCATC | GTATTACCGA | CATTAACTTT | TTTCCCTCTG | ATTGTGTCGC | 420 |
| CTTTATCTTC | ATTAACGACT | GCGACCTTGA | TGTGTCCCGT | GTTGCCATAT | GGATCCCACA | 480 |
| TTGCCCATAA | GTTAAACCAA | GCGTAGAACG | ATGGCAAAAT | AGCTAAGCCT | GCTAAGATAA | 540 |
| TCCACACAGC | TGGCGTCTTA | GCTACTTTCT | TCAGATCCAT | TTTAAATAAT | TTAAATGCGT | 600 |
| TCTTCATTGT | CACACTCCTA | TGTAGGAATT | ATTCATATTT | TTTATATATT | TTTTGTAAAT | 660 |
| TAATTTATTT | TTGCGTTGTG | AATTAGTATA | ATCAATTTAC | TGGAAGATAT | TTAGTCGATT | 720 |
| GATACCTATC | AACTATTTTC | AGCATACGAT | AAATTATAAC | AAATCATAGT | TTATTATCAC | 780 |
| ACTTAATTAT | TATATTTTTC | AAGGGAGAAT | ACGAAATATG | CCTAAAAATA | AAATTTAAT | 840 |
| TTATTTGCTA | TCAACTACCC | TCGTATTACC | TACTTTAGTT | TCACCTACCG | CTTATGCTGA | 900 |
| TACACCTCAA | AAAGATACTA | CAGCTAAGAC | AACATCTCAT | GATTCAAAAA | AATCTAATGA | 960 |
| CGATGAAACT | TCTAAGGATA | CTACAAGTAA | AGATACTGAT | AAAGCAGACA | ACAATAATAC | 1020 |
| AAGTAACCAA | GACAATAACG | ACAAAAAATT | TAAAACTATA | GACGACAGCA | CTTCAGACTC | 1080 |
| TAACAATATC | ATTGATTTTA | TTTATAAAGA | ATTTACCACA | AACCAATATA | AACCAATTGC | 1140 |
| TAACCAAAAA | TAAATACGAT | GATAATTACT | CATTAACAAC | TTTAATCCAA | AACTTATTCA | 1200 |
| ATTTAAATTC | GGATATTTCT | GATTACGAAC | AACCTCGTAA | TGGCGAAAAG | TCAACAAATG | 1260 |
| ATTCGATAAA | AACAGTGACA | TAGCATCAAA | AATGACACTG | ATACGCAATC | ATCTAAACAA | 1320 |
| GATAAAGCAG | ACAATCAAAA | AGCACCTAAA | TCAAACAATA | CAAAACCAAG | TACATCTAAT | 1380 |
| AAGCAACCAA | ATTCGCCAAA | GCCAACACAA | CCTAATCAAT | CAAATAGTCA | ACCAGCAAGT | 1440 |

```
GACGATAAAG  CAAATCAAAA  ATCTTCATCG  AAAGATAATC  AATCAATGTC  AGATTCGGCT  1500

TTAGACTCTA  TTTTGGATCA  ATACAGTGAA  GATGCAAAGA  AAACACAAAA  AGATTATGCA  1560

TCTCAATCTA  AAAAAGACAA  AAATGAAAAA  TCTAATACAA  AGAATCCACA  GTTACCAACA  1620

CAAGATGAAT  TGAAACATAA  ATCTAAACCT  GCTCAATCAT  TCAATAACGA  TGTTAATCAA  1680

AAGGATACAC  GTGCAACATC  ATTATTCGAA  ACAGATCCTA  GTATATCTAA  CAATGATGAT  1740

AGCGGACAAT  TTAACGTTGT  TGACTCAAAA  GATACACGTC  AATTTGTCAA  ATCAATTGCT  1800

AAAGATGCAC  ATCGCATTGG  TCAAGATAAC  GATATTTATG  CGTCTGTCAT  GATTGCCCAA  1860

GCAATCTTAG  AATCTGACTC  AGGTCGTAGT  GCTTTAGCTA  AGTCACCAAA  CCATAATTTA  1920

TTCGGTATCA  AAGGTGCTTT  TGAAGGGAAT  TCTGTTCCTT  TTAACACATT  AGAAGCTGAT  1980

GGTAATAAAT  TGTATAGTAT  TAATGCTGGA  TTCCGAAAAT  ATCCAAGCAC  GAAAGAATCA  2040

CTAAAGATT   ACTCTGACCT  TATTAAAAAT  GGTATTGATG  GCAATCGAAC  AATTTATAAA  2100

CCAACATGGA  AATCGGAAGC  CGATTCTTAT  AAAGATGCAA  CATCACACTT  ATCTAAAACA  2160

TATGCTACAG  ATCCAAACTA  TGCTAAGAAA  TTAAACAGTA  TTATTAAACA  CTATCAATTA  2220

ACTCAGTTTG  ACGATGAACG  CATGCCAGAT  TTAGATAAAT  ATGAACGTTC  TATCAAGGAT  2280

TATGATGATT  CATCAGATGA  ATTCTGTTCC  TTTTAACACA  TTAGAAGCTG  ATGGTAATAA  2340

ATTGTATAGT  ATTAATGCTG  GATTCCGAAA  ATATCCAAGC  ACGAAAGAAT  CACTAAAAGA  2400

TTACTCTGAC  CTTATTAAAA  ATGGTATTGA  TGGCAATCGA  ACAATTTATA  AACCAACATG  2460

GAAATCGGAA  GCCGATTCTT  ATAAAGATGC  AACATCACAC  TTATCTAAAA  CATATGCTAC  2520

AGATCCAAAC  TATGCTAAGA  AATTAAACAG  TATTATTAAA  CACTATCAAT  TAACTCAGTT  2580

TGACGATGAA  CGCATGCCAG  ATTTAGATAA  ATATGAACGT  TCTATCAAGG  ATTATGATGA  2640

TTCATCAGAT  GAATTCAAAC  CTTTCCGCGA  GGTATCTGAT  AGTATGCCAT  ATCCACATGG  2700

CCAATGTACT  TGGTACGTAT  ATAACCGTAT  GAAACAATTT  GGTACATCTA  TCTCAGGTGA  2760

TTTAGGTGAT  GCACATAATT  GGAATAATCG  AGCTCAATAC  CGTGATTATC  AAGTAAGTCA  2820

TACACCAAAA  CGTCATGCTG  CTGTTGTATT  TGAGGCTGGA  CAATTTGGTG  CAGATCAACA  2880

TTACGGTCAT  GTAGCATTTG  TTGAAAAAGT  TAACAGTGAT  GGTTCTATCG  TTATTTCAGA  2940

TCAATGTTAA  AGGATTAGGT  ATCATTTCTC  ATAGAACTAT  CAATGCAGCT  GCCGCTGAAG  3000

AATTATCATA  TATTACAGGT  AAATAAGTAT  TATTAAACCC  GCAAAATTTA  TAAGTATAAA  3060

CAAGGAGTTC  GGACTTAAAC  ATATTTCTGT  TCATAAGTCC  GATTTCTTAT  TCAATTAAAC  3120

CCGAGGTATT  CAGTTCGAAC  GCCTCGGGTC  ATTTATATA   AATATATTAT  TTTATGTTCA  3180

AATGTTCCTC  ATCATATCCG  TTTCAATTGT  CATCTCACAC  ATTTATAAA   TATGAGCAAA  3240

TGTACTTATT  TTCAAACATT  ACTGCCTAGC  TTTAATTGAC  GTTATATTAA  CTATAAACTA  3300

CTTTTCCATG  ACTCTACGGA  TTCAATGTCA  CATGAGCGTG  ATAAATTTG   TTCAATAATA  3360

AAGTCATGTT  TATCATCTGA  TCTATCACCA  ACAGCATCTT  CTAAAACAGT  AATATAATAG  3420

TCTTTATCTA  CACTTTCTAA  TGCCGTGCTC  AATACAGCTC  CACTCGTAGA  GACACCCGTT  3480

AATACTAAAT  GATTAATATC  ATTTGCACGT  AAATAAACTT  CCAAGTAACT  ACCTGTAAAT  3540

GCGCTAAAGC  GTCGCTTAGA  AATAATCGGC  TCATCTTCTA  GTGGTGCTAA  ATCTTCAAGT  3600

ATTCGTGTAG  ATGCATCTGC  TTCAGTAATC  GCATATCCTT  GAGCTTTAAT  TGTTGAAAAC  3660

ACTTTATTAC  TCGAGGAGAC  ATCATTAAAA  TGCTTATCTA  ACACTAAACG  TATGAAAATG  3720

ACTGGTATTC  GATGTTGTCT  TGCTGCTTCA  ATTGCTCTCT  GATTCGCTTT  AATAATATTT  3780

TTTATTCTAG  GTACACTACT  CGCTATACTT  CTTGCATATC  CAAACTAATA  GCGCCGTTTT  3840
```

```
TCGAGACATC TTCATTCTCC TTTACTTCTG TAGTTCTAAG TCGTTAAATT CATTATAACG    3900

TTAAAATGAT GGACAATCTA TTCATTGCAT TTTGCATATA CTTCACAATA ATTTAAGGGG    3960

GAAATAAGAC GTCTTATATA CTTAAAAAAA TATATAGATG CTCTTCCCCC AATATAATTA    4020

TGCTTTATTT TTCAACTTAT TGCGTCGTGA TAACCAAATC ATTAGTACAC CCATTGCACC    4080

AACAATTACA GATATCGGCA ACCAATGTTC TTTTATCGTT TCCCCGCTTT AGGCAAGATA    4140

CATTACCATC AGCATTTAAT AATCCACTTA ACAATCCATT ACCTTTACCA AGTGTTACGT    4200

CTTTTCTGGC TTTGGTGTGG GTATATCTGG AATACTGTCT AATAAATTTG ATCCTTGATT    4260

CATTAAATTT GCTAACTTAT TTAAATCCGT TGTTTTCCCA TTTTTATTCA ATCGATCTAG    4320

TAAACTTGGA CGATTACTA  TTGGTGATAA AATATAGTCT ATATCTTTTT TCGTTTGATT    4380

GAGTCTCTTT TGTAAATTCA ATAAATCATC CGCTTTACCA TTCAATGCCG ATTAACTAA     4440

ATTAAAAATT TTATTTGAT  CTGTTTCTAT TTAGTAATT  AAATCTGCCA GTAATTTTGC    4500

CTTTTGTCTT TCTATACGTG TTGCTAAAAT CGTTTCAATT GCTTGCTTTT TATCTTTGGC    4560

ATTATTCAAA ATTGCTTTTA ATATATCATC TGAAGACGTG TCGCCAGTTG ATGCAAAATG    4620

TTTCTTCAAT TGGTCAACGA TTTGGCGATT TGATAATCCT TTATTCGTCC AATCTTTAGC    4680

CAATTTATCT GCTTCAGCTT TTCCTAATTT CGTTGTAAG  ATTTGAGAAA TCAATAGCGA    4740

CTTATCTTGT GATTGATCAA TCAATGACGT TAATAAATCA TCACTCGTTG TCAGAGATAG    4800

TTGATCAATA TGACGAGTAA TTTGATCTGC AATTTGTTGA TCTGTTTTAC CATCAACACG    4860

TATATCTTTT AGAATTTTAT CTGCCTCGTC TTTATTAAAT ATACTTTCTA AAATGCTTTG    4920

TGTAGCATAC TTTTTATCAT CAGTACGTGC AAGTTCTTCC AAAATAATAT TCGTTGACT     4980

TTTTATACGC TCTTTCGTCT TATTTACTTC GCTCATTAAG TCTGATTTTT GATTTTAGG    5040

AAGTTGCGTA TTTGCAATAC GTTGATCTAA AGATTGTAAC GTATTCAGTT TATGATATGT    5100

GTAATGTTGC GTTGAGGCAT TACTTTTAGC CAATTTTTCA ATCATAGCAT GATTAATTTT    5160

ATCGCTTCCT TGTAATTTAT CAGTGAGTTG ATTACTATGG CTTTGATTCT CTTCATTTGA    5220

AAGAAATTTA TTTAACACAA CATGTCCAGA ACCATCATTA TTTGGCGTTT TAGCTACTTC    5280

ATGATTACTA TCTGTTGTAG ACACTGCCGG ATCTTTCGAT GCATCTTTCA ATGCATCTTT    5340

CGATTTGTGT ATTTGCTGAT TCAAATGGTC TAGGTCTTCT AACGCCTTAT TTACCATTGC    5400

TTCATCATTT TTATCATCTT TTTCTCCATA TTTTGTTGTA GCCGTTTGTG ACATATCATT    5460

TTTCATTGCA TTAAGATCGT CCTCGCCACT TGTTGACCC  CTATCAACAT TGAAGAAAC    5520

CTCATTTAAA TCTTTAAGCA ATTGATCTAA TTTACTGTCT ATATCACTTT GACCGTTCAT    5580

TTCAGTGTGA GAACTTTTAT TTTCTTTGCT ATCCAACTCA TTAGCTCGTT TATGATTTC     5640

ATCTATTTGC GATGCTGTTT TCGCTTCATT TAGTTGTGCT TTATAATGTG CTTTAGATGA    5700

AGCCGATAAC TGTTTTAATT GCTCAATTTG ACGAATTGCT TTGTCAACTT TGTCTAATAA    5760

ATCTTGCTTA GATAATATCT CTTTTGAAAT TCAGTATCC  TTTTCAGATG CAGCTTGGGC    5820

ATCGTACGGC AAGATATTCG TTAAATGAT  ACTTGACGCC ATCATTGTCG AACACGATAA    5880

CTTTACATAT AATTGAAACG GTTTCCCTCG ATATTTAGCC ATCAACATAC TCCTTTCTCA    5940

CTTACTTCCT TCAAAGAATT ACATACTATT ATATACCTGT TTACAAGAAA TTTACACTTA    6000

TCTATCTAGT TATTGTTGTT AGTAATTATC AACTTATTAC TTAGCTTATA TTTAAGTAAA    6060

CAAAAAAGCA TGACGTAATA TCATATTGTC CATGTCGCTA ACATCATATT ACGTCAAATC    6120

TTTTAAATTA AATGATGCTT TATTTTAGAC TGCTTTTTCT TTTTAGCTTT CGAGCGCCTG    6180

TTTAAAAACT TGCTCGAATT GTTCACGCGA GATTTCGTGT GCATGTGCTT TTTGTGCTAA    6240
```

```
TAAAGCATCT CGAAACTGTT GTTGATCTTT CAAACTTTCT AACATTTGTA TTAATTGGTC    6300
TTTACTTTCC ATTGTTATCT CATCATTATG CTCAAATAAG TGCTCTGATA ATGTTACTTT    6360
AGCATGGTGT GCGGTTTGAC GATAACCTAA AATCAACAAC TCATAGTCAA ACGCTTGTTC    6420
CACCGCATTT AAAATTTCAT TACCCTCATT GATATCAAGA TAAATATCAC ATAACTGGTA    6480
TAGTTCATTT ACCCTGTCAA TATAATGAT  GGTATAAGTG CACATTAGCA TATTGATCAA    6540
GTTGCATTAG CTTATCAGAC ATCTCTGTAA TAGCAGCGAT GTGAAAATTA AAATCTGGTA    6600
AAGTTTCAAC CAATACCTTG ATGTTACGAA GTTGATCCGA GTTAGTTAAT ATTACAATTT    6660
CTTTAGTATA TCTATTACGA CTACGATAGT TATATAGATA TCCGCCTTGT AAAATACGAG    6720
ATTGAACCTT TGCGTCTGCT ATATTGAGCA TCGTTTCATA TTCGTTTTTA TCTGGAATAA    6780
TAATATTACA ATGTCGTTTC ATATCACCTT TACACATCAA TTGCATATTT CCCGGGACAT    6840
TACCATTACA GTGTTCTTGC CATACCAAAA CATCACTACC TTTTGATGGC AAATTATATA    6900
ACACTGAAAA TGGTAGGGCT AGTGAGTTAA TAACGAAATG ATGTTCCGTA ATTTCAAGTT    6960
GCTTGATAAA AAATAATACG AATGCAGCT  TTGAAGGGAA AAAGTAAGAC TTCCCTTGCC    7020
AATCCAATAT GACATCAGAT GTTACAAAAT TTTCATAAAT CACTTCTTTA CCTTCTGCTG    7080
TCATATATTT CTTCAAGATC GCTTTACGAT TTAAATCGTA ACAGTTGTG  CAATTTAATA    7140
CCATTCTTAG AATAATAATC GACAAATCGG ACACGTTGTT GGTCATCAAA CCATTCGACA    7200
CGACTAACAA TTCTAGGGCG CTCTCCACTT TGATAAAATA TTTTGCCTCG TAGACGTCCC    7260
ATATCATTAA TTGTAGCCGA ATTGTTGTTA CCTTTAATTT CCCAAAAAGC TGGTACAGTA    7320
ACCTGATTAA AAAATCGTGG TTTCATATTT TCTGTATTAT GATTATCTGC AAAAAATTGA    7380
TACGGTGATA TAACATCGTC CGGTAAAAAG CCATTGTCAT TGAGTACAAT TGTTAAATCT    7440
TCTTCCAACT TACTGGCTTT AAAAGACTCA TATAACTTTC GTGAATGATC GTTAAAGTAA    7500
TCAAATAATT TAATCATGTA GCACCTCTTG AACTAATGTT TCCCATTTTA AAATAATATC    7560
TTGAGTCATA AATTGCTGTG CCACTTCATA AGAGATGTCA TGTGGTGCCT GGGGACCATT    7620
GTTAAAATAC ATTACAATGG CATGAGCTAG TTTTGCGATA ACATCATCCA CACTATCTTC    7680
GTCGGTATCA AAAGGTACCA AGTAGCCATT TTCCCCATCT CGAATAAAGG TTGGGTTACC    7740
ATAATTCACA TTTAATCCAA TCATACCTAG TCCTGAGCCT ACCGCTTCCA TTAGTGTTAA    7800
CCCAAAACCT TCGCTAGTTG ATGCAGAAAG AAATAACTCA TAATCATTAT AAATTTCATC    7860
AAGTTTAACA TGCCCTTAGT AAACCGAATA TAATCTTGTG CGCGGTGTGT ATCAATAATT    7920
TTACGCAGTC GCGTCTTCTC GCTACCTTCT CCATAAATAT CAAATGTTAA TTCTGGCACT    7980
TGTCGTTTAG CCACGATAAC CGCCTTGACA AGCCAATCAA TATGTTTCTC ATTTGCTAAA    8040
CGAGATGCAC TAATCATCGC ATATGGCTTT CTTGATAATT TAGGATATGA TAACGCATCA    8100
ATGCTTCCCA CCGGDATAGT ATAGACACGT GGACGATAAC CTTGATATTG CTCAAATTGT    8160
CGACAAACCA TATGATTTTG AATATCTGTT GCTGTAATAA AGAAATCAAT GTATTTAGCT    8220
TTTGAAAATT GATATTCATA ATAATTGTTC CATAGTATAT GCTGCTCGCT CATCATATTA    8280
TTACTATAAT GATCAGCATG AATCACAACA CCAACTTTAC TATCACCTTT ATGCTGCAAA    8340
ACAGCCTGAC CAATATCAGA AGCGCGGTCT AATATGACAA TATCGTCTCG GGTTAAATTC    8400
AATCGTTGTA AAAAGTATGC AATAAATTCC GTTTTGTTAT ACAACACCGC ATCTTCAAAC    8460
ACATATATAG AGCTGTCTCC ATCAATATAT TCGTTATAAG CGATGGAACC ATCTTCATTA    8520
TAGAATTGTC GCATATATAA TTTCGCTTTA TTATCAGCTG GTGCATAATA CTCAGAAAAT    8580
ATACGCGTAT AACTATAAAA ATCTTTACGT ACTAACATAC TATTAATTAC AATTCTGCAC    8640
```

| | | | | | | |
|---|---|---|---|---|---|---|
| GATCCACAAC | ATCTTTTTGT | TCATTTTGTA | GATAACATGT | TACAAATGAT | GATTTCCCAT | 8700 |
| TAAAATATAG | ACGGACTATC | TTACCATTTC | TTTCTCTAAA | ACTAATTTCA | TGACCAAGCT | 8760 |
| CACGTTCAAT | GTCATCTAAC | GTGTACGTTG | TTGGTGCTAT | AGAAATATCA | CTAAAAATAC | 8820 |
| TGATACAACC | AAATAACTTC | TTGATCTTTA | AACCCAATGT | TTTGCGTTAA | TGTCTGTATG | 8880 |
| TTCTCTGACT | GTATAAAATC | TAAAAACACA | AATTTAGTGT | CTTGATTTGT | ACGTCTCAAT | 8940 |
| AATTTAGCAC | GGTAAGCTT | | | | | 8959 |

(2) INFORMATION FOR SEQ ID NO:2:

(i) SEQUENCE CHARACTERISTICS:
        (A) LENGTH: 10207 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Staphylococcus aureus
        (B) STRAIN: Clinical Isolate SA-24

(xi) SEQUENCE DESCRIPTION: SEQ ID NO:2:

| | | | | | | |
|---|---|---|---|---|---|---|
| AAGCTTATGG | ACCTATTTTA | GGTATATTGA | TTAGTTGGCT | TGGATTAATT | TCTGGAACAT | 60 |
| TTACAGTCTA | TTTGATCTGT | AAACGATTGG | TGAACACTGA | GAGGATGCAG | CGAATTAAAC | 120 |
| AACGTACTGC | TGTTCAACGC | TTGATTAGTT | TTATTGATCG | CCAAGGATTA | ATCCCATTGT | 180 |
| TTATTTTACT | TTGTTTTCCT | TTTACGCCAA | ATACATTAAT | AAATTTTGTA | GCGAGTCTAT | 240 |
| CTCATATTAG | ACCTAAATAT | TATTTCATTG | TTTTGGCATC | ATCAAAGTTA | GTTTCAACAA | 300 |
| TTATTTTAGG | TTATTTAGGT | AAGGAAATTA | CTACAATTTT | AACGCATCCT | TTAAGAGGGA | 360 |
| TATTAATGTT | AGTTGTGTTG | GTTGTATTTT | GGATTGTTGG | AAAAAAGTTA | GAACAGCATT | 420 |
| TTATGGGATC | GAAAAAGGAG | TGACATCGTG | AAAAAAGTTG | TAAAATATTT | GATTTCATTG | 480 |
| ATACTTGCTA | TTATCATTGT | ACTGTTCGTA | CAAACTTTTG | TAATAGTTGG | TCATGTCATT | 540 |
| CCGAATAATG | ATATGTCACC | AACCCTTAAC | AAAGGGACGT | GTTATTGTAA | ATAAAATTAA | 600 |
| AGTTACATTT | AATCAATTGA | ATAATGGTGA | TATCATTACA | TATAGGCGTG | GTAACGAGAT | 660 |
| ATATACTAGT | CGAATTATTG | CCAAACCTGG | TCAATCAATG | GCGTTTCGTC | AGGGACAATT | 720 |
| ATACCGTGAT | GACCGACCGG | TTGACGCATC | TTATGCCAAG | AACAGAAAAA | TTAAAGATTT | 780 |
| TAGTTTGCGC | AATTTTAAAG | AATTAGATGG | AGATATTATA | CCGCCTAACA | ATTTTGTTGT | 840 |
| GCTAAATGAT | CATGATAACA | ATCAGCATGA | TTCTAGACAA | TTTGGTTTAA | TTGATAAAAA | 900 |
| GGATATTATT | GGTAATATAA | GTTTGAGATA | TTATCCTTTT | TCAAAATGGA | CGATTCAGTT | 960 |
| CAAATCTTAA | AAAGAGGTGT | CAAAATTGAA | AAAGAATTA | TTGGAATGGA | TTATTTCAAT | 1020 |
| TGCAGTCGCT | TTTGTCATTT | TATTTATAGT | AGGTAAATTT | ATTGTTACAC | CATATACAAT | 1080 |
| TAAAGGTGAA | TCAATGGATC | CAACTTTGAA | AGATGGCGAG | CGAGTAGCTG | TAAACATTAT | 1140 |
| TGGATATAAA | ACAGGTGGTT | TGGAAAAAGG | TAATGTAGTT | GTCTTCCATG | CAAACAAAAA | 1200 |
| TGATGACTAT | GTTAAACGTG | TCATCGGTGT | TCCTGGTGAT | AAAGTAGAAT | ATAAAAATGA | 1260 |
| TACATTATAT | GTCAATGGTA | AAAAACAAGA | TGAACCATAT | TTAAACTATA | ATTTAAAACA | 1320 |
| TAAACAAGGT | GATTACATTA | CTGGGACTTT | CCAAGTTAAA | GATTACCGA | ATGCGAATCC | 1380 |
| TAAATCAAAT | GTCATTCCAA | AAGGTAAATA | TTTAGTTCTT | GGAGATAATC | GTGAAGTAAG | 1440 |
| TAAAGATAGC | CGTGCGTTTG | GCCTCATTGA | TGAAGACCAA | ATTGTTGGTA | AAGTTTCATT | 1500 |

| | | | | | | |
|---|---|---|---|---|---|---|
| TAGATTCTGG | CCATTTAGTG | AATTTAAACA | TAATTTCAAT | CCTGAAAATA | CTAAAAATTA | 1560 |
| ATATGAAACA | AATACAACAT | CGTTTGTCGG | TTTTAATACT | GATAAACGAT | GTTTTATTTT | 1620 |
| GTTAGTACCA | CAATAAAAGC | TAAGTTCGAA | ATGAACTTAT | AATAAATCAA | TCACAATCAC | 1680 |
| TTTGTGTTAA | AATATGTGTC | AAAGGAAGTG | AGGGTTTGTC | ATGACATTAC | ATGCTTATTT | 1740 |
| AGGTAGAGCG | GGAACAGGTA | AGTCTACGAA | AATGTTGACC | GAAATAAAAC | AAAAAATGAA | 1800 |
| AGCAGATCCG | CTTGGAGATC | CAATCATTTT | AATTGCGCCA | ACTCAAAGTA | CATTTCAATT | 1860 |
| AGAACAAGCC | TTTGTCAATG | ATCCGGAATT | AAATGGTAGT | TTAAGAACAG | AAGTGTTGCA | 1920 |
| TTTTGAACGA | TTAAGTCATC | GTATTTTCCA | AGAAGTTGGT | AGTTATAGCG | AACAAAGTT | 1980 |
| ATCTAAAGCT | GCAACGGAAA | TGATGATTTA | TAACATTGTT | CAAGAACAAC | AAAAGTATTT | 2040 |
| AAACTTTAT | CAATCACAAG | CAAATATTA | TGGGTTTAGT | GAAAAATTAA | CAGAACAAAT | 2100 |
| TCAAGATTTT | AAAAAATATG | CAGTAACGCC | TGAACATTTA | GAACACTTTA | TTGCTGATAA | 2160 |
| AAATATGCAA | ACTCGAACTA | AAAATAAGTT | AGAGGATATT | GCTTTAATAT | ACCGTGAGTT | 2220 |
| CGAACAACGC | ATTCAAAACG | AGTTTATTAC | TGGTGAGGAT | TCATTACAAT | ATTTTATTGA | 2280 |
| TTGTATGCCG | AAATCAGAGT | GGCTAAAACG | TGCTGATATA | TATATTGATG | GTTTTCACAA | 2340 |
| CTTTTCAACG | ATTGAGTATT | TAATAATCAA | AGGATTAATT | AAATATGCGA | GAGTGTCACA | 2400 |
| ATTATATTGA | CGACAGATGG | TAACCACGAT | CAATTTAGTT | TTTTAGAAAA | CCATCGGAAG | 2460 |
| TGTTACGACA | TATTGAAGAA | ATAGCAAATG | AACTCAATAT | TTCTATTGAA | CGTCAATATT | 2520 |
| TCAACCAATT | ATATCGCTTC | AATAATCAAG | ATTAAAGCA | TCTTGAACAA | GAATTTGATG | 2580 |
| TACTTCAAAT | CAATCGAGTG | GCATGTCAAG | GTCATATCAA | TATTTTAGAA | TCTGCGACTA | 2640 |
| TGAGAGAGGA | AATAAATGAA | ATTGCGCGAC | GTATCATCGT | TGATATTCGT | GATAAGCAAT | 2700 |
| TACGATATCA | AGATATTGCA | ATTTTATATC | GTGACGAGTC | TTATGCTTAT | TTATTTGATT | 2760 |
| CCATATTACC | GCTTTATAAT | ATTCCTTATA | ACATTGATAC | AAAGCGTTCG | ATGACACATC | 2820 |
| ATCCGGTCAT | GGAAATGATT | CGTTCATTGA | TTGAAGTTAT | TCAATCTAAT | TGGCAAGTGA | 2880 |
| ATCCAATGCT | ACGCTTATTG | AAGACTGATG | TGTTAACGGC | ATCATATCTA | AAAAGTGCAT | 2940 |
| ACTTAGTTGA | TTTACTTGAA | AATTTTGTAC | TTGAACGTGG | TATATACGGT | AAACGTTGGT | 3000 |
| TAGATGATGA | GCTATTTAAT | GTCGAACATT | TTAGCAAAAT | GGGGCGTAAA | GCGCATAAAC | 3060 |
| TGACCGAAGA | TGAACGTAAC | ACATTTGAAC | AAGTCGTTAA | GTTAAAGAAA | GATGTCATTG | 3120 |
| ATAAATTTT | ACATTTGAA | AAGCAAATGT | CACAAGCGGA | AACTGTAAAA | GACTTTGCAA | 3180 |
| CTGCTTTTTA | TGAAAGTATG | GAATATTTCG | AACTGCCAAA | TCAATTGATG | ACAGAGCGAG | 3240 |
| ATGAACTTGA | TTTAAATGGT | AATCATGAAA | AGGCGGAGGA | AATTGATCAA | ATATGGAATG | 3300 |
| GCTTAATTCA | AATCCTTGAC | GACTTAGTTC | TAGTATTTGG | AGATGAACCA | ATGTCGATGG | 3360 |
| AACGTTTCTT | AGAAGTATTT | GATATTGGTT | TAGAACAATT | AGAATTTGTC | ATGATTCCAC | 3420 |
| AAACATTAGA | TCAAGTTAGT | ATTGGTACGA | TGGATTTGGC | TAAAGTCGAC | AATAAGCAAC | 3480 |
| ATGTTTACTT | AGTTGGAATG | AACGACGGCA | CCATGCCACA | ACCAGTAACT | GCATCAAGTT | 3540 |
| TAATTACTGA | TGAAGAAAAG | AAATATTTTG | AACAACAAGC | AAATGTAGAG | TTGAGTCCTA | 3600 |
| CATCAGATAT | TTTACAGATG | GATGAAGCAT | TTGTTTGCTA | TGTTGCTATG | ACTAGAGCTA | 3660 |
| AGGGAGATGT | TACATTTTCT | TACAGTCTAA | TGGGATCAAG | TGGTGATGAT | AAGGAGATCA | 3720 |
| GCCCATTTTT | AAATCAAATT | CAATCATTGT | TCAACCAATT | GGAAATTACT | AACATTCCTC | 3780 |
| AATACCATGA | AGTTAACCCA | TTGTCACTAA | TGCAACATGC | TAAGCAAACC | AAAATTACAT | 3840 |
| TATTTGAAGC | ATTGCGTGCT | TGGTTAGATG | ATGAAATTGT | GGCTGATAGT | TGGTTAGATG | 3900 |

| | | | | | | |
|---|---|---|---|---|---|---|
| CTTATCAAGT | AATTAGAGAT | AGCGATCATT | TAAATCAAGG | TTTAGATTAT | TTAATGTCAG | 3960 |
| CATTAACGTT | TGACAATGAA | ACTGTAAAAT | TAGGTGAAAC | GTTGTCTAAA | GATTTATATG | 4020 |
| GTAAGGAAAT | CAATGCCAGT | GTATCTCGTT | TTGAAGGTTA | TCAACAATGC | CCATTTAAAC | 4080 |
| ACTATGCTTC | ACATGGTCTG | AAACTAAATG | AACGAACGAA | ATATGAACTT | CAAAACTTTG | 4140 |
| ATTTAGGTGA | TATTTTCCAT | TCCGTTTTAA | AATATATATC | TGAACGTATT | AATGGCGATT | 4200 |
| TTAAACAATT | AGACCTGAAA | AAAATAAGAC | AATTAACGAA | TGAAGCATTG | GAAGAAATTT | 4260 |
| TACCTAAAGT | TCAGTTTAAT | TTATTAAATT | CTTCAGCTTA | CTATCGTTAT | TTATCAAGAC | 4320 |
| GCATTGGCGC | TATTGTAGAA | ACAACACTAA | GCGCATTAAA | ATATCAAGGC | ACGTATTCAA | 4380 |
| AGTTTATGCC | AAAACATTTT | GAGACAAGTT | TTAGAAGGAA | ACCAAGAACC | AAATGTACGA | 4440 |
| ATTAATTGCA | CAAACATTAA | CGACAACTCA | AGGTATTCCA | ATTAATATTA | GAGGGCAAAT | 4500 |
| TGACCGTATC | GATACGTATA | CAAAGAATGA | TACAAGTTTT | GTTAATATCA | TTGACTATAA | 4560 |
| ATCCTCTGAA | GGTAGTGCGA | CACTTGATTT | AACGAAAGTA | TATTATGGTA | TGCAAATGCA | 4620 |
| AATGATGACA | TACATGGATA | TCGTTTTACA | AAATAAACAA | CGCCTTGGAT | TAACAGATAT | 4680 |
| TGTGAAACCA | GGTGGATTAT | TATACTTCCA | TGTACATGAA | CCTAGAATTA | AATTTAAATC | 4740 |
| ATGGTCTGAT | ATTGATGAAG | ATAAACTAGA | ACAAGATTTA | ATTAAAAAGT | TTAAGCTGAG | 4800 |
| TGGTTTAGTG | AATGCAGACC | AAACTGTTAT | TGATGCATTG | GATATTCGTT | TAGAACCTAA | 4860 |
| ATTCACTTCA | GATATTGTAC | CAGTTGGTTT | GAATAAAGAT | GGCTCTTTGA | GTAAACGAGG | 4920 |
| CAGCCAAGTG | GCAGATGAAG | CAACAATTTA | TAAATTCATT | CAGCATAACA | AAGAGAATTT | 4980 |
| TATAGAAACA | GCTTCAAATA | TTATGGATGG | ACATACTGAA | GTGCACCATT | AAAGTACAAA | 5040 |
| CAAAAATTGC | CATGTGCTTT | TTGTAGTTAT | CAATCGGTAT | GTCATGTAGA | TGGCATGATT | 5100 |
| GATAGTAAGC | GATATCGAAC | TGTAGATGAA | ACAATAAATC | CAATTGAAGC | AATTCAAAAT | 5160 |
| ATTAACATTA | ATGATGAATT | TGGGGGTGAG | TAATAGATGA | CAATTCCAGA | GAAACCACAA | 5220 |
| GGCGTGATTT | GGACTGACGC | GCAATGGCAA | AGTATTTACG | CAACTGGACA | AGATGTACTT | 5280 |
| GTTGCAGCCG | CGGCAGGTTC | AGGTAAAACA | GCTGTACTAG | TTGAGCGTAT | TATCCAAAAG | 5340 |
| ATTTTACGTG | ATGGCATTGA | TGTCGATCGA | CTTTTAGTCG | TAACGTTTAC | AAACTTAAGC | 5400 |
| GCACGTGAAA | TGAAGCATCG | TGTAGACCAA | CGTATTCAAG | AGGCATCGAT | TGCTGATCCT | 5460 |
| GCAAATGCAC | ACTTGAAAAA | CCAACGCATC | AAAATTCATC | AAGCACAAAT | ATCTACACTT | 5520 |
| CATAGTTTTT | GCTTGAAATT | AATTCAACAG | CATTATGATG | TATTAAATAT | TGACCCGAAC | 5580 |
| TTTAGAACAA | GCAGTGAAGC | TGAAAATATT | TTATTATTAG | AACAAACGAT | AGATGAGGTC | 5640 |
| ATAGAACAAC | ATTACGATAT | CCTTGATCCT | GCTTTTATTG | AATTAACAGA | ACAATTGTCT | 5700 |
| TCAGATAGAA | GTGATGATCA | GTTTCGAATG | ATTATTAAAC | AATTGTATTT | CTTTAGCGTT | 5760 |
| GCAAATCCAA | ATCCTACAAA | TTGGTTGGAT | CAATTGGTGA | CACCATACGA | AGAAGAAGCA | 5820 |
| CAACAAGCGC | AACTTATTCA | ACTACTAACA | GACTTATCTA | AAGTATTTAT | CACAGCTGCC | 5880 |
| TATGATGCTT | TAAATAAGGC | GTATGATTTG | TTTAGTATGA | TGGATGGCGT | CGATAAACAT | 5940 |
| TTAGCTGTTA | TAGAAGATGA | ACGACGTTTA | ATGGGGCGTG | TTTTAGAAGG | TGGTTTTATT | 6000 |
| GATATACCTT | ATTTAACTGA | TCACGAATTT | GGCGCGCGTT | TGCCTAATGT | AACAGCGAAA | 6060 |
| ATTAAAGAAG | CAAATGAAAT | GATGGTCGAT | GCCTTAGAAG | ATGCTAAACT | TCAGTATAAA | 6120 |
| AAATATAAAT | CATTAATTGA | TAAAGTGAAA | AATGATTACT | TTCAAGAGA | AGCTGATGAT | 6180 |
| TTGAAAGCTG | ATATGCAACA | ATTGGCGCCA | CGAGTAAAGT | ACCTTGCGCG | TATTGTGAAA | 6240 |
| GATGTTATGT | CAGAATTCAA | TCGAAAAAAG | CGTAGCAAAA | ATATTCTGGA | TTTTTCTGAT | 6300 |

-continued

| | | | | | | |
|---|---|---|---|---|---|---|
|TATGAACAAT|TTGCATTACA|AATTTTAACT|AATGAGGATG|GTTCGCCTTC|AGAAATTGCC|6360|
|GAATCATACC|GTCAACACTT|TCAAGAAATA|TTGGTCGATG|AGTATCAAGA|TACGAACCGG|6420|
|GTTCAAGAGA|AAATACTATC|TTGCATCAAA|ACGGGTGATG|AACATAATGG|TAATTTATTT|6480|
|ATGGTTGGAG|ATGTTAAGCA|ATCCATTTAT|AAATTTAGAC|AAGCTGATCC|AAGTTTATTT|6540|
|ATTGAAAAGT|ATCAACGCTT|TACTATAGAT|GGAGATGGCA|CTGGACGTCG|AATTGATTTG|6600|
|TCGCAAAACT|CCGTTCTCGA|AAAGAAGTAC|TGTCAACGAC|TAACTATATA|TCAAACATAT|6660|
|GATGGATGAA|CAAGTCGGTG|AAGTAAAATA|TGATGAAGCG|GCACAGTTGT|ATTATGGTGC|6720|
|ACCATATGAT|GAATCGGACC|ATCCAGTAAA|CTTAAAAGTG|CTTGTTGAAG|CGGATCAAGA|6780|
|ACATAGTGAT|TTAACTGGTA|GTGAACAAGA|AGCGCATTTT|ATAGTAGAAC|AAGTTAAAGA|6840|
|TATCTTAGAA|CATCAAAAAG|TTTATGATAT|GAAAACAGGA|AGCTATAGAA|GTGCGACATA|6900|
|CAAAGATATC|GTTATTCTAG|AACGCAGCTT|TGGACAAGCT|CGCAATTTAC|AACAAGCCTT|6960|
|TAAAAATGAA|GATATTCCAT|TCCATGTGAA|TAGTCGTGAA|GGTTACTTTG|AACAAACAGA|7020|
|AGTCCGCTTA|GTATTATCAT|TTTAAGAGC|GATAGATAAT|CCATTACAAG|ATATTTATTT|7080|
|AGTTGGGTTA|ATGCGCTCCG|TTATATATCA|GTTCAAAGAA|GACGAATTAG|CTCAAATTAG|7140|
|AATATTGAGT|CAAATGATGA|CTACTTCTAT|CAATCGATTG|TAAATTACAT|TAATGACGAA|7200|
|GCAGCAGATG|CTATTTAGT|TGATAAATTA|AAAATGTTTT|TATCAGATAT|TCAAAGTTAC|7260|
|CAACAATATA|GTAAAGATCA|TCCGGTGTAT|CAGTTAATTG|ATAAATTTTA|TAATGATCAT|7320|
|TATGTTATTC|AATACTTTAG|TGGACTTATT|GGTGGACGTG|GACGACGTGC|AAACCTTTAT|7380|
|GGTTTATTTA|ATAAAGCTAT|CGAGTTTGAG|AATTCAAGTT|TTAGAGGTTT|ATATCAATTT|7440|
|ATTCGTTTTA|TCGATGAATT|GATTGAAAGA|GGCAAAGATT|TTGGTGAGGA|AAATGTAGTT|7500|
|GGTCCAAACG|ATAATGTTGT|TAGAATGATG|ACAATTCATA|GTAGTAAAGG|TCTAGAGTTT|7560|
|CCATTTGTCA|TTTATTCTGG|ATTGTCAAAA|GATTTTAATA|AACGTGATTT|GAAACAACCA|7620|
|GTTATTTTAA|ATCAGCAATT|TGGTCTCGGA|ATGGATTATT|TTGATGTGGA|TAAAGAAATG|7680|
|GCATTTCCAT|CTTTAGCTTC|GGTTGCATAT|AAAGCTGTTG|CCGAAAAAGA|ACTTGTGTCA|7740|
|GAAGAAATGC|GATTAGTCTA|TGTAGCATTA|ACAAGAGCGA|AAGAACAACT|TTATTTAATT|7800|
|GGTAGAGTGA|AAAATTGATA|AATCGTTACT|AGAACTAGAG|CAATTGTCTA|TTTCTGGTGA|7860|
|GCACATTGCT|GTCAATGAAC|GATTAACTTC|ACCAAATCCG|TTCCATCTTA|TTTATAGTAT|7920|
|TTTATCTAAA|CATCAATCTG|CGTCAATTCC|AGATGATTTA|AAATTTGAAA|AAGATATAGC|7980|
|ACAAGTTGAA|GATAGTAGTC|GTCCGAATGT|AAATATTTCA|ATTATATACT|TGAAGATGT|8040|
|GTCTACAGAA|ACCATTTAG|ATAATAATGA|ATATCGTTCG|GTTAATCAAT|TAGAAACTAT|8100|
|GCAAAATGGT|AATGAGGATG|TTAAAGCACA|AATTAAACAC|CAACTTGATT|ATCAATATCC|8160|
|ATATGTAAAT|GATACTAAAA|AGCCATCCAA|AACAATCTGT|TTCTGAATTG|AAAAGGCAAT|8220|
|ATGAAAGAAG|AAAGTGGCAC|AAGTTACGAA|CGAGTAAGAC|AATATCGTAT|CGGTTTTCAA|8280|
|CGTATGAACG|ACCTAAATTT|CTAAGTGAAC|AAGGTAAACG|AAAAAGCGAA|TTGAAATTGG|8340|
|TACGTTAATG|CATACAGTGA|TGCAACATTT|ACCATTCAAA|AAGAACGCA|TATCTGAAGT|8400|
|TGAGTTACAT|CAGTATATCG|ATGGATTAAT|CGATAAACAT|ATTATCGAAG|CAGATGCGAA|8460|
|AAAAGATATC|CGTATGGATG|AAATAATGAC|ATTATCAATA|GTGAGTATAT|TCGATTATTG|8520|
|CTGAAGCAGA|GCAAGTTTAT|CGTGAATTAC|CGTTTGTAGT|TAACCAAGCA|TTAGTTGACC|8580|
|AATTGCCACA|AGGAGACGAA|GACGTCTCAA|TTATTCAAGG|TATGATTGAC|TTAATCTTTG|8640|
|TTAAAGATGG|TGTGCATTAT|TTTGTAGACT|ATAAAACCGA|TGCATTTAAT|CGTCGCCGTG|8700|

| | | | | | | |
|---|---|---|---|---|---|---|
| GGATGACAGA | TGAAGAAATT | GGTACACAAT | TAAAAAATAA | ATATAAGATA | CAGATGAAAT | 8760 |
| ATTATCAAAA | TACGCTTCAA | ACGATACTTA | ATAAAGAAGT | TAAAGGTTAT | TTATACTTCT | 8820 |
| TCAAATTTGG | TACATTGCAA | CTGTAGTATT | TTGATTTTCA | AAAGAATAAA | AATAATTTC | 8880 |
| GATTAAGTGC | AAAGTCCTTG | TAGCAGAATG | AACACAACTC | ATTTTCAAAA | TTGTCTTACT | 8940 |
| TATTTATTTG | TTATTTGATA | ACGAAAAAAG | TTATAATGTG | AATTAAGATA | AAGATGAGGA | 9000 |
| GTTGAGAATG | AATGAAATTC | TTATCATTCA | AGTATAATGA | CAAAACTTCA | TATGGCGTTA | 9060 |
| AAGTAAAACG | CGAAGATGCT | GTATGGGATT | TAACACAAGT | ATTTGCTGAC | TTTGCAGAAG | 9120 |
| GAGATTTCCA | TCCTAAAACA | TTGTTAGCTG | GTTACAACA | AAATCATACT | TTAGATTTTC | 9180 |
| AAGAACAAGT | ACGTAAAGCA | GTTGTAGCAG | CAGAAGATAG | CGGCAAAGCT | GAAGACTATA | 9240 |
| AAATTTCATT | TAATGACATT | GAATTCTTAC | CACCAGTAAC | ACCTCCGAAT | AATGTGATTG | 9300 |
| CTTTTGGTAG | AAATTACAAA | GATCATGCGA | ACGAATTAAA | TCATGAAGTA | GAAAAATTAT | 9360 |
| ATGTATTTAC | AAAAGCAGCG | TCATCTTTAA | CAGGAGATAA | TGCAACAATT | CCAAATCATA | 9420 |
| AAGATATTAC | TGATCAATTA | GATTATGAAG | GTGAATTAGG | TATTGTTATT | GGTAAGTCTG | 9480 |
| GTGAAAAGAT | TCCAAAAGCA | TTAGCTTTAG | ATTATGTTTA | CGGCTATACA | ATTATTAACG | 9540 |
| ATATCACTGA | TCGCAAAGCA | CAAAGTGAAC | AAGATCAAGC | ATTTTTATCA | AAAAGTTTAA | 9600 |
| CTGGCGGTTG | CCCAATGGGT | CCTTATATCG | TTACTAAAGA | CGAACTACCA | TTACCTGAAA | 9660 |
| ATGTAAATAT | TGTTACAAAA | GTTAACAATG | AAATTAGACA | AGATGGTAAC | ACTGGCGAAA | 9720 |
| TGATTCTTAA | AATTGATGAA | TTAATAGAAG | AAATTTCAAA | ATATGTTGCA | CTACTACCGG | 9780 |
| GAGATTATTA | TTGCAACTGG | TACACCAGCT | GGCGTTGGTG | CAGGTATGCA | ACCACCTAAA | 9840 |
| TTTTACAAC | CAGGTGATGA | AGTTAAAGTG | ACTATTGATA | ATATTGGAAC | GCTGACAACT | 9900 |
| TATATCGCTA | AATAATTATC | ATTTAAAAAG | CTAACCAGGT | CTTTATATAG | ATTGGTTAGT | 9960 |
| TTTTTCTTGC | TTTTCTAAAA | AGGTGTTAAA | GATAAATTAT | TTATAATGTT | ACCATTTTGA | 10020 |
| GATGAAAGTG | AAATATTGAT | ATTAAGAAGT | AGTTGATTAT | TTTACAGCAG | ATTCACAATA | 10080 |
| TTCTAATAAG | GGCAATGCAA | ATGTCATGTT | CTTCCTCTCA | AATATAGAAG | TGTGGTAGAA | 10140 |
| TATATATTCG | TGTATAATCA | AATCTAGATT | AAATTACAAG | CAAGTGGGTA | TTAATCCCAA | 10200 |
| GAAGCTT | | | | | | 10207 |

( 2 ) INFORMATION FOR SEQ ID NO:3:

( i ) SEQUENCE CHARACTERISTICS:
        ( A ) LENGTH: 2082 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Staphylococcus aureus
        ( B ) STRAIN: Clinical Isolate SA- 36

( x i ) SEQUENCE DESCRIPTION: SEQ ID NO:3:

| | | | | | | |
|---|---|---|---|---|---|---|
| AAGCTTTCTA | ATCTATCGTT | AATGATTTGC | TTTAAAATTG | GGTCGAAGTT | AATTGAAGGT | 60 |
| GTGAAGTGTA | TATCTGTATT | AATAACCATG | TCATTCATTT | GCTGCTTCAC | TTTGTTAACA | 120 |
| AGTCTTCCGT | CATATAAAAA | TAATGGTACG | ACAATCAATT | TTTGATACCG | TTTCGAGATG | 180 |
| CTTTCTAAAT | CATGTGTAAA | ACTAATCTCT | CCATATAGCG | TTCTCGCATA | AGTAGGTTTA | 240 |
| TTAATCTGCA | AATGTTGAGC | GCATATTTGT | AACTCTTCGT | GTGCCTTAGT | AAAATTTCCA | 300 |
| TTAATATTGC | CGTGTGCAAC | AACCATAACT | CCAACTTGTT | GTTCGTCACC | TGCTAATGCG | 360 |

```
TCACAAATAC  GTTGTTCAAT  TAATCGTCTC  ATTAAAGGAT  GTGTGCCAAG  TGGCTCGCTT        420

ACTTCTACCT  TTATGTCTGG  ATACCGTCGT  TTCATTTCAT  GAACGATATT  CGGTATATCC        480

TTGAGATAAT  GCATTGCACT  AAAGATTAGC  AATGGTACAA  TTTTAAAATG  GTCAACCCCA        540

CTTTGAATCA  ACGTCGTCAT  TACCGTCTCT  AAATCCTGAT  GCTCACTTTC  TAAAAACGCA        600

ATATCATAGT  GATGTATATC  ATCTTTTACT  AATTCAGAAA  TAAATGCTTC  TAACGCTTGA        660

TTCTGTCGTC  CGTGCCTCAT  GCCATGTGCA  ACAATGATAT  TCCCATTCAC  ATTTACCAAC        720

CCTTTCACAC  GTATTGTATA  CCAAATCATT  TTGTTTTGT   GAAAGAATC   ACATTATAAT       780

GTAAAATCAG  GGAATTCCCT  GATGCCTGTA  GTCATGCATA  TTCCTTATAC  ATTTTCCCTT       840

TTTGTTAAAT  CAAAAAAGC   GACCGATATA  TGAATCCCTA  CTCAACATTT  ATTTGAGCAA        900

GCATCAATAT  ATCGGTCGCT  TGTAGTGTAT  ATTATTATCT  TAAAATGGTG  GTTGGCCTAA        960

TATTGTTTCG  TCAAAGCGCT  CGGGTATCAA  TACTTTGCGC  ATGATCACAC  CTAAATCGCC      1020

ATCATCATTT  TCATGTTCGC  TGTATATTTC  ATAACCTCTT  TTTTCATAAA  TTTTAAGTAA     1080

CCACGGATGC  AATCTTGCAG  ATGTACCTAA  AGTAACTGCC  GCTGACTTTA  ACGTATCTCG    1140

CAAAAATGCT  CTTCAACATA  AGTAAGTAAT  TGGCTACCAT  AGCCTTTCCC  TTCATACTCA    1200

GGATTTGTCG  CAAACCACCA  GACAAAAGGA  TAGCCCGAAA  TACTTTCAC   ACTTCCCAA     1260

GGATATCTAA  CCGTAATCGT  AGATATAATT  TCATCATCAA  TTGTCATGAC  AAATGTAGTA   1320

TTTTTATCTA  TATTTTCTTT  AACAGCATCT  AAATTAGCAT  TAACTGAAGG  CCAATCAATA   1380

CCTAGTTCTC  TTAGAGGCGT  AAATGCTTCA  TGCATGAGTT  GTTGCAATTT  TTCTGCATCT    1440

TGTTCACTTG  CGAGTCGAAT  CATCGTTTTT  GTCATATTAA  TCCCCACTCT  TTTTTAAATG  1500

ATTTAACCAT  ATTTATTTT   TAAAATAAAT  ATCCATCAAA  GTGTATCAAT  AAATTTATCA   1560

CATGTCAGAA  AGTATGCTTC  ATCTGAATAC  ACCAATACTC  TCATGAAACT  TATTAAAAAT   1620

TACTCTCTCA  ACGTAAAAAA  ACCATTCAAA  TTCATGAATG  GTTTGGAAGA  ATGATTCATT   1680

GTTACGCTAT  TTAATCACTA  CATCTTAATT  ATTGTTGCTC  TAAACGATTA  CGCTTACCAT   1740

TTAAGAAAGC  ATAAACGAGA  CCTACAAAAA  TACCGCCACC  GACAAAGTTA  CCTAAGAAAG  1800

CAAAAACGAT  ATTTTTTAAA  ACATGTAACC  ATGAAACTGC  ATCAAGGTTA  AAGAATACCA  1860

TACCTGCATA  TAGACCTGCA  TTGAACACAA  CGTGCTCATA  TCCCATGTAT  ACAAAGACCA  1920

CGACACCACA  AGCTATGAAG  AATGCCTTTG  TTAAGCCGCC  TTTGAATTGC  ATAGAGATGA  1980

AAATACCAAT  ATTAATAAAG  AAGTTACAGA  AAATACCTTT  TGTAAAAATA  TTCAACCATG  2040

TTGAATCAAC  AGTCTTTTTC  TGAACTAAAG  CTGTTAAAGC  TT                          2082
```

( 2 ) INFORMATION FOR SEQ ID NO:4:

( i ) SEQUENCE CHARACTERISTICS:
        ( A ) LENGTH: 2885 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Staphylococcus aureus
        ( B ) STRAIN: Clinical Isolate SA- 77

( x i ) SEQUENCE DESCRIPTION: SEQ ID NO:4:

```
AAGCTTTTGA  TTAATTTGGG  CTTTAAAGTA  TTCCCAATTA  TAATTCTTCA  TGATTTTCTT          60

ATTGGATTTC  GAATTTGGTT  TCATGCATTG  TTGCCTCAAA  GAACATGCTG  AACAGTCATC       120
```

-continued

| | | | | | | |
|---|---|---|---|---|---|---|
| GCATTCATAT | AGCTTGAAGT | CACGTTTAAA | ACCATATCTA | TCATTACGGT | ATGCATATCT | 180 |
| TTTAAAACCT | ATTCTTTTGT | TATTAGGACA | TATAAATTCA | TCATTAAGTT | CGTCATATTT | 240 |
| CCAATTTTGA | GTGTTAAAAA | TGTCACTTTT | AAACTTTCTA | GTTTATCTT | TAATAAACAT | 300 |
| GCCATACGTA | ATAAGTGGCG | TTTTATTAAA | ACATCTATAA | TAGCCATATA | GTTTTGCTCA | 360 |
| CTATCATAAC | TGCATCAGCT | ACATTAACTC | TGGTAATACC | GAGGATTTGA | ATCATTGTTA | 420 |
| AAAATGGAAT | TAAAGTTCTA | GTATCTGTTG | GGGTTTGAAA | TAGGTCATAG | GATAAAAAAA | 480 |
| TTGAGAATTT | GTCGCTATTT | GTAAATTGTA | TCCTGGCTTA | AGTTGGCCAT | TTTTCATATG | 540 |
| GTCTTCCTTC | ATTCTCATAA | AAGTTGCATC | ATGATCAGCC | CAGAAAGCTA | TTTCTATCTT | 600 |
| TAAGAATCCA | TTTTGTTCT | TCATATTTAT | TTTTCTTTC | GGAATAATCA | TCAAATTTCT | 660 |
| TTTTGAACTT | CTTAATCTCA | GTTCTTTTTT | ACGGGTCTGT | TTTCTAATTT | GAGCACTCTT | 720 |
| CGTTCTAAAT | AGAATGATTT | AAATCTTCGA | TTTCTTTTAT | CTAAATGACT | ACCAATTAAA | 780 |
| TCTATTTCTT | CTCGTGATTT | TGAATACTTT | TCTTCCACAC | AAATGTATAT | CTATTGGCAT | 840 |
| TAGCTTCTAC | TTATGTACCA | TCAATAAAAA | TTGAATTATT | ATCAATAAGA | TTTTGCTTTA | 900 |
| AACATTGACT | ATGGAACTGA | ATAAATAAAG | ATTCAATTAA | CGCATCAGTA | TTAGGATTCA | 960 |
| CTCTAAAACG | ATTAATAGTT | TTATAAGAAG | GTGTTTGATC | TTGAGCTAAC | CACATCATTC | 1020 |
| GAATACTGTC | ATGAAGTAAT | TTCTCTATTC | TACGACCAGA | AAATACAGAT | TGAGTATATG | 1080 |
| CATATAAGAT | GATTTTAAC | ATCATTTTG | GATGATAGGA | TGTTGCGCCA | CGATGATGTC | 1140 |
| TGAATTCATC | GAATTCGCTA | TCAGGTATCG | TTTCAACAAT | TTCATTACA | TATCGCGAAA | 1200 |
| TATCATTTTA | AGGAATTCTA | ACAGAAGTTT | CTATTGGTAG | TGTAAGTTGG | GCAAAGTGTC | 1260 |
| TTATTTTTT | AAAGTATGTA | AAAGTAAAAT | TACATGTTAA | TACGTAGTAT | TAATGGCGAG | 1320 |
| ACTCCTGAGG | GAGCAGTGCC | AGTCGAAGAC | CGAGGCTGAG | ACGGCACCCT | AGGAAAGCGA | 1380 |
| AGCATTCAAT | ACGAAGTATT | GTATAAATAG | AGAACAGCAG | TAAGATATTT | TCTAATTGAA | 1440 |
| AATTATCTTA | CTGCTGTTTT | TTTAGGGATT | TATGTCCCAG | CCTGTTTTAT | TTTCGACTAG | 1500 |
| TTTGGAGAAT | TTATTGACAT | TCACATTATT | TAAACGGCAA | CAAAGATTGT | TTTATTTTGA | 1560 |
| TAGGCATTAT | ATGGTGTTAA | AAAATTTGCA | TGAAAATTAA | AAAATGCTTC | GTTCAGGAAG | 1620 |
| GTGTCGTAAT | TTACCTATTT | GCTGAATGAA | GCATTTATT | TTTAAATATG | ATAGCCAATA | 1680 |
| TAACAAGCTA | TAAATCCAAT | GATGAATTGT | AAAAGTGAAT | AATTGAGAAA | AAGGTTAATA | 1740 |
| TCAAATTTTG | GTGTCATCAT | TAATGTAAGT | TCCTTGGCTA | ACGTTGAGAA | AGTTGTTAAG | 1800 |
| CCACCTAAAA | AAACCGGTGA | CAAAGAACGC | AGGGAACCAT | GAGATTGAAA | TTGATAGGCC | 1860 |
| TATAGTTAAT | CCAATTAAAA | AACTACCAAC | TAGATTTACT | ATCAATGTTG | CGATAGGTAA | 1920 |
| CTTTGAAGTA | AATTTATGAT | TAAAATAATC | AGTAATGGCA | CTTCTAGCAA | TTGCGCCAAA | 1980 |
| ACCGCCGCCA | ATCATGACTA | AAATGATTGA | TATCATGATA | AACCACCACC | TAGTTTTATA | 2040 |
| CCGACGTAAC | ATAACAAAAT | ACCAAAGACA | TAACTTGTTA | CAGCATATAG | TAGTAAAGTT | 2100 |
| ATAAATTGTT | GATGATCAAA | CATATGTATT | AATTCTAATT | GAAATGTTGA | AAAAGTCGTT | 2160 |
| AAAGCACCAA | GAAAACCAGT | CGTAATAGCT | TTTTTAGGG | TCGGATGGTT | TGAAAAAAAT | 2220 |
| GCAATTGTTA | AGGCTGTTAG | CAATCCCATT | ACAAAGGCAC | CAGTCAAATT | GGCTATCAGT | 2280 |
| GTTCCGATTG | GAAAACCTCC | GTCAGTATTC | AGAAAGAAA | TGAGGTAACG | TAATAAAGCG | 2340 |
| CCTAAAGCAC | CACCGATAAA | AATATATACA | TATTGCATTT | GGTTCACCTC | GAAAAGAAGT | 2400 |
| AGTTTGAATT | TAAAAAAGAG | GTTTTGGCAA | CACGACGACA | AAAATTGTCG | ATGCATTATC | 2460 |
| AAACCTCATT | ATATGTTATA | TCTTGTTGTA | TAACTATAGC | GATTAGATGC | ATAGTTATGA | 2520 |

| | | | | | |
|---|---|---|---|---|---|
| TTTCGAAAAT | CTAATATTTT | TTATACGCAA | CAACGTCATC | AAATTGTTTT | ACTCATTATA | 2580 |
| GCATGATACA | TTGTATTGTT | TTGTATTAAC | GCTACATTGA | CATTTTATCT | TTTTTAAATA | 2640 |
| AAACCGAATG | TACGACAATT | GAAAAGATAT | GTACTAAAAT | AACAATTAGA | ATAATCCAAG | 2700 |
| GCAAACTTTT | ACTCGCAATT | CTAATCCAAT | CTGCATCAGG | CTTTAGTGAT | TTAATTGAAC | 2760 |
| GATCTGCAAA | AATTATAGAC | AAAATTAGTA | CAATTGAGTT | AATAACACTG | CAGAAAGTA | 2820 |
| TTAATTTAAT | AAAAGAATTA | AAAAATCCAC | TTAGGAAAAC | GTTATTTGTA | TTAAAGAAAA | 2880 |
| AGCTT | | | | | | 2885 |

( 2 ) INFORMATION FOR SEQ ID NO:5:

( i ) SEQUENCE CHARACTERISTICS:
        ( A ) LENGTH: 2362 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Staphylococcus epidermidis
        ( B ) STRAIN: Clinical Isolate SE- 3

( x i ) SEQUENCE DESCRIPTION: SEQ ID NO:5:

| | | | | | |
|---|---|---|---|---|---|
| AAGCTTCACA | ACTTGAAAAT | ATAGCACAAA | CATTAAAGGA | TTTAGGTAGA | AAACGAGCAA | 60 |
| TTTTAATTCA | TGGTGCAAAT | GGGATGGATG | AGGCCACGCT | TTCTGGTGAA | AATATCATTT | 120 |
| ATGAAGTTAG | CAGCGAAAGA | GCATTAAAAA | AATATAGTTT | AAAAGCAGAA | GAAGTCGGTT | 180 |
| TAGCTTATGC | AAATAATGAC | ACGTTGATAG | GTGGTTCACC | TCAAACAAAT | AAACAAATTG | 240 |
| CATTGAATAT | CCTAAGTGGC | ACGGATCACT | CAAGTAAACG | AGATGTAGTT | TTGTTAAATG | 300 |
| CTGGAATTGC | TTTATATGTT | GCTGAGCAAG | TGGAAAGTAT | CAAACATGGC | GTAGAGAGAG | 360 |
| CGAAATATCT | CATTGATACA | GGTATGGCAA | TGAAACAATA | TTTAAAAATG | GGAGGTTAAG | 420 |
| TAATGACTAT | TTTAAATGAA | ATTATTGAGT | ATAAAAAAAC | TTTGCTTGAG | CGTAAATACT | 480 |
| ATGATAAAAA | ACTTGAAATT | TTACAAGATA | ACGGAAATGT | TAAGAGGAGA | AAGCTGATTG | 540 |
| ATTCACTTTA | ACTATGATAG | AACATTATCA | GTTATTGCTG | AAATAAAATC | GAAAAGCCCA | 600 |
| TCTGTACCTC | AATTACCGCA | ACGTGATCTT | GTTCAACAAG | TTAAAGATTA | TCAAAAATAT | 660 |
| GGTGCTAATG | CTATTTCAAT | ATTAACTGAT | GAAAATACT | TTGGCGGTAG | TTTTGAACGA | 720 |
| TTAAATCAGT | TATCAAAGAT | AACATCGTTA | CCAGTTTTAT | GTAAAGATTT | TATTATTGAT | 780 |
| AAAATTCAAA | TAGATGTTGC | AAAACGAGCT | GGTGCATCTA | TTATTTTATT | AATAGTAAAT | 840 |
| ATTTAAGTG | ATGACCAATT | AAAAGAATTG | TATTCATATG | CAACAAACCA | TAATTTAGAA | 900 |
| GCTCTAGTAG | AAGTTCATAC | AATTAGAGAA | CTTGAACGTG | CACACCAAAT | TAACCCTAAA | 960 |
| ATTATTGGTG | TTAATAATCG | TGATTTAAAA | CGATTGAAA | CCGATGTTCT | ACATACAAAT | 1020 |
| AAATTACTTA | AGTTTAAAAA | GTCTAATTGC | TGCTACATTT | CAGAGAGTGG | CATTCATACA | 1080 |
| AAAGAAGATG | TTGAGAAAAT | AGTAGATTCA | AGTATTGACG | GTTTACTTGT | AGGGGAGGCA | 1140 |
| TTAATGAAAA | CAAATGACTT | AAGTCAGTTT | TTTGCCTAGT | TTAAAGTTAA | AGAAGAATCT | 1200 |
| CTATGATAGT | TAAATTTTGT | GGTTTTAAAA | CCGAAAGTGA | TATTAAGAAA | ATTAAAAAAT | 1260 |
| TAGAAGTTGA | TGCAGTAGGG | TTTATACATT | ATCCCGATAG | TAAGAGACAT | GTCTCACTGA | 1320 |
| AACAATTAAA | ATATTTGGCT | AAAATAGTGC | CAGATCATAT | AGAGAAAGTA | GTGTCGTAGT | 1380 |
| AAATCCTCAA | ATGTCCACCA | TAAAGAGAAT | AATTAATCAA | ACTGATATTA | ACACAATCCA | 1440 |
| ATTACATGGA | AATGAAAGCA | TTCAATTAAT | TAGAAATATT | AAGAAACTTA | ATTCAAAAAT | 1500 |

|  |  |  |  |  |  |  |
|---|---|---|---|---|---|---|
| AAGAATCATA | AAAGCAATTC | CAGCAACAAG | AAATTTAAAT | AATAACATTC | AAAAGTATAA | 1560 |
| AGATGAGATA | GACTATGTTT | ATTATAGATA | CACCATCAAT | CACATACGGA | GGGACAGGTC | 1620 |
| AAAGTTTTGA | CTGGAAATTA | TTAAAAAAAA | TAAAGGCGTT | GATTTCTCA | TTGCGGTGGT | 1680 |
| TTGGATTTTG | AAAAGATAAA | ACGATTAGAA | ATATATTCAT | TTGGACAATG | TGGTTATGAC | 1740 |
| ATCTCAACTG | GCATTGAGTC | ACATAATGAA | AAAGATTTTA | ATAAGATGAC | TCGAATATTA | 1800 |
| AAATTTTTGA | AAGGAGACGA | ATGATTAATG | AAAATTCAAA | CAGAAGTAGA | TGAATTGGGC | 1860 |
| TTTTTCGGTG | AATATGGTGG | CCAATATGTA | CCTGAAACAT | TGATGCCAGC | TATTATTGAA | 1920 |
| CTTAAAAAAG | CATATGAGGA | CGCGAAATCA | GATACTCACT | TCAAGAAAGA | ATTTAATTAT | 1980 |
| TATTTAAGTG | AATATGTTGG | TAGAGAAACG | CCTTTAACAT | TTGCTGAATC | ATACACAAAA | 2040 |
| TTGTTAGGTG | GTGCCAAAAT | ATATCTTAAA | AGAGAAGACT | TAAATCACAC | TGGTGCTCAT | 2100 |
| AAAATTAATA | ACGCGATAGG | ACAGGCACTA | TTAGCTAAAA | GGATGGGGAA | AACTAAATTA | 2160 |
| GTAGCCGAAA | CAGGTGCTGG | TCAACATGGT | GTAGCAAGTG | CCACCATCGC | TGCTTTATTC | 2220 |
| GATATGGATC | TTATTGTTTT | CATGGGAAGT | GAAGATATCA | AACGTCAACA | ACTTAACGTA | 2280 |
| TTTAGAATGG | AATTGCTAGG | AGCTAAAGTA | GTGTCTGTGT | CAGATGGGCA | AGGAACACTA | 2340 |
| TCAGATGCTG | TAAATAAAGC | TT |  |  |  | 2362 |

( 2 ) INFORMATION FOR SEQ ID NO:6:

( i ) SEQUENCE CHARACTERISTICS:
        ( A ) LENGTH: 8654 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Staphylococcus epidermidis
        ( B ) STRAIN: Clinical Isolate SE- 22

( x i ) SEQUENCE DESCRIPTION: SEQ ID NO:6:

|  |  |  |  |  |  |  |
|---|---|---|---|---|---|---|
| AAGCTTGTTT | TATTGCTTAG | TTATATTTCC | AATAACACTC | ATTTTATATG | TACGTATTGC | 60 |
| CAAAAAAAAT | TATCTATACA | GTAATAAGTA | TGAAATGAGA | ACTGGAATAA | TCATTGGTAT | 120 |
| TATTGCTTTA | ATTCTAGTAA | TTATGCAAGG | GTTTCACTTT | AACTGGGCTA | TTATTCCTAT | 180 |
| TTCTATCTAT | GGTCATCAGT | TTGTATTTTT | CGCTGGAATT | ATTTTAAGTC | TTGTTGGTAT | 240 |
| ATTCTTTAAA | CGTATAGAAT | TTGTAGGAGT | TGGCTTACTA | TTTTGTCAAA | AACATAGATG | 300 |
| CAATGGTAAC | TGACCCGGAA | ATTGCACAGT | TTTTCTCTTT | AGCAATTTGG | ATTATACTTG | 360 |
| TTGTGCTAAT | CATTTTTTAT | ACGATACGTT | TATCTGAACG | CACTAAATCA | TCATCATATA | 420 |
| CAAAGATTTA | AACTCAGAAA | ATATGCTAGA | CATATCTTTC | TGAGTTTTTT | AATTTATTAA | 480 |
| AATATATCAT | TTGTTTACCA | TATAAGTTTG | TTTTAGAAAA | TGAATCACTA | TTTTAATATA | 540 |
| CAAATAATTT | AATTACACTG | AAAATAACCT | AAAAGCGTAA | CACTATTTTA | ATATGGGTAT | 600 |
| ATAAATGACT | AAAGGGAGGT | GCCAAGATGA | ATAAAATTCA | AATTTGTAAT | CAGATTGAAC | 660 |
| TTAACTATAT | TGATGAAGGC | GAAGGCATCC | CCATCATTTT | AATTCATGGA | TTAGATGGAA | 720 |
| ACTTGGCAGG | ATTTAAAGAT | TTAAAAAATG | AACTCAAGAA | GCAGTATAGA | GTAATTACTT | 780 |
| ATGATGTCAG | AGGTCATGGA | AAATCTTCAC | GAACAGAATC | ATATGAATTA | AAAGATCATG | 840 |
| TTGAAGATTT | AAATGATTTA | ATGGGAGCAT | TAAATATCGA | TTCTGCACAT | ATTTTAGGAC | 900 |
| ATGATATGGG | GGGCATCATT | GCGAGTGAAT | TTACTGAAAA | ATATCAATAT | AAAGTGATTA | 960 |

| | | | | | |
|---|---|---|---|---|---|
| CATTGACAAT | TGTTTCGGCC | AAAAGTGAAG | ACATTGCAAA | TGGTTTCAAC | AAATTAATGG | 1020 |
| TTGATTACCA | AGAAGAATTA | GCAGGCTTTA | ATAAATCTGA | GGCAATGATT | ATTTTATTCT | 1080 |
| CTAAATTATT | TAAAGAGAAA | GATAAAGCAA | TGAAATGGGT | ATCAAAGCCA | AAAATTATAC | 1140 |
| AATAGACCAA | CTCCGGAAGA | AAGTGCAATT | GCAGTACGTG | CATTGCTTAA | TATTAAAGAT | 1200 |
| TTAACTCGTG | TTCATCATAA | TGTGTCCATA | CCTACTTTAA | TTGTGAATGG | TAAGTATGAC | 1260 |
| CCACTCATAC | AAAATAAAAG | TCATTATGAT | ATGGATCAAT | ATTATGATCA | AGTTACAAAA | 1320 |
| ATTGTATTTG | ATAATTCAGG | ACATGCACCA | CATATCGAGG | AACCAGAAAA | ATTCCTGAAA | 1380 |
| CTCTACTTAG | ATTTTGTTAG | TTAAAAAATA | AGAACATAAA | TAAAACCCT | TAAATGATTA | 1440 |
| TTGTCGGAAA | ATCATTTGAG | GGTTTTGTAG | TAGCAGTAAA | GTTTGGACTC | AGATCACTAT | 1500 |
| CGTATTAACT | TAATAAAAGA | GTAAAACAGT | CTTATCTTTC | ATAAGTGAAA | GAAATATCTG | 1560 |
| TTTNACTCCC | TAGCCATTAT | ACTTCATTTC | ATTATTGCT | TCTGTGATAC | GGTTGTTTAC | 1620 |
| TCGTTTAAGT | AAATCATCGA | TTTTTTTACG | CTGCTTAGAA | TCTACTAAGA | TTAAAACAGT | 1680 |
| TCTTTCATCG | TGTTCATTAC | GTTTTTTATT | AAAGTAATTT | TCTTGAGATA | AATTTTTAAC | 1740 |
| AGCTTTAACA | ACTTGAGGTT | GTTTATAATT | TAAGTGATTG | ATAATATCTT | TAAGATAATA | 1800 |
| TTCCTCTTCT | TTATTCTCAC | TAATATAAGT | TAATACTGCA | AATTCTTCAA | AGCTGATTGA | 1860 |
| GAATTCTTTT | TTAATTATTC | CTTTTAATCT | GTCAGCATAA | GTGACCATAG | CTAATAATTC | 1920 |
| AAAGCAGTCA | TTGATTTTTG | AAATAGCCAT | TAATGAAACC | TCCCTATTTA | TATCATATCC | 1980 |
| ATAAATCTTA | AAACCCATCT | TTTTAAATTT | AAAGATAGTT | AATTATATTA | TTGAATTAAG | 2040 |
| ATTACTTGGA | TACTATACCC | TAATTTATTA | ATTTATATCT | ATTTTTCTTA | TGAAAATACG | 2100 |
| AAAGTGTCCG | TCATAATATA | GTATTAATTT | AAATTTAAAG | AATATATTTA | ATGCTATATT | 2160 |
| ATTTAGTTAA | TTATAACTAA | ATAAAATTAA | GAAGTAAACA | AATAAGTGTT | TATAAAACAA | 2220 |
| ATTATCTTTT | AAAGTTTATA | CTTGAATTAG | CAATGTAGCA | TTTGCTATAT | TCAAAAAAT | 2280 |
| AAGATTGTTT | CTAATTTTCC | TTAATTTAAT | AAAAATTATA | CTAAAAGAA | TACTTTTTGG | 2340 |
| AAAGAATTTT | ACTAACATTT | TTTATATATA | AATGTTTATT | AATTTAGAAG | TAGGATTTTT | 2400 |
| AACAACTTTT | TCATCTATCA | ATAAGCCTTT | AGTTATATTA | ATATACCCAC | TTTTTAAACT | 2460 |
| CTTTTTGTAT | GTTACTTCTC | TTTTTGTAGA | ATTAAAACAT | AGCGTTTTG | AACAATAGCT | 2520 |
| GACGTAGGTA | ACTCTATGTC | ATTTGAGGCT | AATTTGATTT | TAAAGTGTGT | TCCAATTTGA | 2580 |
| TGATTGGGTT | GTGTAGAAAG | TAAAATGTCG | TAATATGAGA | CGCCATTTTT | TATTTTTGAT | 2640 |
| GGTATATTCG | AAATTTCTTT | AATTTTACTA | GTAAATTGAG | TGTTGTCACT | AGATGTTACA | 2700 |
| GAAATATTTT | GATTTATTTT | TAATAAATTC | AACTCAGATT | CTGATATATT | AGCACGAATA | 2760 |
| ATACGTTCGT | TGCTATTAAT | TTGCACTATC | TTTTCGTTTG | GTTTTGAAGG | GATAGAATTA | 2820 |
| ATATATGAAA | TACTTCCATT | AATTGGTGAA | AATAAAGTGG | ATTTAATTGA | GGATTTAGTT | 2880 |
| TGAATCATTT | GTAATTTTAG | CTGATTAAGG | AATGAATAAT | AATGTAAATC | ATTTTTAGAA | 2940 |
| TTTAAAGTTT | TGTTGTTACG | TTCATTACTA | AGTGTATTTT | GGAGTTCCTC | ATATAAATGA | 3000 |
| TCTTTTTCAT | AATTGTAATA | TTCTAACACT | GGAGTGTTTT | TAGATACTTT | GCTATGATTT | 3060 |
| TTTACTAAAA | GTTTTTGGAG | TTGTCCTAAA | GTGGGAGTGT | AGTAGAAAAT | ATAGCTGTTA | 3120 |
| AGAGGGGCTT | GTATACCAGT | TGTTGAAAGG | AGTAATTTGG | GCTTTGCTTT | TATAGTTTTT | 3180 |
| ATATTTTTAA | TATCTTCTGT | TTTAGAAGTT | AATTTAGAGA | AAGTAATGTA | ACTAAAACTA | 3240 |
| CAAGTTGTGA | GAATGAAAAT | GAATAGTAAT | GAAGAAATAA | CGATGCGTTG | CTTGGTCATG | 3300 |
| GATGTTCACC | TCATAATATT | ATTGTGAGGT | TATTATACAC | TATTATTTTA | AATGAAATAT | 3360 |

| | | | | | | |
|---|---|---|---|---|---|---|
| ATTAATTTTA | AATAAGCATT | ACTTTTGGTT | TGTATATTGT | TTTATTTCAA | AAAATAAAGT | 3420 |
| AAATCAATTT | AATAAATTGA | AAAATAGAAG | GCTATCTTTA | ATTTTAAAAT | ATATGATTCT | 3480 |
| ACATAAATGT | TACTATAAGA | AGAATCACTC | ATAAAAACTG | CCAACAAAGA | CAAAATCTTT | 3540 |
| GTTGGCAGTT | CGAAATAGAC | ATTTATTTGT | ATGAGGAATC | TACATTAATA | TAAGCGGATA | 3600 |
| ATTTTTATTC | AGAATAAGGA | ATTTAAAATA | ATCGTAATAA | AATAATACCT | ATAGCTATAC | 3660 |
| ATAATAATCC | ACCTAACTTA | CGTGATGTTA | TTTTGTTTTT | AGGTGAACCC | AACAAACCGA | 3720 |
| AATGATCGAT | AATAATACCC | ATAATCATTT | GGCCCATCAT | AGCAATTATA | GTAGTTAAAG | 3780 |
| CTGCTCCTAA | GAAAGGCATT | AAAATAATAT | TAGATGTTAC | GAATGCCATT | CCTAGTATCC | 3840 |
| CTCCAATAAA | ATAAATAGAT | TTAATCTTAC | CTAGTGTTTT | ATGAGTAGAT | GATATTTTCA | 3900 |
| GACTACGATT | AAATACTAAT | GTTAATATAA | ATAACGCTAT | TGTACCAACG | CTAAATGATA | 3960 |
| TGAGTGAAGC | AAATATGGAT | GAGTGTGTGT | GTTGAGCCAG | TGTGCTGTTG | ATTGTTGTTT | 4020 |
| GGATTGGCGG | ACGAAACCAA | ATACGAATCC | AATAAGCAAC | CAGAATACTA | TTGGTGTATT | 4080 |
| CTTATGTCTA | TTAACAGGAT | GTCTACGAAC | ATAATTCATA | AATATAATTC | CAGTAATTAA | 4140 |
| AAATATAATT | CCAACACCTT | TAAATAATGT | AAAAGATTGT | TGATGGGCGC | CCAATAATCC | 4200 |
| AAATGTATCA | ATGATTACAC | CCATAATAAT | TTGCCCTGTA | ACCGTAATAA | CAACAGTAAG | 4260 |
| TGCTGCGCCT | AATCTTGGTA | ATAATAATAA | GTTCCAGTT | AAATAGATAA | CACCTAATAG | 4320 |
| TCCTCCTAGG | ACCCAAGTAT | AGTTAAGTGT | TTGCTTAGAA | AAGAATTCTG | GTGTTAATAC | 4380 |
| TTGTGGATGA | ATAATGATAT | TAAGCACAAG | TAAGCATATT | GTTCCGACAG | CAAAAGATAT | 4440 |
| GGTTGAAGCA | TAAAAGATG | AACGGGTAAA | TTGGCTTAGC | CTTGAGTTGA | TTGAAGTTTG | 4500 |
| AATAGGAAGT | AACATGCCAA | CAAAAATTCC | TAAAAGATAT | AGAAAAAACA | ATGATAAAAA | 4560 |
| CCAACTTTCT | CAATTTAATA | TGATTATCAT | ACCATTCATA | ATCATGTTTC | TAAAATGATT | 4620 |
| GAGCCATAAG | CAAAGTATAG | AAATAAGTTG | TGAATGTTCC | GAGGTGTCAT | ACAGCCGATA | 4680 |
| CTATTTGAT | GAATCATTAT | AATAAAATGC | ACATTAAACA | AGTTTTAGAA | TTAAAAAAG | 4740 |
| CGAGACATCA | TTTTGAATTT | GATATCTCAC | TTCATATTAA | TAAAAGAACA | ATGTAAATTA | 4800 |
| AGTTCTTTTT | TAGACTTGAA | CAATTTTAAA | AAATTTGTTC | TTCGATAAGT | CTTTTTTATG | 4860 |
| ATTTTAGTAC | TTTAAATAAA | GCGTCAAAAA | TAATGTTTTA | TGAATTAATT | TTTATCTTCA | 4920 |
| AATATAACAG | TTGTCCTTTT | ATCAATAAGT | TGTGCAGCAT | AAATTTTGAC | AGGCTTTCCC | 4980 |
| AAACTAAATC | TTAAAATGTC | TAATTCTAAA | ATGTCTAATT | CTAAAAGTTG | GTTCATACTT | 5040 |
| TCTTTAATTA | ATTGTTCTGT | AGTAATAGCG | TTAAAATCGG | GTAATAGTAA | TTTGACGGGT | 5100 |
| TTATTAAGAT | TTGATTTAAA | TACGAGTTCC | AAAGTTTTTG | ACATACTGAT | GTATCCTCCT | 5160 |
| TAAATTAAAG | ATTCTGTTTT | AACGATCTCG | ACTTTGTCAT | ACTCTTCGCC | ACTGAACGTT | 5220 |
| CAATGATGGA | ACGAAAGAT | TTGATTTGAT | CATTAGAAAC | AAGCGGATTA | ATGTTAGAAA | 5280 |
| AACGACGCTT | ATGTTCGACT | ACTTTACCTT | CAGAATTATG | TTTGATTTGA | GTAAAGATAA | 5340 |
| TCGTCACTTG | ATTGACTTCA | TTCATAATAA | AACCTCCTTT | CACTATATAT | ATCGAAATAG | 5400 |
| ATTGAAAAAA | AAGGACACAT | TTTTTGAAAA | ATATAGGCAA | ATGCCTTTGA | TGTGATACAA | 5460 |
| ACGTCATTTA | TCATTAATTA | TGAAACCTGT | TTTAGAAGGT | ATATGAGGTA | AGTAGAATTG | 5520 |
| TTAAGTTGTA | AAAGAAAAAA | TTGGAACCTG | ATATTTAAAA | TAACCAACTT | AAAAGATTGA | 5580 |
| TCAGTGTCTA | AAATTACTAT | TTATATATGA | ATTAAAATAT | TAAGATCTCC | CAATATGAGA | 5640 |
| ATGAATTAGT | TTAAGTTTAT | CGATGATTGA | AAAATTATAG | CCTCATGGAT | TCTATCTTAT | 5700 |
| ATAAAATAAA | GTTCTATTCC | CTTTTGGATA | TAAATAAGAA | TAGTTACCTT | TTTGTGATAT | 5760 |

```
GCCAATTCAG AAAAAAAGCG ACAGTGCTTG AATCTATGTA TGCTCAATAA ACTCATTCAA   5820
ATCAACTAGC AATATCAAAT CATAAATCGT GTTGCACCAT AATAAGGATT AAAACCTGTT   5880
AGTTTAACTA ATTTAAGAAA AACATTTGAT TATCTTCTCT TTCAATCGGG AATATTAATT   5940
TCTATCATTC AACAATATTT TGGATATCAG ATAACTTAAG AAATATTGAG ATTTATTGAA   6000
ATACGTATG TTTCAAATCG CCATACAATG ATTACACTTA ATAAATGATT ACACTTAATA    6060
TAAATGTAAA AAGAAAAGGA GGGGTTAAAT GAGTTTAGTA TATCTTATGG CGACTAATTT   6120
ATTAGTCATG CTCATAGTTT TATTCACTCT GAGTCATCGT CAACTAAGAA AGGTTGCGGG   6180
CTATGTTGCA TTAATAGCTC CTATTGTGAC ATCTACATAT TTTATTATGA AAATACCAGA   6240
TGTGATTCGA AATAAGTTTA TTGCTGTTCG ATTACCATGG ATGCCTTCAA TTGATATTAA   6300
TTTAGATTTA AGATTAGATG GTTTAAGTTT AATGTTCGGC TTAATTATTT CGCTAATAGG   6360
TGTGGGTGTA TTTTTTTATG CTACGCAATA TTTATCCCAC AGTACGGACA ATCTTCCTAG   6420
ATTTTTCATC TATTTACTAT TATTTATGTT CAGTATGATT GGCATTGTAA TAGCTAATAA   6480
TACCATCTTA ATGTATGTAT TTTGGGAACT CACAAGTATT TCCTCATTCT TGCTTATATC   6540
CTATTGGTAC AATAATGGTG AAAGTCAATT AGGCGCCATT CAATCTTTCA TGATTACAGT   6600
GTTGGTGGG CTAGCGTTAT TAACAGGATT TATCATTTTA TATATCATTA CAGGAACAAA    6660
CACAATTACT GATATCTTAA TCAACGCAAT GCAATTTCAC GACATCCTTT ATTTATACCA   6720
ATGATTTTGA TGCTATTATT AGGTGCTTTT ACCAAATCTG CACAATTTCC GTTTCATATT   6780
TGGTTACCAA AGGCCATGGC AGCACCTACA CCAGTAAGTG CTTATCTTCA TTCGGCAACA   6840
ATGGTAAAGG CTGGAATCTT TTTACTATTT AGATTACAC CTTTATTGGG ACTTAGTAAT    6900
GTTTATATTT ATACAGTGAC ATTTGTTGGT CTAATAACTA TGTTATTTGG ATCTTTAACT   6960
GCTTTACGAC AATACGACTT AAAAGGTATA CTCGCTTATT CTACAATAAG TCAATTAGGT   7020
ATGATTATGA CAATGGTAGG TCTAGGTGGC GGTTATGCTC AGCACACATC AGATGAATTG   7080
TCTAAGTTTT ATATTTTAGT TTTATTTGCT GGCTTATTCC ATTTAATGAA TCATGCGGTT   7140
TTTAAATGTG CATTATTTAT GGGCGTTGGT ATCATTGATC ACGAGTCCGG AACACGTGAT   7200
ATTCGTTTGC TAAATGGTAT GCGTAAAGTC TCCCCTAAAA TGCATATTGT CATGTTGCTC   7260
GCTGCATTAT CTATGGCAGG TGTTCCTTTT TTAAATGGCT TTTTAAGTAA GGAAATGTTT   7320
TTAGATTCGT TAACTAAAGC AAACGAACTT GATCAATATG GCTTCGTATT AACGTTTGTG   7380
ATTATTTCAA TAGGTGTCAT CGCGAGTATA TTGACTTTTA CTTATGCACT TTACATGATA   7440
AAAGAAACAT TCTGGGGAAA TTACAATATA GAAAAATTTA AACGTAAACA AATACATGAA   7500
CCATGGCTAT TTAGTTTACC AGCTGTGATT TTAATGTTAC TCATTCCAGT TATCTTCTTT   7560
GTTCCAAACG TTTTTGGCAA CTTTGTTATT TTGCCCGCAA CCAGATCTGT ATCTGGGATA   7620
GGGCGGAGGT TGATGCATTT GTGCCACATA TTTCTCAGTG GCATGGTGTG AATCTCCATT   7680
AATTTTAAGA TAGTGTATAT ATTGGACTAT TTTAGCTCTA GTGTGATTGG AAAGAGGTTA   7740
CGCATCAAAT AATCAAAAGT GCTCGATTAC AGTGGCTATC GGAAATTTAT AGAGAATTTG   7800
AATTATACTC AGCCCGTGGT ATACGTGCAT TGATGAATAA TAAATTGAAT TATTACATCA   7860
TGATTACATT ATTTATTTTT GTAGCTATTG TAGTTATGGA TATTTGACTG TGGGTTTTCC   7920
TCATGTACTC AGCTTCATAT TAGTTCTTTC GGACCGTTGG AAGTTATCTT ATCAGTTGTA   7980
ACATTGATTA TCGGCATTTC ATTAATCTTT ATTCGTCAAC GACTAACGAT GGTGGTATTG   8040
AATGGAATGA TTGGATTCGC AGTTACATTA TATTTATTG CAATGAAAGC TCCAGATTTA    8100
GCTTTAACAC AGTTAGTTGT TGAAACTATT ACGACAATCT TATTTATTGT TAGTTTTTCG   8160
```

| | | | | | |
|---|---|---|---|---|---|
| AGACTACCTA | ACATCCCTCG | AGTTAAGGCA | AATTTAAAAA | AAGAGACCTT | CAAAATCATT | 8220 |
| GTGTCACTTG | TTATGGCATT | GACGGTGGTA | TCACTTATTT | TTGTTGCTCA | ACAAGCAGAT | 8280 |
| GGTATGCCTT | CAATTGCTAA | ATTTTATGAA | GATGCATATG | AACTTACAGG | TGGAAAAAAT | 8340 |
| ATTGTCAATG | CTATACTAGG | TGACTTCAGA | GCTTTAGATA | CTATGTTTGA | AGGACTAGTG | 8400 |
| TTAATCATAG | CTGGATTAGG | TATTTATACG | TTACTTAATT | ACAAAGATAG | GAGGGGGCAA | 8460 |
| GATGAAAGAG | AATGATGTAG | TACTTAAATC | AGTTACAAAA | ATTGTAGTGT | TTATTTTGTT | 8520 |
| AACATTTGGA | TTTTATGTAT | TTTTTGCTGG | CCATAATAAT | CCAGGTGGTG | GCTTTATTGG | 8580 |
| TGGCTTGATT | TTTAGCTCGG | CATTTATCTT | AATGTTTCTT | GCCTTTGATG | TAAATGAAGT | 8640 |
| GTTGAAAAAA | GCTT | | | | | 8654 |

( 2 ) INFORMATION FOR SEQ ID NO:7:

( i ) SEQUENCE CHARACTERISTICS:
        ( A ) LENGTH: 5024 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Staphylococcus epidermidis
        ( B ) STRAIN: Clinical Isolate SE- 32

( x i ) SEQUENCE DESCRIPTION: SEQ ID NO:7:

| | | | | | |
|---|---|---|---|---|---|
| AAGCTTTTTG | ATTTTTAAAG | AAAAAATTAA | ACAAGGGGGC | ATTGCTTATG | GTCAATAGAA | 60 |
| GAAAGATATC | AATTATTGGC | GCGGGACATA | CAGGTGGGAC | TCTAGCATTC | ATTCTTGCAC | 120 |
| AAAAGGAATT | AGGAGATATT | GTGTTGATTG | AACGCCAGCA | ATCAGAGGGT | ATGGCTAAAG | 180 |
| GAAAGGCGTT | AGATATTTTA | GAAAGCGGAC | CCATTTGGGG | GTTTGACACA | TCTGTACATG | 240 |
| GTTCAGTAAA | TATAGAAGAT | ATTAAAGATT | CAGACATAGT | GGTGATGACT | GCAGGTATAC | 300 |
| CTAGGAAATC | AGGAATGACA | AGGAGAAGAA | TTAGTTCAAA | CTAATGAACA | AATAGTACGA | 360 |
| GAAACTGCAT | TACAAATTGC | AACGTATGCA | CCTCATTCAA | TAATTATTGT | ATTGACTAAT | 420 |
| CCGGTTGATG | TTATGACATA | TACTGCATTT | AAAGCATCAG | GTTTTCCTAA | AGAACGTATT | 480 |
| ATTGGTCAAT | CTGGAATTTT | AGACGCTGCA | AGATATCGAA | CTTTTATTGC | TCAAGAACTT | 540 |
| AACGTGTCTG | TCAAAGATGT | AAATGGGTTT | GTTTAGGTG | GACATGGTGA | TACGATGTTA | 600 |
| CCTTTGATTA | ATAACACACA | CATTAATGGG | ATTCCAGTTA | AGCATCTTAT | TTCTGAAGAA | 660 |
| AAGATTGATC | AAATTGTTGA | ACGTACACGT | AAGGGTGGTG | CAGAAATTGT | TGCATTACTA | 720 |
| GGTCAAGGCT | CAGCATATTA | TGCACCAGCA | ACTGCTATAT | ATGAAACTAT | AGATGCAATT | 780 |
| TTTAATGATC | GGAAACGGTT | ATTACCAAGT | ATTGCTTATC | TAGAGGGAGA | ATACGGTTGT | 840 |
| TCAGATATTT | GTTTCGGAGT | TCCTACTATA | ATAGGATATC | AAGGAATAGA | AAAGATTATA | 900 |
| GAGGTAGATA | TGAATAATGA | TGAGTATCAA | CAACTACAAC | ACTCTGCGCA | AGATGTGAGT | 960 |
| GAAGTCAAAA | ACTCACTAAA | ATTCAAATAA | ATAATTATGA | AGTTCTACAT | CTTAAATTGT | 1020 |
| TAGATTTTTG | TGAAAATTGT | GTAAAGGGTA | TTTTTTCGTT | GATTTATAAA | AGCGCTTTCT | 1080 |
| TGATATAATG | AACATATATT | CATAGAATAA | GGAGACGATT | AAAATGGCTA | AAGGGGACCA | 1140 |
| ATATCAAGCT | CATACTGAAA | AATATCATGA | GTAAAAGTC | TAAAAAAGT | TATAAACCTG | 1200 |
| TGTGGATTAT | CATTAGTTTT | ATTATTTAA | TTACAATCTT | GTTATTACCC | ACACCAGCAG | 1260 |
| GATTACCTGT | AATGGCTAAA | GCAGCACTAG | CTATTTAGC | TTTCGCTGTA | GTTATGTGGG | 1320 |
| TTACAGAAGC | AGTTACTTAT | CCAGTTTCTG | CAACATTAAT | TTTAGGATTA | ATGATACTTT | 1380 |

-continued

| | | | | | |
|---|---|---|---|---|---|
| TACTAGGTTT | AAGTCCAGTT | CAAGATTTAT | CCGAAAAACT | TGGAAACCTA | AAAGTGGCGA | 1440
| CATAATACTA | AAAGGTAGCG | ATATTTTAGG | AACGATAAC | GCGCTTAGTC | ACGCTTTTAG | 1500
| TGGTTTTTCA | ACCTCAGCCG | TAGCACTTGT | AGCTGCAGCA | TTATTTTTAG | CAGTAGCTAT | 1560
| GCAGGAAACC | AATTTACATA | AACGACTTGC | ATTATTTGTG | CTATCAATTG | TTGGAAATAA | 1620
| AACTAGAAAT | ATAGTCATTG | GTGCTATTTT | AGTATCTATT | GTTCTAGCAT | TCTTTGTACC | 1680
| ATCAGCTACA | GCACGTGCTG | GTGCAGTTGT | CCCAATATTA | CTGGGAATGA | TTGCTGCATT | 1740
| TAATGTGAGT | AAGGATAGTA | GACTTGCTTC | ATTATTAATT | ATTACTGCTG | TACAAGCAGT | 1800
| TTCGATATGG | AATATAGGTA | TTAAAAACGG | CTGCAGCACA | AAATATTGTA | GCCATCAATT | 1860
| TTATTAACCA | AAATTTAGGA | CATGATGTAT | CATGGGGAGA | GTGGTTTTA | TATCTGCGCC | 1920
| GTGGTCAATC | ATTATGTCTA | TAGCTCTTTA | TTTTATAATG | ATTAAGTTTA | TGCCACCTGA | 1980
| ACATGATGCA | ATTGAAGGTG | GAAAAGAGTT | AATTAAAAG | GAACTTAATA | AATTAGGACC | 2040
| AGTCAGTCAT | AGAGAATGGC | GACTAATTGT | GATTTCAGTG | CTTTTATATT | CTCTGGTCGA | 2100
| CTGAGAAAGT | ATTGCATCCG | ATTGATTCAG | CTTCGATTAC | ACTAGTTGCT | CTAGGTATTA | 2160
| TGCTAATGCC | AAAGATTGGT | GTTATTACTT | GGAAAGGTGT | TGAAAAGAAG | ATTCCTTGGG | 2220
| GGACGATTAT | AGTATTTGGT | GTAGGAATCT | CACTTGGTAA | TGTATTACTT | AAAACAGGAG | 2280
| CCGCTCATGG | TTAGTGATCA | ACATTTGTTT | GATGGGTCTT | AAACATTTAC | CGATCATAGC | 2340
| AACTATTGCG | TTAATTACCT | TATTTAATAT | ATTAATACAT | TTAGGTTTTG | CAAGTGCAAC | 2400
| GAGCTTAGCC | TCTGCGTTAA | TACCTGTGTT | TATTTCTTTG | ACTTCAACGC | TAAATTTAGG | 2460
| TGATCATGCT | ATTGGTTTTG | TATTAATACA | ACAATTTGTG | ATTAGTTTTG | GTTTCCTACT | 2520
| ACCTGTCAGT | GCACCACAAA | ATATGCTTGC | ATATGGTACT | GGGACTTTTA | CCGTAAAGGA | 2580
| TTTTTTAAAG | ACAGGTATAC | CTTTAACGAT | AGTAGGTTAT | ATTTAGTTA | TCGTATTTAG | 2640
| TTTAACGTAT | TGGAAATGGC | TTGGTTTAGT | GTAAGTAAAA | GATTAGGTA | TTAAAATGAT | 2700
| AATTATAAAT | GTCTCGTAAA | GTTTAATATT | TTAACTTTAC | GACACATTTT | TTATAAACTC | 2760
| GTGGCAAGTT | AATCTTAATA | GTTGAAATGT | ATCGTATAAA | AAATATATGA | ATGTAAATAG | 2820
| AATTTAGTAT | TAGAGAATAA | CAAAAAATTG | ATGTTAGGTG | GTAAAATCTA | ATGGCTATAG | 2880
| GTGTCATATT | AAATAGAGTT | TTTAGGCTAA | ATAATAATCC | ATTATTGAT | TATATATATA | 2940
| GTAATAAAGA | ATCTATAAAT | CATTGTTATT | TTATTATTCC | AACTGAAGAG | TTTGAAGAAG | 3000
| AAGCAAAAAA | GAAAGCACAA | TACTATTATG | GGTCCATACA | GAAGTTTATG | TATGAACTAC | 3060
| AACGATATGA | TATAGAACCC | TTTTTGATGT | CTTATGATAA | ATTAATAGAC | TTTTGTAAAA | 3120
| AACAAGCTAT | AGACAAGTT | GTTGTTGCAG | GTGATATTAT | GAGTTATCAT | CACGAAGAAT | 3180
| ATGACATTTT | ACATCAAAGG | AAACGATTTA | AACAAGCTAA | TATTCAAGTA | ATATCATTAA | 3240
| GAGCAAATCA | TTATTTTAAC | CCCCGCAAAA | CACATAATAA | ACAAGGGGAA | CCATATAAAG | 3300
| TATTTACCAG | TTTTTATAGA | AAATGGCGTC | CTTACTTAAT | GATTAGAGAT | GAATATGACT | 3360
| ATCATTTAGA | AGATATTTCA | AAGGTTGTAG | TGAAATCTCA | ACATAAAATT | AAAGAAGATT | 3420
| ATCATTCATA | TGGTATAAGT | GAACGTGATG | TTCAAAATCG | TTGGTCTGAA | TTTTTATCTC | 3480
| AAGATATCGA | AAATTATAAA | GAAAACAGGG | AATACTTGCC | TGAAGTATTA | ACAAGCCAAC | 3540
| TAAGTATTTA | CTTAGCTTAT | GGAATGATAG | ATATTATACA | ATGTTTTCAA | CGATTTACTT | 3600
| CAAAATTATG | ATAAAAATGA | ACAAAATTAC | GAAACTTTTA | TACGTGAATT | GATTTTTAGA | 3660
| GAGTTTTATT | ATGTATTAAT | GACCAATTAT | CCCGAAACAG | CTCATGTTGC | TTTTAAAGAA | 3720
| AAATACCAAC | AATTGAAATG | GTCTTATAAT | GAAGAGAATT | TTAAACTGTG | GAAAGATGGG | 3780

-continued

| | | | | | | |
|---|---|---|---|---|---|---|
| AATACTGGTT | TTCCAATTAT | TGATGCAGCA | ATGGAGGAAC | TTAAAACAAC | TGGATTTATG | 3840 |
| CATAATCGCA | TGAGAATGGT | AGTTTCTCAA | TTTTTAACTA | AAGATTTGTT | TATTGACTGG | 3900 |
| ATTTGGGGTG | AGTCATTTTT | CAAACAAAAA | TTAATAGATT | ATGATGCAGC | TTCAAATGTT | 3960 |
| CACGGATGGC | AGTGGTCAGC | TTCTACTGGA | ACAGATGCTG | TACCATACTT | TAGAATGTTT | 4020 |
| AATCCTATAA | GACAAAGCGA | GCGTTTTGAT | AATAATGCAC | GATATATAAA | AACTTACATT | 4080 |
| CCAAGATTAA | ATCAGGTAGA | TGCTAAGTAT | TTACACGATA | CTCATAAATT | CGAGCAACAA | 4140 |
| ATAAGGGGC | AAGGTGTTGA | AATAGGTAAA | GACTATCCTA | AACAATGAT | TGATCACAAA | 4200 |
| GAAAGTAGAC | AACGTGTAAT | GTCAGAATTC | AAAGCTATAG | ATTAAATAAA | AAGATCTGA | 4260 |
| ACAACATGAT | ATAGGTGTTC | AGATCTTTAT | CTAGTTACAT | AAAAAAGCAA | ACATGAATTA | 4320 |
| AAATATATTC | TAACAAAGTT | AAAATATACA | TATATTTAAG | ATTTAATTTA | GTTTTCAAAG | 4380 |
| GTACTTCCCA | ATTTGTATAA | CGGGGCTCAT | AATAAAATAA | TTGCATCAAA | TATAATCCTA | 4440 |
| TCCCTAACGG | TAAACACATT | AATAAAATAG | CTTTAGTATA | ACTCCATCCT | ATTTGATGCC | 4500 |
| ATAAATGACC | TATCATAAGT | TGAATAATGA | TGAGACATAC | CATTAAAATT | ACTTCAATTA | 4560 |
| TCATTGGTAT | AATCTCACCC | CTTTAATAAA | CAATATGACT | GTTGCTTGTA | TGAGCACCAT | 4620 |
| TAAAACGACA | AATAGTAACG | CTTTAACATC | TATGATTAAA | AAAACCTCTT | TCACAATTTT | 4680 |
| TAAAGGTGCA | TTTAATAAAT | AGACAGTATG | TAATCTTAAG | AATCGACCGA | TGTAAATACC | 4740 |
| TAATCCATTT | AAGAACATTA | ATATAACTAT | CAATAGTCGA | TTTAACCATA | CATAAGACGT | 4800 |
| AAAATGTGCA | ATTTCTAAAA | ATATAAGAAT | TGTGAGGTAT | ATTGCTAAGA | GTACGCCAAG | 4860 |
| TATTAAATAG | GTGAAATAAA | TCCATTCTGT | GATGTTTAAT | CCAGCTAAAA | AGTTAAATTG | 4920 |
| AAATTGGTTT | AAGTGTATGA | GATCGGTAAT | CATATAAAAT | GTGTTTGGAA | CTAATAATAG | 4980 |
| AAATATGAGT | CCGAAAACAA | TAAATAAGGG | CCATTCAAAA | GCTT | | 5024 |

( 2 ) INFORMATION FOR SEQ ID NO:8:

( i ) SEQUENCE CHARACTERISTICS:
        ( A ) LENGTH: 3287 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Staphylococcus epidermidis
        ( B ) STRAIN: Clinical Isolate SE- 37

( x i ) SEQUENCE DESCRIPTION: SEQ ID NO:8:

| | | | | | | |
|---|---|---|---|---|---|---|
| AAGCTTGCCT | ATTGATTTTA | AAAAATTAAT | GATTATAGGT | TCACTCATAT | CTGTTGCAAC | 60 |
| TGCATCAGTG | CCTATGTTTT | TTGGGAAGCC | ATTTTTATAT | CAAACTGAAG | CAAATGTAAC | 120 |
| ATTTCCATTA | CTAGGACATG | TTCATGTTAC | TACTGTGACT | TTATTTGAGC | TTGGCATCTT | 180 |
| ATTAACAGTA | GTAGGTGTGA | TTGTTACAGT | TATGCTATCT | ATAAGTGGGG | GTAGATCATG | 240 |
| AATTTAATAT | TACTCCTTGT | GATAGGATTT | TTAGTGTTTA | TTGGAACTTA | TATGATTTTA | 300 |
| TCTATTAATT | TAATTCGTAT | TGTTATTGGT | ATTTCTATTT | ATACACACGC | CGGTAATTTA | 360 |
| ATTATTATGA | GTATGGGGAA | ATATGGACCT | CATATGTCTG | AACCGCTAAT | TCAAGGTCAT | 420 |
| GCTCAAAACT | TTTGTTGATC | CTTTATTACA | AGCTATCGTT | TTAACAGCTA | TTGTGATTGG | 480 |
| ATTTGGTATG | ACTGCGTTTT | TATTGGTGTT | AATATATAGA | ACTTACAGAG | TAACTAAAGA | 540 |
| GGATGAAATA | AGTGCATTGA | AAGGTGATGA | AGATGATGAG | TAATTTAATA | ATATTGCCTA | 600 |

-continued

```
TGTTGTTGCC TTTTGTATGT GCTTTAATTT TAGTCTTCAC TAAAAATAAA AATCGTATTT      660
CGAAAATCCT ATCCATTACA ACTATGATTG TTAATACAAT GATTTCAATT GCTTACTTA      720
TTTATGTCGT TAATCATAAA CCGATAACAC TTGATTTTTG GGGGGATGGA AAGCACCTTT      780
CGGCATTCAA TTTCTAGGTG ATTCACTGAG TCTGCTTATG GTGTCAGTAT CATCTTTTGT      840
TGTTACGCTA ATAATGGCAT ACGGCTTTGG TAGAGGGGAG AAGCGAGTCA ATCGATTCAC      900
CTCCTACATT ATCTTTATTA ACAGTAGGTG TTATTGGTTC GTTTTAACT TCTGATTTAT      960
TTAACCTATA CGTGATGTTT GAAATTATGC TTCTTGCTTC GTTTGTACTT GTTACATTAG     1020
GACAATCTGT TGAACAATTA CGTGCAGCGA TAGTATATGT TGTTCTGAAT ATTTTAGGTT     1080
CGTGGTTGCT TTTATTAGGA ATTGGCATGT TATATAAGAC AGTCGGAACA CTTAATTTCT     1140
CACATTTAGC GATGCGATTG AATCATATGG AAAATAACCA AACAATAACG ATGATATCTT     1200
TAGTATTTCT AGTTGCTTTT AGTTCAAAGG CAGCACTAGT GATTTTCATG TGGTTACCTA     1260
AAGCATATGC AGTGCTTAAT ACGGAACTTG CCGCGTTATT TGCAGCATTG ATGACAAAAG     1320
TTGGAGCTTA TRCGCTTATT CGTTTTTTTA CTTACTATT CGACCATCAT CCAAGCGTCA     1380
CGCATACATT GCTCGTGTTT ATGGCTTGTA TCACAATGAT TATCGGTGCA TTTGGTGTCA     1440
TCGCTTACAA AGATATTAAG AAAATTGCGG CTTATCAAGT TATTTTGTCT ATTGGATTCA     1500
TTATTTTAGG TTTAGGTTCT CATACTATAT CAGGTGTAAA TGGTGCTATC TTCTATTTAG     1560
CGAATGATAT TATCGTTAAG ACATTATTGT TTTTTGTAAT TGGTAGTCTT GTTTATATGT     1620
CAGGCTATCG AAATTATCAG TATTTAAGTG GACTGGCAAA AGAGAACCAT TCTTTGGTGT     1680
TGCATTTGTC GTGGTAATTT TTGCTATAGG TGGCGTACCT CCTTTTAGTG GCTTTCCGGG     1740
TAAAGTCTTA ATATTCCAAG GGGCTATTAC AAATGGTAAT TATATTGGTT TAGCACTTAT     1800
GATTGTGACA AGTTTAATTG CTATGTATAG TCTTTTTAGA GTGATGTTTA TAATGTATTT     1860
TGGTGATGCT GACGGAGAAC AAGTACAATT TAGACCACTA CCTATTTATC GTAAAGGTTT     1920
ACTTAGTGTT TTAGTTGTAG TGGTATTAGC GATGGGTATT GCAGCCCCTG TTGTTCTGAA     1980
AGTAACAGAG GATGCAACAA ATCTTAATAT GAAAGAAGAT GTCTTTCAAA AGAATGTAAA     2040
TACACATTTG AAGGAGGTTA ATCATAAGTG AAGCAAGTTG TATTAAATAT TGTTATCGCG     2100
TTCCTTTGGG TACCCTTTCA AGATGAAGAT GAATTTAAAT TTACAACCTT CTTTGCTGGA     2160
TTTTTAATTG GTTTAATTGT GATTTATATT CTGCATCGCT TTTTTGGTGA AGAATTTAT      2220
TTGAAAAAGA TATGGGTGGC TATTAAATTT TTAGCTGTAT ACCTATACCA GCTTATTACT     2280
TCTAGTATAA GTACCATAAA TTACATCTTA TTTAAGACGA ATGAAGTTAA TCCAGGTTTA     2340
CTCACATATG AAACTTCATT AAAAAGTAAT TGGGCTATTA CTTTTTAAC GATTTTAATT     2400
ATTATTACTC CAGGATCGAC AGTTATTCGA ATTTCTAAAA ATACTAATAA ATTTTTTATT     2460
CACAGTATTG ATGTGTCAGA AAAAGATAAA GAAAATCTTC TAAAAAGTAT TAAGCAGTAT    2520
GAGGATTTAA TTTTGGAGGT GACACGATGA TTGAAATGTT CACTCAAATA TTTATTATAA    2580
GTGCATTAGT GATTTTTGGT ATGGCACTAC TTGTTTGTCT AGTCAGATTA ATTAAAGGTC    2640
CCACTACTGC TGATAGAGTT GTATCATTTG ATGCCTCGAG TGCTGTTGTT ATGTCTATTG    2700
TTGGTGTGAT GAGCGTTATT TTAACTCAG TGTCTTAATG TTAATTGCAA TTATTTCGTT    2760
TGTCAGTTCG GTCTCAATTT CAAGATTCAT CGGGGAAGGA CGTGTCTTCA ATGGAAATCA    2820
TAAAAGACAT CGTTAGTCTT ATTGCTTCGA TACTTATTTT CTTAGGAAGT ATTATTGCAT    2880
TAATTAGTGC AATAGGGATT GTAAAATTTC AAGATGTCTT TCTAAGAAGT CACGCCTCAA    2940
CGAAAAGTTC TACATTGTCA GTATTACTAA CTGTAGTTGG TGTACTGATC TATTTTATTG    3000
```

-continued

| | | | | | |
|---|---|---|---|---|---|
| TGAATTCAGG | TTTTTTCAGT | GTCAGATTAT | TATTATCACT | AGTTTTTATC | AATCTTACAT | 3060 |
| CTCCGGTTGG | AATGCATTTG | ATAAGTAGAG | CGGCCTACCG | TAATGGTGCA | TATATGTACA | 3120 |
| GGAAAGACGA | TGCATCTAGA | CAATCTACTA | TCTTATTAAG | CCAAAAGAG | TTTAATACGC | 3180 |
| CAGAAGAATT | AAAAAAACGT | GCAAAACTAC | GAGAAGAAAG | ACGAGAAAAA | TTATACTATA | 3240 |
| AAGAAAAAGA | ATATATTAAT | AAAATGGACG | ATTGATTGTT | TAAGCTT | | 3287 |

( 2 ) INFORMATION FOR SEQ ID NO:9:

( i ) SEQUENCE CHARACTERISTICS:
        ( A ) LENGTH: 2291 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Staphylococcus faecalis
        ( B ) STRAIN: Clinical Isolate S2- 1

( x i ) SEQUENCE DESCRIPTION: SEQ ID NO:9:

| | | | | | |
|---|---|---|---|---|---|
| AAGCTTTAGA | TAATGATAAA | CGCGTGTATG | TGAATGTCCA | GCCGATTCAA | TCGCCTACTG | 60 |
| GAGAAACAGT | GATTGGTGTC | CTTTATGTGA | AAAGTAATTT | AGAAAATAAA | TACCAAGAAA | 120 |
| TTACTAACAC | AGCAAGTATC | TTTTTCACTG | CTTCTATTAT | TGCCGCAGCA | ATCTCGATTA | 180 |
| TTGTGACCCT | ACTGATTGCA | CGATCAATCA | CGAAGCCGAT | TGGTGAAATG | CGCGAGCAAG | 240 |
| CCATTCGAAT | CGCTCGTGGT | GATTACGCTG | GAAAAGTAGA | AGTCCATGGA | AAAGATGAAT | 300 |
| TAGGCCAATT | AGCAGAAACA | TTTAATCAAT | TATCAGAACG | GATTGAAGAA | GCACAAGAAA | 360 |
| CAATGGAAGC | AGAAGAATCG | TTTAGATAGT | GTCTTAACGC | ATATGACAGA | TGGTGTCATT | 420 |
| GCGACGGATC | GCCGCGGAAA | GGTGATTACG | ATTAATGAGA | TGGCCCTTTC | ATTATTAAAT | 480 |
| GTAAAAAATG | AAAATGTGAT | TGGGACCTCG | TTATTAGAGT | TGTTAGATAT | TGAAGAAGAT | 540 |
| TACACATTGC | GGAAGCTGTT | AGAAGAGCCA | GATGAACTGC | TGATTGATCG | CTCAACGTCT | 600 |
| GATCGTGAAG | AAGACCAAAT | GATTATCCGG | GTAGACTTTA | CGATGATTCG | TCGGGAATCA | 660 |
| GGATTTATTA | CTGGCTTAGT | TTGCGTACTT | CATGACGTCA | CAGAACAGGA | AAAAACGAA | 720 |
| CGGGAAAGAC | GGGAATTTGT | TTCCAATGTT | TCTCATGAGT | TGCGACGCCT | TTGACAAGTA | 780 |
| TGCGTAGTTA | TATAGAGGCT | TTGAGTGAAG | GAGCTTGGGA | AAACCCTGAG | ATTGCGCCGA | 840 |
| ATTTCTTAAA | AGTCACGTTA | GAAGAAACCG | ACCGGATGAT | TCGTATGATT | AATGATTTGT | 900 |
| TAAATTTATC | TCGGATGGAC | TCTGGGAATA | CACATCTTCA | ATTAGAGTAT | GTGAATTTTA | 960 |
| ACGAATTGAT | TAATTTTGTC | TTGGATCGCT | TTGATATGAT | GATTGAAAAT | GAGCAAAAAA | 1020 |
| ATTACAAAAT | TCGCCGTGAA | TTTACTAAAC | GCGATTTATG | GGTAGAGTTA | GATACAGACA | 1080 |
| AAGTAATTCA | GGTTTTTGAC | AACATTTTGA | ACAATGCGAT | TAAGTATTCG | CCAGATGGCG | 1140 |
| GCGTCATTAC | CTGCCGACTA | GTTGAAACAC | ATAATAATGT | CGTCTTTAGT | ATCTCGGACC | 1200 |
| AAGGTTTGGG | CATCCCTAAA | AAAGATCTCG | GGAAAGTCTT | CGAGCGTTTT | TATCGTGTGG | 1260 |
| ATAAAGCACG | TGCGCGAGCA | CAAGGTGGGA | CTGGTTTAGG | TTTAGCAATT | TCTAAAGAAG | 1320 |
| TAATTCGGGC | CCATAACGGG | AGTATTTGGG | TGGAAAGTAC | AGAAGGTGAA | GGATCAACTT | 1380 |
| TCTATATTTC | ACTACCATAT | GAACCTTATG | AAGAGGATTG | GTGGGAATGA | TGAAAAAATC | 1440 |
| AGAATGGATT | ACAAGAATTG | GCTTGATTTT | GATGGTCATT | TTAAGTATAT | ATTTTTCAGT | 1500 |
| CAATATCTGG | CTGAATTCTG | CCAAAAAAAT | ACCAGAAATG | AAGTCGGGAA | GCCAAGTCAC | 1560 |
| AACAGCTGTC | AATGAAAAAG | CCATTGGCGA | TGTCTATTTA | CCTTTGCAAT | TGATTCGAAT | 1620 |

| | | | | | | |
|---|---|---|---|---|---|---|
|AGCCGATGGA|AAAGCGATGC|AAAGTAATCG|TGAAACATTA|ATTAGTAATG|TTCAAAATGA|1680|
|TATTAAAATG|GCTACGTTTG|GTAAATTGAC|ACAAGTTGTG|ACAAAAAATG|CAGAGCAACT|1740|
|TAAGCGCTAC|AACCAAATGG|AACAAGGCAT|TGAACTTCTT|TATCAAGGTC|CCTTTTTAAT|1800|
|CTCGGACTAT|GCTTCGATTT|ATAATCTATC|CATTAATTTT|ACTAACTTTA|ATGAGTTGAC|1860|
|GGACCAGTAT|TTTACGAAAA|TTCAATTGGA|TTTAACGAA|AATAAGATAC|GTTTTTAGA|1920|
|TTATGATCAA|TCCAACGTCT|ATGAAGCGCC|CATGACTGTT|AATAAGGCGC|GCTTAATGGG|1980|
|AATTATCAAT|AAAGAGGGAT|TGCAATATCA|AGACGTTTCC|GAAAATACGC|TAACCAAACA|2040|
|AGGACAATGT|TATTTAACCA|ATGATATGAA|GTTGAAAAAG|TACAGTTATA|TCTTANTTCG|2100|
|CAACCAGTTA|CTCGTTTTAG|GAATGCTTTT|TTCAATGAAA|CGGAAGATAT|CCAAACCAAT|2160|
|GAAGACAGTC|AAGACTTAAC|CTATACGAGT|AAAGAAGAAC|GATTGTTTGC|AGAAGAAAA|2220|
|CTGGGGAAAA|TCGATTTTAA|AGGGACCTTG|CCAGAAGAGA|ATAAACGGGA|CTCAATCTAT|2280|
|AATCAAAGCT|T| | | | |2291|

( 2 ) INFORMATION FOR SEQ ID NO:10:

( i ) SEQUENCE CHARACTERISTICS:
        ( A ) LENGTH: 3719 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Enterococcus faecalis
        ( B ) STRAIN: Clinical Isolate S2- 3

( x i ) SEQUENCE DESCRIPTION: SEQ ID NO:10:

| | | | | | | |
|---|---|---|---|---|---|---|
|AAGCTTCATT|AGAGCGTCAA|CTGTTTTTGG|TGTTGGGTTC|ACAATGTCAA|TTAGACGTTT|60|
|GTGAGTACGC|ATTTCGAATT|GTTCGCGAGA|ATCTTTGTAT|TTATGAGTCG|CACGAATAAC|120|
|TGTGTAAAGT|GAGCGTTCTG|TTGGTAATGG|AATCGGACCT|GATACGTCAG|CTCCAGTTCT|180|
|TTTTGCTGTT|TCCACAATTT|TATCCGCTGA|TTGATCTAAA|ATACGGTGTT|CATACGCTTT|240|
|TAAACGGATA|CGAATTTTTT|GTTTTGCCAT|CTTGTTCCCT|CCTTCGCCTA|TTTTAAAAGT|300|
|AGACATAGCT|CCACGAAAAT|TTATCCGGCA|TGCTCGTTCA|TGGCAAAGCG|TCCGAGCGTG|360|
|TCGCAACCTC|TCGCTTCACA|GCCGGCAAAT|CAAATCGTTG|ATCTACCAAT|GCTTTTTACA|420|
|CTCCTGTAAA|CAGCACCTTT|TTGATTATAC|TATGAAAGGA|TAGTGTTAGC|AAGGATTTTC|480|
|TGCGTTTTTT|TAAAAGAATT|TTTTCTTGTT|TTGAAAAGCA|TTTGTTTTGT|TTTTCAATTC|540|
|TTTTCATTCT|ATTTTTATAA|AAAAAGAATT|TGAGATTCTT|TTTTTACCAG|AATCTCAAAT|600|
|TCTTTCTTTT|TTATTCTATT|AACCAATCCG|GCGCATTGGA|ATATCATTGT|TATCTGGATG|660|
|AACCAATAAA|TATTGAATAA|CATCAATATT|GCTTGCTTGG|AATGAGGCTG|CACATGCTTG|720|
|CAAATATAAG|TCCCACATTC|GATAGAAGCG|CTCGCCTTTT|TCGTCAACAA|TTTCTGTTTC|780|
|TATATTATGG|AAGTTTTTTG|TCCAATGTTC|CAACGTCAAT|TGATAATCTC|TGCGCAAACT|840|
|TTCCAAGTCA|ATCACTTGCA|AGTCGTTTTC|TGTCATATGG|CCGACTAGCT|CAGTGACACC|900|
|AGGAATATAG|CCACCTGGGA|AAATATAACG|ATTAATCCAA|GCATTTTAG|CCCCACCTTG|960|
|TTGGCGACTG|ATCCCATGAA|TCAACGCCGT|ACCTTTAGGC|GCTAAATTTC|GCTGAACGAC|1020|
|ATCAAAATAT|TCATGTAGAT|TTTCCGCACC|GACATGTTCA|AACATCCCAA|CACTCGTAAT|1080|
|ATGGTCAAAA|GACTCTCCTT|TTAAATCACG|ATAATCCATC|AATTTGACAG|TCATTCGATC|1140|

| | | | | | | |
|---|---|---|---|---|---|---|
| TTGTAGACCT | TCTTTTTCTA | TAATATGGCG | AATATGATGA | AATTGCTCTT | CACTTAATGT | 1200 |
| AATCCCAGTT | GCTTTGGCTC | CATATTCTTT | CACCGCAGTT | AAAATTAACG | TGCCCCAGCC | 1260 |
| GCAGCCAATA | TCCAGTAAAG | TGTCGCCCTC | TTTGATAAAC | AATTTATCTA | AAATATGATG | 1320 |
| AACTTTATTC | ACTTGCGCTT | GTTCTAATGT | ATCTTCAGGC | GTTTTAAAAT | AAGCACATGA | 1380 |
| ATACGTCATT | GTTTGGTCAA | GCCATTTTTT | GTAAAAATCA | TTTCCTAGAT | CGTAATGGCT | 1440 |
| GTGAATATCC | TCTTGCGAAC | GTTTTTTTGA | ATGACTTTCT | TTAGGAAGCC | ATTTAATAAA | 1500 |
| TTTAGCATTG | TGTAAAAAGC | TATCCTTTTG | GTTATACACA | TCATAAATCA | GCGCTTGGAT | 1560 |
| ATCGCCTTCG | ATTTCAATTT | TGCGATCCAT | GTAGGCTTCC | CCTAAAGTTA | ACGAAGCGTT | 1620 |
| ATTCAGTAAA | TCCTTCACAG | GAATTTTTTC | ATTGAATACA | ATTTTAAAAA | CCGGATCCCC | 1680 |
| CGACCCTTGC | CCATACTCTT | TGACGGTACC | ATCCAGTAT | GTGACTTGTG | TCTTTTTTGA | 1740 |
| AAAAGACCAT | TTAAACAGTT | GACTGTACGT | TTCTTTTTCT | AACATTGCAT | TCCTCCATT | 1800 |
| AAATACCATT | TGAAGCCAAA | ACAAAAGAA | GTCGCTTTCC | GGTAGTTCGT | CAAAACAAAC | 1860 |
| ACCACAGTCC | GTTCTAAACT | GAAGCACAGA | AAAGTTATCA | CCCCTTCTAT | GTTCCGCTTC | 1920 |
| TTTTTTGCAA | TTACAGTTCT | ATTCTACTCC | TCTTTTAAAA | ATTTGAACAT | TCTTTTAACG | 1980 |
| TAATACCTAC | TATTGTTATT | CTTTATCACA | AAAAAACTAG | AGCCAGTCCT | TGACAGACTC | 2040 |
| CTCTAGTTCT | AAATATTATG | CTTTCTTACG | CATCCGTTGT | TCCGCATGAG | TGTAAGCGCC | 2100 |
| ATGCCACACG | TGCCCCACAT | AAGGATTAAC | TTGAATACCG | TGTTTAATCG | CCGCTGCTAC | 2160 |
| AAATTTTTCG | CTAAAGTTAC | TGCTTCTAAC | ACCGAATAAC | CTTTCGCCAA | GCCAGCTGTG | 2220 |
| ATTGCCGCTG | AAAAAGTACA | ACCTGCACCA | TGATTATAAT | CAGTTGGATA | TAATTCATTT | 2280 |
| TCCAAAAGAT | GCGCGGTGTG | ACCATCGTAA | AATAAGTCCA | GTGCTTTTC | ACCAGCTAAG | 2340 |
| CGATGTCCCC | CTTTAACCAC | GACATGCTTG | GCTCCCATTT | GTACAATTCG | TTTTGCCGCT | 2400 |
| TCTTCCATCT | CCGCCACGGA | AGAAATTTCG | CCTAAACCAG | ATAAGATGCC | CGCTTCAATT | 2460 |
| AAATTAGGCG | TGGCAACTAA | TGCTAATGGC | AGTAAATCGT | TTTTAGGCCT | TCCACACTTT | 2520 |
| TGGGTTGCAG | AATTTGTGCC | GTTCCCTTAC | AAGCAATGAC | TGGGTCAATC | ACGACTTTTT | 2580 |
| GAATTTTTTC | TTGTTTAATG | TACTTACTAG | CCATTTTAAT | ATTTGTTCA | TTACCCCATC | 2640 |
| ATCCCTGTT | TTCAAAGCCG | CTACTGGACC | GCCTGCAAAA | ACCGAAATCA | ATTGTTTTC | 2700 |
| TAAGAGCGTT | TCTGGCAATT | CAGTTACTTC | ATGTGACCAA | CCTGTCGTAG | GATCCATCGT | 2760 |
| CACAATCGAG | GTTAAACTTG | AAAATCCAAA | AACTCCATAC | TCTTCAAATG | TTTTTAAATC | 2820 |
| TGCTTGAATC | CCTGCCCCTC | CAGTTGAATC | GGAGCCTGCA | ATCGTCAATA | CTTTTTCCAT | 2880 |
| TAAATCACCT | AACCTTTTTC | TCCAAGTATA | CGGAAGAAAC | AAGTCTGCTA | AAACAGCCAA | 2940 |
| TTGGCTTATT | TTTTAGCCAG | CCAATTTCTA | AACAAAAAAA | AGACCAGAGA | ATAAATTCTC | 3000 |
| TGGTCTTACG | TCCGAATACC | CCAGTTTTTC | ACGCTGGTTA | AAGCTATAGT | TAAAAGTTA | 3060 |
| ATTATTTAAC | GATTTCAGTA | ACAACGCCTG | AACCTACAGT | ACGTCCGCCT | TCACGAATAG | 3120 |
| AGAAACGAGT | TCCGTCTTCG | ATAGCGATTG | GGTGAATTAA | TTCAACGTCC | ATAGCAACGT | 3180 |
| TATCACCAGG | CATTACCATT | TCAGTACCTT | CTGGCAATTC | TACAACACCA | GTAACGTCTG | 3240 |
| TTGTACGGAA | GTAGAATTGA | GGACGATAGT | TAGTGAAGAA | TGAGTGTGAC | GTCCGCCCTC | 3300 |
| TTCTTTTGAT | AATACGTATA | CTTCAGCTTT | GAATTTTGTG | TGTGGAGTGA | TTGTAGCTGG | 3360 |
| TTTAGCTAAT | ACTTGTCCAC | GTTCGATATC | TTCACGTGCA | ACACCACGTA | ATAAAGCACC | 3420 |
| GATGTTGTCG | CCTGCTTCAG | CGTAGTCTAA | TAATTTACGG | AACATTTCAA | CACCTGTAAC | 3480 |
| AGTTGTTTTA | GATGTTTCGT | CTTTAATACC | AACGATTTCA | ACTTCGTCAC | CAACGCGAAC | 3540 |

| | | | | | |
|---|---|---|---|---|---|
| TTCACCACGT | TCAACACGGC | CTGTAGCAAC | AGTACCACGT | CCAGTGATTG | AGAATACGTC 3600 |
| TTCGACTGGC | ATCATGAATG | GTTTGTCAGT | ATCACGTTCT | GGAGTTGGGA | TATATTCGTC 3660 |
| AACTGCAGCC | ATTAATTCTA | AGATTTTTTC | TTCATAAGAC | TCGTCGCCTT | CTAAAGCTT 3719 |

( 2 ) INFORMATION FOR SEQ ID NO:11:

( i ) SEQUENCE CHARACTERISTICS:
        ( A ) LENGTH: 3480 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Enterococcus faecalis
        ( B ) STRAIN: Clinical Isolate S2- 7

( x i ) SEQUENCE DESCRIPTION: SEQ ID NO:11:

| | | | | | |
|---|---|---|---|---|---|
| AAGCTTCTAG | CGTTTCGGAT | TGGCGCCTAT | GATGCACCAG | GAGAGCGACG | AATCAATACC 60 |
| AAAAATATGC | CTACAGCAGG | AGGACTTGCA | ATCTACATTG | CTTTGCTAG | TTCATGTTTA 120 |
| TTGATTTTTC | GTTCGATTAT | CCCACAAGAT | TATATTTGGC | CGATTATTTT | GGCTGGTGGA 180 |
| ATGGTTGTTT | TGACAGGCCT | CATTGATGAT | ATTAAGAGA | TTACTCCAAT | GAAAAAAACA 240 |
| ATCGGTATTT | TGTTAGCAGC | ATTAGTTATT | TTATTTTGTT | GCTGGAATTC | GGATAGATTT 300 |
| TGTGACGTTG | CCAGTTGTTG | GAATGATTGA | TTTGCGCTGG | TTTAGTTTAC | CACTAACTTT 360 |
| ATTGTGGATT | TTAGCGATTA | CGAATGCAGT | AAATTTAATT | GATGGTTTGG | ATGGTTTAGC 420 |
| ATCAGGCGTA | TCCATTATTG | GATTAACCAC | GATTGGTATT | ACAGGGTATT | TTTTCCTACA 480 |
| TGCTAAAACG | GTCTATATCC | CAATTGTTAT | TTTTATTTTA | GTTGCGAGCA | TTGCGGGATT 540 |
| TTTCCCATAC | AATTTTTATC | CGGCTAAAAT | ATTTCTAGGA | GATACCGGGG | CGTTATTCCT 600 |
| CGGGTTTATG | ATTGCAGTAA | TGTCGTTACA | GGGCTTGAAA | AATGCTACGT | TTATTACGGT 660 |
| AATTACGCCA | ATGGTGATTT | TAGGTGTGCA | ATTACGGATA | CGGTTTATGC | AATTATTCGA 720 |
| CGGCTATTGA | ACAAGAAGCC | CATTTCCTCA | GCAGATAAAA | TGCATTTACA | TCACCGCTTG 780 |
| TTATCTTTAG | GTTTTACCCA | TAAAGGGGCG | GTCATGACTA | TTTATGCATT | AGCGTTAGTT 840 |
| TTTTCCTTTG | TCTCTTTATT | GTTCAGCTAT | TCAAGTACAG | TAGCATCAAT | TTTATTAATT 900 |
| GTCTTTTGTT | TAATTGGCTT | AGAACTATTC | ATTGAACTAA | TCGGTCTAGT | TGGCGAAGGG 960 |
| CATCAACCGT | TGATGTATTT | GTTACGGATT | TTAGGGAATC | GTGAATATCG | TCAGGAGCAA 1020 |
| ATGAAAAAGC | GACTTGGCAA | GCATTCTAAG | AGAAAGTAAA | GAAATCTTTA | GGTTGCTTTG 1080 |
| CGAGAGCTAA | ACCTATGATA | TAATTCCATT | AAACTTAAAA | AAGTATATGT | GTGAAACATA 1140 |
| TGCTTTTTTT | TTAAGACGAT | GTTTCAGTAG | TAAGGAGAAA | TGAGCATGCA | AGAAATGGTA 1200 |
| ACAATCTCGA | TTGTCACTTA | TAATAGTCGT | TACATTTTA | ATGTACTAGA | CCAATTAAAA 1260 |
| GCCGAACTAG | GTACTGATAG | TATCTATGAT | ATTCATATCT | ATGACAATCA | TTCTGAAACA 1320 |
| GCGTATCTTG | AAAAATTAAC | AACATATGAA | CCATTTATTA | CTATCCATCG | CGCTGAAGAA 1380 |
| AATCAAGGGT | TTGGTCATGG | TCATAATCAA | GTGTTATTCA | ATGCTTCGAC | AAAGTATGCA 1440 |
| ATTATTTTTA | TCCCGATGTG | TTGGTTACTA | AAGACGTGCT | TGATCGTTAT | TAGACGTATC 1500 |
| AAATAGATAA | GAACATTGCA | GTCGGTAGCC | CTAAAGTTGT | TAAATGAAGA | TGGCACGACG 1560 |
| CAATATTTAG | TTCGTCAAAA | ATTAGATGTC | TTCGATTATA | TGTTACGTTT | TATTCCCTTT 1620 |
| CAATTTGTAA | AGAAAATTTT | TGATAAACGT | TTGAGTATTT | ATGAATGTCG | CGATTTGTCG 1680 |
| GATACAGAAA | CAACGGATAT | TAAAATGGGC | TCAGGCTGTT | TTATGTTGAT | TGATCGTGAA 1740 |

```
AAATTCGTTG  AAATTGGTGG  GTTCGATGAA  CGTTTCTTCA  TGTACTTTGA  AGACAACGAT    1800

TTATGTTTAC  GCTTTGGCAA  AGCAGGCTAT  CGGATTCTCT  ATACGCCTTT  TGAAACGGTT    1860

GTTCACATGT  ATGAAAAGGG  CGCCCATAAA  AGTCGAAAAT  TGTTTAAAAT  CTTTATGCAA    1920

TCAATGGGGA  AATTTTTTAA  CAAATGGGGC  TGGAGGTTCT  TTTAATGAGT  CAAAGATTAG    1980

CGGTAGTCAT  CGTCTTATAT  CAAATGAAAA  TGGCTGATAC  GCCGAATTAT  TTGTTATTAA    2040

AAGAAGTGGT  AGACCACCCC  CAATTGCACT  TATTTATTTA  TGACAACAGT  CCACTTCCTC    2100

AAGAAGATGC  ATTATTTTTA  CAACCAAATG  TTACTTATCG  ACATAATCCT  GATAATCCAG    2160

GACTAGCGAC  CGCTTATAAT  GAAGCGATTG  CTTTTAGTCA  AGCGAATCAA  TGTGAATTAT    2220

TGTTGCTCCT  TGACCAAGAC  ACAGAAGTGC  CAGCCTCTTA  TTTTGATACG  TTGATCATCA    2280

TGCCATTAGA  TCCGACTGTG  GCAGTCTATG  TTCCAATTGT  AGAAGCAAAT  GGACAACAAA    2340

TTTCGCCAGT  ATATAGTGAT  CAATACGTTG  GGCTTAAAGG  AGCAAAGCCA  ACAGCAGGGA    2400

TAGCCAACCA  ACCGTTGATG  GCTATCAATT  CTGGTACAGT  TATTACGGCA  GAAACGCTAC    2460

GCTGGTTGGA  AGGATTTTCG  GAAGAATTTC  CTTGGACTA   TTTAGACCAT  TGGTTCTTTT    2520

ATCAATTAAA  TCAAGCCAAT  AAAAGATTG   AAGTCTTACC  AATCCACCTA  AAACAAGAAT    2580

TGTCTGTTTT  AGATTATCGT  ACAATGAGTC  CTCAACGTTA  TCGCTCTATT  ATTGAAGCAG    2640

AAACGTTATT  TTATCGTCGA  TATGATCAAG  AAAAGTTTTC  CCATCATCGA  CGCCATTTAT    2700

TTTTACGCAG  TAGTAAGCAA  TTTTTAACTG  TCAAAAATCG  CCAAATTTGG  CGGCAAACAT    2760

TGGCAGAATT  TCTCAAGTTA  ATGAAAGGAT  AATCTATGAT  CTCAGTTTGT  ATTGCGACAT    2820

ATAATGGAGA  AAAATATCTC  GCGGAACAAT  TAGATAGTAT  TCTTTTACAA  GTCAGTGAAG    2880

AAGATGAACT  AATTATTTCA  GATGATGGTT  CTACTGATCA  TACGTTGGAA  ATTTTGAGGA    2940

CGTATGCAGC  GAATTATCCC  CAAATTCAAT  TGTTACAAGG  TCCCAGGGCA  AGGAGTGATT    3000

GCTAATTTTG  CATTTTGCCT  TACGCATACG  AAAGGCGAAG  TAATATTTTT  AGCAGATCAA    3060

GATGATGTTT  GGTTGCCAAA  TAAAGTAACG  ACGGTGACAG  AATATTTTGA  AGCGCACCCT    3120

GACATCCAAG  TGGTTATTAG  TGACTTGAAA  ATTGTTGATG  CGGATTTACA  AGTTACCAAT    3180

CCCTCTTATT  TAAGTTTCGA  AAAGTCAAAC  CAGGGTTTTG  GCGAAATGCG  ATAAAAAGTG    3240

GCTATATTGG  GGCAGGTATG  GCCTTTCGTC  AAGAAATGAA  AAACGTCATT  TTACCCATTC    3300

CGCCAGAAGT  TCCTATGCAT  GATATGTGGA  TTGGCTTATT  AGCTGCACGG  AAGAAGCAAA    3360

CGGGTCTCAT  TAAAGAACCA  TTAGTGCTTT  ACCGAAGACA  TGGAGCGAAT  GTCAGCCCCA    3420

TTATTACCAA  AACAAGTTTC  CAACAAAAAT  TAAATTGGCG  TGTGAATTTA  TTAAAAGCTT    3480
```

( 2 ) INFORMATION FOR SEQ ID NO:12:

( i ) SEQUENCE CHARACTERISTICS:
        ( A ) LENGTH: 2441 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Enterococcus faecalis
        ( B ) STRAIN: Clinical Isolate S2- 27

( x i ) SEQUENCE DESCRIPTION: SEQ ID NO:12:

```
AAGCTTCTGC  GCTAGGAACC  AGCCCTTTAA  TTACATCTCC  CCATACTGGA  TTTGACAATG      60

CCACTTGATA  AGCAAAAATC  ACAAAAATAA  CAACAATTAA  AGCAACAACA  ATAGCTTCAA     120
```

| | | | | | | |
|---|---|---|---|---|---|---|
| TTTTTCTAAA | ACCAATTTTT | GTCAATAACA | ACAAAAGTAA | AACATCAAAT | ACCGTAATGA | 180 |
| AGACAGCCAG | ACCTAAAGGA | ATATGAAATA | ATAAATATAA | GGCAATTGCG | CCCCCGATAA | 240 |
| CTTCAGCGAT | ATCTGTAGCC | ATAATTGCTA | ACTCTGTTAA | AATCCATAAT | ACAATACCTA | 300 |
| ACGTCTTACT | AGTTCTAGCA | CGAATCGCTT | GTGCTAAATC | CATCTGTGAA | CAATGCCTAA | 360 |
| TTTAGCAGCC | ATATATTGGA | GCAACATTGC | AATCAAACTG | GAAATTAAAA | TAATCGACAT | 420 |
| CAATAAATAT | TGAAAATTTT | GTCCCCCAGT | AATTGAAGTA | GACCAGTTTC | CTGGATCCAT | 480 |
| ATACCCCACT | GCTACCAATG | CTCCTGGACC | TGAGTAAGCA | ATAACGTTT | TCCAAAAACT | 540 |
| CATATTTTTA | GGCACGTCGA | TGGTGCCATT | AATTTCTTCA | AGCGAAGGAC | CATTTGCATA | 600 |
| TTCAATCAAA | TGATGTCTTT | GCTTTGGTTC | ATGTTCTTCT | GAATTTTTCA | ATTCAATTCC | 660 |
| TTCTTTCGTT | TTGCAATAAT | TTTAAAAGGC | CCTTCCCGTT | AGAAGGTTAA | CCTCTAGTAT | 720 |
| ATTTTAGGTA | CACCTAAAAT | ATACTGCTAA | AAATAACAAA | ATGCAAGACT | TGAAAGAAAA | 780 |
| TTTTGACAGT | GTAAAAATAG | ATTGTCGTAA | ATGTGCGATC | TTAAAGTTTG | AAGAAATCAG | 840 |
| GGTAGCTGGT | AGTTGATTAT | CTTAAGAAGT | AGAAAATAAG | GGACCTAAGT | CATTTCGGCT | 900 |
| TAGGTCCCTT | ATTTATTTT | TATTCGGTTA | TTCTATTAAG | AATGGATGCT | ACAATTTCTG | 960 |
| TCGTGTCAGC | TGAATGATTT | CTAAAATCTC | GTAAACTTAA | TCTGACGAAA | ACCTTCAAGT | 1020 |
| ACTTCGGGCA | ACTTATTTN | CCCCCATTCA | AAAGTTCCAT | CATTTCTTTT | CAATAATCTT | 1080 |
| TGTAAAATTT | CTTCTTTCTC | GACCGCTAAC | AAAAAATGAT | AAACGTCAAT | GCCTGCTCGT | 1140 |
| CTCAGATATC | CAATCAGCTC | TTCTTCATAT | TCATTTTTAT | AAAGGGTCAT | TGTAACAATA | 1200 |
| ATCGGCCGTC | CAGACTCTTT | GGACATTCGT | TTAATAAAT | GAGCATTCCA | GCAACGCCAT | 1260 |
| TCCTGATACT | CCTGAAAATC | ATTTTCTTTC | ATTCTTCGG | GAACTAGCTC | CATCAATGCA | 1320 |
| CTACCAATAA | TTTCTGGATC | ATAAATGATT | GCGTTGGGAA | GTTTTGTTG | TAACTCATGT | 1380 |
| GCAATGGTCG | TTTTTCCGGA | TCCAAACGCA | CCGTTAACC | AAATAATTAT | CATAATTTCC | 1440 |
| TTTTCTTCTG | AACAAATTTC | TTTGTTGTTT | AATTTAGGTG | CTAGATTACT | TTTAATTTTT | 1500 |
| TTAGCCATTC | ACTTATAGTT | ACTACTTACA | TCTTTAACAG | TAAACGAGAC | AAACTAAAAA | 1560 |
| TACAACATCC | TACGCTATTA | ACCTCGGGTT | ATATAACATA | CTCATCTGAT | AATTTCTCCC | 1620 |
| TAAAAAACA | GAATGTGGGC | AATCTTTTA | AGAATAATTG | AATAGAATAA | CAACAAACAG | 1680 |
| TAATTCAGGT | ATAACCAGCT | AGAAATTGTT | TTATTTTAG | TCACGAGTAT | GATAAGCATG | 1740 |
| TAAATCAAAT | AGAATCATAT | TAGGTGAGGT | TACTCTGAAG | AACACAGGTT | ATCGCTCGGA | 1800 |
| AATGTCGAGA | GACAGTAACG | AGTAAAGCAG | GGATTGTCGA | ATTAAGGCTT | TCCTAAGATA | 1860 |
| ACTAGAATTT | TTTTCTTACG | TCTCAGAAAG | CCAAAGCTCA | ATTATTGTGA | TTACCCTATA | 1920 |
| ATCTTCTTCT | TTTATTCGGC | GACCTCTTTA | ATATGATTAA | TTGGAGGTTT | TTAAATTGAA | 1980 |
| AGCTGTCACT | GCATCATCTA | AGAAAAATAC | CCTACTTGCT | AAAAGTATCG | GGAATCTTAC | 2040 |
| CTTGCTCATC | ATTTAGGCA | TTTTCATTTT | TATCATCGTC | TTCTCTTGGC | TAAAAATGAA | 2100 |
| TCGCCCTCTC | CACACCCTTC | CCTCAGAAGA | ATTCCTCGCA | ACACCAAGTA | AAACAGATGA | 2160 |
| TTTCTTATCT | CCATCAAATC | TTTTTTACTT | TTCAATTCGA | ACCATGTTTC | GAATGATTGT | 2220 |
| GGGGATGGCT | TGGTCCTTCC | TGTTTTCCTT | TGTTTTTGGT | ATTTTAGCCG | TAAAATATAA | 2280 |
| AACGGCACGA | AGAGTCATTT | TACCATTAGT | TAATTTCCTT | GAATCTGTTC | CATTGCTAGG | 2340 |
| TTTTTTGACC | TTTACAACTG | CTTGGTTACT | TGGTTTATTT | CCAGGAAATG | TGATGGGCGC | 2400 |
| AGAAGCGGTT | GCTATTTTTG | CCATCTTCAC | AGGTCAAGCT | T | | 2441 |

( 2 ) INFORMATION FOR SEQ ID NO:13:

( i ) SEQUENCE CHARACTERISTICS:
    ( A ) LENGTH: 9515 base pairs
    ( B ) TYPE: nucleic acid
    ( C ) STRANDEDNESS: double
    ( D ) TOPOLOGY: linear ( i i ) MOLECULE TYPE: Genomic DNA ( v i ) ORIGINAL SOURCE:
    ( A ) ORGANISM: Pseudomonas aeruginosa
    ( B ) STRAIN: Clinical Isolate P2-2

( x i ) SEQUENCE DESCRIPTION: SEQ ID NO:13:

```
AAGCTTTCCT  CCAGACCCTT  CACCGCCGTG  GAGATCGACG  GCTGGGCGAT  GTACAGCTTG     60
CGCGAGGCCT  CGGCCACGCT  GCCGCATTCC  ACGGTGGTCA  CGAAATACTT  GAGTTGCCGC    120
AAGGTATAGG  ACGCCACTGC  AAGACCTCAT  CGGCGCATCA  TCCTCCCCGG  GCCGGGCGTG    180
CGCGCCTCGA  TTGTTGTGTC  CGCCGCGCTG  CAAGCAAGTT  GCAGGCCGCT  GCCGAGCGTC    240
GCGCGCTGGC  CGCGGAACGA  TTGCCCGCCT  GCACGATAAC  CCAGCACGAC  GCACTTTGCC    300
GGGGCACGCC  TGGCCAGCTT  TTTCTTATGT  CCCGAGGACA  TTTTTAATAA  TTTTCCTTCG    360
CCGCGGCTTG  CGCGACCATC  CTTCCCCATC  GACCCCATGG  ACAGCGGTTC  GCCTCCCGGC    420
GGTCCGGGCC  ATGCGTGCAG  AACCACGACC  GGCGCAGACC  GGCGAGATAA  CAAGGAGAAG    480
GTGGGGTGTT  CGAACTCAGC  GATTGGCAAC  GGCGCGCCGC  GACACAGCGC  TTCATCGACC    540
AGGCCCTGAT  CGGCGGCCGC  CAGCGTCCAG  CCGCCAGCGG  CGCTACCTTC  GACGCCATCG    600
ATCCGGCGAG  CAATCGCCTG  CTGGCGCGGG  TCGCGGCCTG  CGATGCGGCC  GACGTCGACG    660
CGGCAGTGGC  CGCCGCCCGC  CGCGCCTTCG  ACGAAGGCCC  CTGGGCGCGT  CTCGCCCCGG    720
TCGAGCGCAA  GCGCGTGCTC  TGCGCCTGGC  CGAGCTGATG  CTGGCCCATC  GCGAAGAGCT    780
GGCGCTGCTC  GACTCGCTGA  ACATGGGCAA  GCCGGTGATG  GACGCCTGGA  ACATCGATGT    840
ACCCGGCGCC  GCCCACGTCT  TCGCCTGGTA  TGCGGAAAGC  CTCGACAAGC  TCTACGACCA    900
GGTCGCGCCG  GCCGCCCAGC  AGACCCTGGC  CACCATTACC  CGCGTGCCGC  TGGGGGTGAT    960
CGGCGCGGTG  GTGCCGTGGA  ACTTCCCGCT  CGACATGGCC  GCCTGGAAGC  TCGCCCCGGC   1020
CCTGGCCGCC  GGCAACTCGG  TGGTGCTCAA  GCCGGCCGAG  CAGTCGCCGT  TCTCCGCCCT   1080
GCGCCTGGCC  GAGCTGGCCC  TGGAGGCGGG  GGTGCCGGAA  GGCGTGCTGA  ACGTGGTGCC   1140
GGGCCTCGGC  GAGCAGGCCG  GCAAGGCCCT  CGGCTTGCAC  CCGGAGGTGG  ACGCACTGGT   1200
GTTCACCGGC  TCCACCGAGG  TCGGCAAGTA  CTTCATGCAG  TATTCCGCGC  AATCCAACCT   1260
CAAGCAGGTC  TGGCTGGAGT  GCGGCGGTAA  GAGTCCGAAC  CTGGTGTTCG  CCGATTGCCG   1320
CGATCTTGAC  CTGGCGGCGG  AAAAAGGCGC  CTTCGGCATT  TTCTTCAATC  AGGGCGAGGT   1380
CTGTTCGGCG  AACTCGCGCT  TGCTGGTGGA  GCGTTCGATC  CACGACGAGT  TCGTCGAGCG   1440
CCTGCTGGCC  AAGGCCCGCG  ACTGGCAGCC  GGGCGATCCG  CTGGACCCGG  CCAGCCGCG    1500
CCGGCGCCAT  CGTCGACCGC  CGGCAGACCG  CCGGGATTCT  CGCCGCCATC  GAGCGGGCGC   1560
AAGGCGAGGG  CGCGACCCTG  CTCGCGGTGG  CCGCCAGTTG  ACGATCAACG  GTTCGGACAA   1620
CTTCATCGAA  CCGACCCTGT  TCGGCGACGT  ACGCCCGGAC  ATGCAGCTGG  CCCGCGAGGA   1680
AATCTTCGGC  CCGGTGCTGG  CGATCAGCGC  CTTCGACTCC  GAGGACGAGG  CCATACGCCT   1740
GGCCAAGGAC  AGCCGCTACG  GCCTCGCCGC  CTCGCTGTGG  AGCGACGACC  TGCACCGTGC   1800
GCACCGGGTG  GCGCGGCGCT  TGAATGCCGG  AACGTGTCGG  TGAATACCGT  GGACGCGCTG   1860
GACGTCGCGG  TGCCTTTCGG  CGGCGGCAAG  CAGTCCGGCT  CGGTCGCGA   CCTGTCGCTG   1920
CATTCCTTCG  ACAAGTACAC  CCAGTTGAAG  ACGACCTGGT  TCCAGTTGCG  CTGAAGACGC   1980
```

```
GACGGACGCG  ACACGACTCG  ATGCCGATAA  CGACAACAAG  AGGACGATCG  AATGAACGAC   2040
ACGCCGAACG  TGCGTGAGCC  GGCCCTGCGC  CGCGTGCTCG  GGCTGGGACC  GCTGCTGGCG   2100
GTGGCCATCG  GCCTGGTGGT  TTCCCAGGGC  GTGATGGTAC  TGATGCTGCA  AGGCGCCGGG   2160
ACGGCCGGCC  TGGGCTTCAT  CGTGCCGCTG  GGAGTGGCCT  ACCTGCTGGC  GCTGACTACG   2220
CCTTTTCCTT  TTCCGAGCTG  GCCCTGATGA  TTCCCCGCGC  CGGTAGCCTG  AGCAGCTACA   2280
CCGAGGTGGC  CATCGGGCAT  TTCCCGGCGA  TCCTGGCGAC  CTTTTCCGGC  TACGTGGTGG   2340
TGGCGATGTT  CGCCCTCTCG  GCGGAACTGC  TGCTGCTCGA  CCTGATCATC  GGCAAGGTCT   2400
ACCCCGGCGC  GCTGCCGCCG  ATGCTGGTGC  TACGGCGTGC  TCGGCCTGTT  CACCCTGCTC   2460
AACCTGCTCG  GCATCGACAT  CTTCGCGCGC  CTGCAGAGCG  CGCTGGCGCT  GCTGATGATG   2520
ATCGTCCTGC  TGGTGCTCGG  CCTGGGTGCG  GTGAGCAGCG  ACCACGCTTC  CGCGCAGACC   2580
GCCCTGGCGA  GCGGCTGGAA  CCCGCTGGGG  GTAAGCGCCC  TGGCGCTCAC  CGCGATGGCC   2640
GTGTGGGGCT  TCGTCGGCGC  CGAGTTCGTC  TGCCCGCTGG  TGGAGGAGAC  GCGGCGTCCG   2700
GAGCGCAACA  TCCCGCGTTC  GATGATCCTC  GGCCTGAGCA  TCATCTTCCT  GACCATCGCC   2760
CTCTACTGCT  TCGGTGCGCT  GCTGTGCATC  CCGCAGGCGG  AACTGGCCGG  CGACCCGCTG   2820
CCACACTTCC  TCTTCGCCAA  CCGCGTGTTC  GGCGAGTACG  GCCAGCTGTT  CCTGGTGATC   2880
GCCGCGATCA  CCGCCACCTG  CAGCACCCTC  AACTCGTCGC  TGGCGGCGAT  CCCGCGGATG   2940
CTCTACGGGA  TGGCGCAGAA  CGGCCAGGCC  TTCCCGCAAT  TCAAGCAGCT  CAGCCGGCGG   3000
GCGCGCACGC  CCTGGGTGGC  GGTGCTGTTC  GTCGCCGCGA  TCACCGGCCT  GCCGATCCTG   3060
ATCCTCGGCC  AGGACCCGGA  CTCGATCAAC  CTGCTGCTGC  TCGCCGCCGC  GCTGGCCTGG   3120
CTGCTGGCCT  ACATCATCGC  CCACGTCGAC  GTGCTGGCCC  TGCGCCGTCG  CTATCCGCAC   3180
ATCGCCCGTC  CGTTTCGCAC  GCCGTTCTAC  CCGCTGCCGC  AACTGTTCGG  CATCGCCGGG   3240
ATGATCTACG  CGGTGGTCCA  CGTCTCGCCG  ACCCCGGAAA  TGACCGGACG  GATCTTCGCC   3300
AGCGCCGGCG  TGGTGCTCGG  CGTGGTCTCG  CTGGTGGCGG  TGGTGTGGAT  CAAGGGCGTG   3360
ATGCGCAAGC  CCCTCTTCGT  ACCCGAACCG  CTCGAGACGG  CCGGTGAGAC  TGCCCAGGGC   3420
AAGTCCGTCG  CCCTCGATCC  CCTGCAATCC  CTTCGGCCTG  ACGCGCCAAG  GGAACAAGGA   3480
GAACACAGAC  GATGACCGCT  CAGCTCAACC  CGCAGCGCGA  CACCCGCGAC  TACCAGCAAC   3540
TGGACGCCGC  GCACCACATC  CACGCCTTCC  TCGACCAGAA  GGCGCTGAAC  CGCGAAAGGC   3600
CCGCGGGTGA  TGGTCCGCGG  CGATGGCCTG  CAGCTCTGGG  ACAACGACGG  CAAGCGCTAC   3660
CTGGACGGCA  TGTCCGGCCT  CTGGTGTACC  AACCTCGGCT  ACGGCCGCCA  GGACCTCGCC   3720
GCCGCCGCCA  GCCGCCAGCT  GGAACAACTG  CCGTACTACA  ACATGTTCTT  CCACACCACC   3780
CACCCGGCGG  TGGTGGAGCT  TTCCGAGATG  CTCTTCAGCC  TGCTGCCGGA  CCACTACAGC   3840
CACGCGATCT  ACACCAACTC  CGGCTCCGAG  GCCAACGAGG  TGCTGATCCG  TACCGTGCGG   3900
CGCTACTGGC  AGATCCTCGG  CAAGCCGCAG  AAGAAGATCA  TGATCGGCCG  CTGGAACGGC   3960
TACCACGGCT  CGACCCTGGG  CAGCACCGCG  CTCGGCGGGA  TGAAGTTCAT  GCACGAGATG   4020
GGCGCATGCT  GCCGGACTTC  GCCCACATCG  ACGAACCCTA  CTGGTACGCC  AACGGCGGCG   4080
AGCTGAGCCC  GGCCGAAGTT  CGGTCGCCGC  GCGGCGCTGC  AACTGGAGGA  GAAGATCCTC   4140
GAACTGGGCG  CGGAGAACGT  CGCCGCCTTC  GTCGCCGAGC  CCTTCCAGGG  CGCCGGTGGC   4200
ATGATCTTCC  CGCCGCAAAG  CTATTGGCCG  GAGATCCAGC  GCATCTGCCG  GCAGTACGAC   4260
GTGCTGCTGT  GCGCCGACGA  AGTGATCGGC  GGCTTCGGCC  GCACCGGCGA  ATGGTTCGCC   4320
CACGAACACT  TTCGCTTCCA  GCCGGACACC  TTGTCCATCG  CCAAGGGCCT  GACGTCCGGC   4380
```

| | | | | | | |
|---|---|---|---|---|---|---|
|TACATCCCCA|TGGGCGGCCT|GGTACTCGGC|AAGCGCATCG|CCGAGGTGCT|GGTGGAGCAG|4440|
|GGCGGGGTGT|TCGCCCACGG|CCTGACCTAT|TCCGGCCACC|CGGTGGCGGC|GGCGGTGGCC|4500|
|ATCGCCAACC|TCAAGGCTGC|GCGACGAGGG|CGTGGTCACG|CGGGTCAGGG|AGGAGACCGG|4560|
|CCCCTACCTG|CAACGCTGCC|TGCGCGAGGT|CTTCGGCGAC|CATCCGCTGG|TCGGCGAGGT|4620|
|CCAGGGCGCC|GGCTTCGTCG|CCGCGCTGCA|GTTCGCCGAG|GACAAGGTGA|CCCGCAAGCG|4680|
|CTTCGCCAAC|GAGAACGATC|TGGCCTGGCG|CTGCCGCACC|ATCGGCGGCT|TCGAGGAGGG|4740|
|CGTGATCATC|CGCTCCACCC|TCGGCCGCAT|GATCATGGCC|CCGGCGCTGG|TGGCCGGGCG|4800|
|TGCCGAGATC|GACGAACTGA|TCGACAAGAC|CCGTATCGCG|GTGGATCGCA|CCGCGCGCGA|4860|
|GATCGGCGTG|CTCTGACGCG|CCCCGGCGGC|CCGGCCTCGG|CCGGGTCGCC|TGCGACACGG|4920|
|AGCGTCCCCC|CATAACGACG|ATGCGGCGCC|TGGCGACCGC|GCGCGGAACC|GTTTCGGCCT|4980|
|CTGGCGGCAA|CTGCCTAAGC|AACATCACAA|CAATGCCAAT|CGGCTGTGGG|AGTGTTCCAT|5040|
|GTTCAAGTCC|TTGCACCAGT|ACGCACACGT|GTTTTCCCGG|TTGTCCCTGT|TCGTCCTGGC|5100|
|GTTCGCCGCG|GCGGCCCAGG|CGCAGAGCCA|GAGCCTGACG|GTGATCTCCT|TCGGCGGCGC|5160|
|GACCAAGGCC|GCCCAGGAAC|AGGCCTATTT|CAAACCCTTC|GAGCGAAGCG|GCGGCGGGCA|5220|
|GGTGGTCGCC|GGCGAATACA|ACGGCGAAAT|GGCCAAGGTG|AAGGCCATGG|TCGACGTCGG|5280|
|CAAGGTCAGC|TGGGACGTGG|TCGAGGTGGA|GAGCCCCGAA|CTGCTCCGCG|GCTGCGACGA|5340|
|GGGGCTGTTC|GAACGCCTCG|ACCCGGCGCG|TTTCGGCGAC|CCCGCGCAGT|TCGTCCCCGG|5400|
|CACTTTCAGC|GAGTGCGGGG|TGGCCACCTA|CGTCTGGTCG|ATGGTGATGG|CCTACGACTC|5460|
|GACGAAGCTG|GCCAGGGCGC|CGCAGTCCTG|GGCGGATTTC|TGGAACGTCC|GCGAGTTCCC|5520|
|CCGGCAAGCG|TGGCCTGCGC|AAGGGCGCCA|AGTACACCCT|GGAAGTGGCG|TTGCTGGCCG|5580|
|ACGGGGTGAA|GGCGGAGGAC|CTCTACAAGG|TACTCGCCAC|CCCGGAGGGG|GTCAGCCGCG|5640|
|CCTTTCGCCA|AGCTCGACCA|GCTCAAGCCG|AACATCCAGT|GGTGGGAGGC|CGGCGCCCAG|5700|
|CCGCCGCAAT|GGCTGGCGG|CGGCGACGTG|GTGATGAGCG|CGGCCTACAA|CGGGCGCATC|5760|
|GCCGCTGCGC|AGAAGGAGGG|GGTGAAACTG|GCCATCGTCT|GGCCCGGCAG|TCTCTACGAT|5820|
|CCGGAGTACT|GGGCGGTGGT|GAAGGGCACC|CCGAACAAGG|CGCTGGCGGA|GAAATTCATC|5880|
|GCCTTCGCCA|GCCAGCCGCA|GACGCAGAAG|GTGTTCTCCG|AGCAGATCCC|CTACGGGCCG|5940|
|GTACACAAGG|GCACCCTGGC|GTTGCTGCCG|AAGACGGTGC|AGGAGGCGCT|GCCGACCCGC|6000|
|GCCGGCCAAC|CTCGAAGGCG|CGCGGGCGGT|GGATGCCGAG|TTCTGGGTGG|ACCACGGCGA|6060|
|GGAGCTGGAA|CAGCGTTTCA|ATGCCTGGGC|GCGCGCTGAG|CGCTGCGCGT|CGGCAAAAAA|6120|
|AATGACGGGC|CCCAAGTCGT|CCGGGCCCGT|CGGGTCAAAG|CGCTGACGGG|GTGATCAGCG|6180|
|CAGCTCTTCC|AACAACCCCT|GCAGATACCG|ACAGCCCTCG|GTATCCAGCG|CCTGCACCGG|6240|
|AAGGCGCGGC|GCCCCCACCT|CCAGGCCGGA|GAGGCCCAGG|CCGGCCTTGA|TGGTGGTCGG|6300|
|CAGGCCCCGG|CGGAGGATGA|AGTCGAGCAG|CGGCAACTGC|CGGTAGAACA|GCGCGCGGGC|6360|
|CTTCTCCAGG|TCGCCGTCGA|GCACCGCCTG|GTAGAGCTGG|CCGTTGAGCG|TCGGGATCAG|6420|
|GTTCGGCGCG|GCGCTGCACC|AGCCTTTCGC|GCCGGCCACG|AAGGCCTCCA|GCGCCAGCGC|6480|
|GTTGCAGCCG|TTGTAGAAGG|GCACCCGGCC|TTCGCCGAGC|AGGCGCAGCT|TGTGCATGCG|6540|
|CTGGATGTCG|CCGGTGCTCT|CCTTGACCAT|GGTCACGTTG|TCCACTTCGC|GGACGATGCG|6600|
|CAGGATCAGT|TCCACCGACA|TGTCGATGCC|GCTGGTGCCC|GGGTTGTTGT|AGAGCATCAC|6660|
|CGGCACGCCG|ATGGCTTCGC|CAACCGCGCG|GTAGTGCTGG|AACACTTCCG|CCTCGTTGAG|6720|
|CTTCCAGTAG|GAGATCGGCA|GGACCATCAC|CGCCTCGGCG|CCGAGGGATT|CGGCGAACTG|6780|

```
CGCGCGGCGC  ACGGTCTTGG  CGGTGGTCAG  GTCGGAGACG  CTGACGATGG  TCGGCACGCG   6840
ATGGGCGACG  GTCTTCAGGG  TGAAGTCGAC  CACCTCGTCC  CATTCCGGGT  CGCTCAGGTA   6900
GGCGCCTTCG  CCGGTGCTGC  CGAGCGGGGC  GATGGCGTGC  ACGCCGCCGT  CGATCAGGCG   6960
CTCGATGGAG  CGGCCGAGGG  CCGGCAGGTC  GAGACCGCCG  TCGGCGCCGA  AGGGGGGTGA   7020
TGGTGTAGCC  GATGATGCCG  TGGATGGATG  CGGACATTGG  ATGTACCCGT  GACATTGAGT   7080
GGGAAATGCC  AGGACGGACC  TGGTGGGAAA  GGTCGTTCAG  CTCAGGCAGT  CGCTGTTGCG   7140
CGGCAGGCAG  CGCCGGGCGT  AGTAGTTGAA  TGCGGCGCCG  TGGCGCTTCG  GGGTGGAGAT   7200
CCAGTCGTGG  GCCTCGCGCG  CCAGGGCCGG  CGGGATCGGC  TTGATCTCTC  CGGCGGCCAT   7260
CGCCAGCAAC  TGCATCTTCG  CCGCGCGCTC  GAGCAGCACC  GCGATCACGC  AGGCCTCCTC   7320
GATGCTCGCA  CCGGTGGCCA  GCAGGCCGTG  GTGGGAGAGC  AGGATGGCGC  GCTTGTCGCC   7380
GAGGGCGGCG  GAGATGATCT  CGCCTTCCTC  GTTGCCTACC  GGCACGCCCG  GCCAGTCCTT   7440
GAGGAAGGCG  CAGTCGTCGT  ATAGCGGGCA  AAGGTCCATG  TGCGAGACCT  GCAGCGGTAC   7500
TTCCAGGGTC  GACAGCGCGG  CGATGTGCAG  CGGGTGGGTG  TGGATGATGC  AGTTGACGTC   7560
CGGGCGGGCG  CGATAGACCC  AGCTGTGGAA  GCGATTGGCC  GGATTCGCCA  TGCCGTGCCC   7620
GTGGAGGACG  TTGAGGTCTT  CGTCGACCAG  CAGCAGGTTG  CCGGCGCTGA  TCTCGTCGAA   7680
GCCCAGGCCC  AGTTGCTGGG  TGTAGTAGGT  CCCCGCCTCC  GGGCCGCGCG  AGGTGATCTG   7740
CCCGGCGAGC  CCGGAGTCGT  GGCCGGCCTC  GAAGAGAATC  CGGCAGGTCA  GGGCCAGCTT   7800
TTGCCGGTCA  GTCCACGTAT  TATCGCCGAG  GCTGCTTTTC  ATCTGCTTCA  GCGCGTGCTG   7860
GATCAGTTGA  TCCTTGGGTA  ATTCCAGTGT  CGTAACCATG  CGAGGTTCCT  TTGACGGAGC   7920
GAGTCGGGGG  AAACGCCAGG  CAGTTGCGCG  CCACGCAACG  ACCCGGCTGT  AAATGACACG   7980
GATCAAGTTA  TATGACACAA  AGTGTCATTT  AGCAAGAGAG  AAGTTTCATC  GCCATCGGGA   8040
GAAGGCTGTC  CTCAATGTCC  ATGCGCTTGA  AATTGCTGAG  AAAAAAACTC  GGGGTCACGC   8100
TGGAGACCCT  GGCCGACAAG  ACCGGCCTGA  CCAAGAGCTA  CCTGTCCAAG  GTCGAGCGCG   8160
GGCTGAACAC  GCCGTCCATT  GCCGCCGCGC  TGAAGCTGGC  GAAGGCGTTG  AACGTGCAGG   8220
TGGAGGAGCT  GTTCTCCGAG  GAAAGCGACG  GTGTCGACGG  CTACAGCATC  GTTCGTCGCG   8280
ACCAGCGCAA  GTCGCTGTCC  AGCGGCGACG  ACGGCCCGGC  CTACGCCTCC  CTCGTCGCAG   8340
CAGATCGGCG  CCCGCGCGCT  GTTGCCGTTC  ATCGTCCACC  CCCCGCGCGA  TTTCAGTCAC   8400
TCGACGTTCA  AGGAGCACCT  CGGCGAAGAG  TTCATCTTCG  TCCATGAGGG  CCAGGTCGAG   8460
GTCGACTTCA  TGAACCAGCG  GATCATCCTC  GAGCGCGGCG  ACGCCCTGCA  TTTCAACGCA   8520
CAGAAGCCGC  ACCGCATCCG  CTCCCTGGGG  GAGACCCAGG  CGGAATTGCT  GGTGGTGATC   8580
CACAGCGACG  AATGAGGCGA  CGGCTTCGGT  CGATCGGATG  CTTGCTAACG  TTCTGTTCGA   8640
TTATCGAACT  GTTAATCGAT  TATCGGATTG  TGAGCCCTCG  GACCCCGGCG  TAAGGTTCTC   8700
GTCACGTGCC  GTCCAGGCAG  CGCACAACAA  GACGAGACCC  GACCGATGGC  TGAAATCCTC   8760
TCCCTGCGCG  AACGGTGCGA  CGCTTCGTCC  ACGATGGCGA  CAGCGTCGCC  CTCGAAGGCT   8820
TCACTCACCT  GATCCCGACG  NCCGCCGGCC  ACGAGCTGAT  CCGCCAGGGC  AGGAAAGACC   8880
TGACGCTGAT  CCGCATGACT  CCCGACCTGG  TCTACGACCT  GCTGATCGGT  GCAGGCTGCG   8940
CGAAGAAGCT  GGTGTTCTCC  TGGGGCGGCA  ACCCCGGTGT  CGGTTCGCTG  CACCGCCTGC   9000
GCGACGCGGT  GGAGAAGGGC  TCGGCCGCAA  CCGCTGGAGA  TCGAGGAACA  CAGCCACGCC   9060
GACCTCGCCA  ACGCCTATTT  TGCCGGCGCC  TCCGGGCTGC  CCTTCGCGGT  NTGCGCGCCT   9120
ACGCCGGCTC  CGACCTGCCG  AAGGTCAACC  CGCTGATCCG  CAGCGTCACC  TGCCCGTTCA   9180
```

```
CCGGCGAAGT  GCTGGCGGCG  GTGCCCTCGG  TGCGTCCGGA  CGTCAGCGTG  ATCCACGCGC      9240

AGAAGGCCGA  CCGCAAGGGC  AACGTGCTGC  TCTGGGGCAT  CCTCGGCGTG  CAGAAGGAAG      9300

CGGCCCTGGC  GGCGAAGCGC  TGCATCGTCA  CCGTCGAGGA  GATCGTCGAC  GAACTGGACG      9360

CCCCGATGAA  CGCCTGCGTC  CTGCCGAGCT  GGGGCGCTCA  GCGCCGTGTG  CCTGGTGCCC      9420

GGCGGCGCGC  ATCCGTCCTA  TGCCCACGGC  TACTACGAGC  GCGACAACCG  CTTCTACCAG      9480

GACTGGGACC  CGATCGCCCG  CGACCGCGAA  AGCTT                                  9515
```

(2) INFORMATION FOR SEQ ID NO:14:

(i) SEQUENCE CHARACTERISTICS:
        (A) LENGTH: 2471 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Pseudomonas aeruginosa
        (B) STRAIN: Clinical Isolate P2-7

(xi) SEQUENCE DESCRIPTION: SEQ ID NO:14:

```
AAGCTTGTTC  CAGGCCCTCG  ACCGCTGCGA  TCTTCTGCGG  GTAGGCGGCG  ATGGTCTGTT        60

CGGAGTTCGC  CAACTGCAGG  CGACGCTGCG  CCAGCTGCGC  CGCCTGCACG  CCGGCAAGCA       120

TCAGGTCCTG  ATCGAGCGAG  GGGTTGAAGC  CGCGCACGAA  CTCGCTGAAC  TGGTCCACGC       180

CGAACAGGGT  GGCGATGAGC  TGGCGCTGAT  CGCTCGGGGT  CCGCGCGGCG  ATTCGGGCGA       240

AATCGTCGAG  GCGGTTCTTC  TCGATGAAGC  AGAAGCGATA  CTCAGCTTCG  TCGGGCTGGA       300

CGGCCTGCGC  CTCGCCCGCN  GCCGTAGACG  ACAGGACTGG  CGCGATGTGG  CGGCGCAGGC       360

GAGCGTTGTT  GCAGTACGTC  CGCTGGTCGA  CCGCTTGGCC  TGCGCTTCGC  TGATCGAACC       420

GAGCATCGCC  ACTTCCAAGG  CTTCGCAGAA  GCTGCTCTTG  CCGGTGCCGT  TGGCACGTNA       480

GACCAAGGTG  ATGTCATGGC  TGAGGTCGAA  CGTCTCCTGC  CGCATGAATC  CTCGAAACGG       540

CCCGACTTCG  AGCTGGTGCA  GTCGCCCGAG  CGCCGGCCCG  TTTTCGGGGC  CGCGCGCGTC       600

CCCGTCGTAG  GCGACAGGCA  TCTGCGCCAA  GATGCGCGAT  GGCCAGCGGC  GCCAAGCCGC       660

GTGGGAGCGC  CCCCCGGCGT  GCAGCACCGA  CCTCGGCCAG  TGGCTGCAGG  TGATCGAGCA       720

CCAGGGTGCG  CCAGCCGGCG  CACCGTTTCG  TCGTGCACGT  GCCGCTGCGT  CAAGTGCGCC       780

AGGAACCGGT  GGTACTCCGA  ACGTATGCTT  GCCACAGCGA  CCCCTCACTT  GGTCAACCAC       840

TGACCGTAAG  CCTCCACATC  GATCATGGGG  ACCGTTCCAC  TGAACTGAAG  CTGCGCGATC       900

AGCTTGAAAA  GAAACGCGGT  CGCCGGCTTG  TTTTCGTTGG  TGTAGCTGTA  CGCGCCGCTG       960

GCTTGGTCAT  AGAAAAGTG   CCCGTGGGCG  GCAACGCATC  CGATGTCCAG  ACGCCCTCG      1020

GTGAGGTTTG  CGTTCAGCGC  CTTGTCCATG  GATGGGCCCA  ATGCAGGACT  CCATTCGCTC      1080

TCGAAGGTGA  GCAAGCCACC  CAGAATCGGA  ATCAACGCTT  CGCTGGGTAG  GTCCCGCCAG      1140

CGTGCGGGAT  CGGCAGGCTC  GTGCGGTGCA  GCCTGCGCAC  ACTGGCGACC  TTCTCCTGGC      1200

ATAGCCACAA  GCCCGCGTC   AGCCGTCTGC  TTGGCCTCGA  ACACGGCGTA  CACGCTTTCG      1260

GCTGGAATGA  TCGTCTCGTT  CTCGTAGGTG  AAGATAAAAG  GCGAATATTG  CCGATCAAAC      1320

ACCACCACAT  CGATCTGCTG  GCTGAAGTTC  CCCAGGCTGT  CCACCACATG  CGCCTTCGCC      1380

GCCTGGTACC  GTTTGGGCAG  ATAGGTATCC  AGCATGTCGA  TCCAGACGTT  CTCGCTCGCA      1440

TCCCCCTTCG  TACCCGGGTG  ACCGAAGGTC  TTGCGTACTA  CGGACAAGCG  CTGCTGGATG      1500
```

-continued

| | | | | | |
|---|---|---|---|---|---|
| TCTTCATGCA | GGGACGACAG | GAGCTGGGAA | AGCGACCACT | GGGACATGCT | GTACCTCGAT | 1560 |
| GGGACGTGTA | TGGAAGCCGA | TGGAATCAGG | ACAGTGGGAA | CTTGGGGCCA | AACAGTGCGC | 1620 |
| GCCAGGGCGA | AGCGCTTCGA | TATTGCGACC | ACGACGCGTG | TGGTCGATGG | CGATGCTTGC | 1680 |
| GTCCTGGCTC | GCCTGGAACA | GCAGCTGCTN | GCGNGCGCTG | CTTGCGCGCG | GCATCCATAT | 1740 |
| CGTTGCTGAT | CGCCGGGCCA | AGTCCGGCGG | GATCCGGCCA | CTCGTCATGA | ACACGATCGG | 1800 |
| CAAGCGTGGC | AAAGAACGAC | TGGATCTCGC | GATCGAACGA | TCCTCCCCAG | CCGCCGTAAA | 1860 |
| GACACTCAAG | GGCCATTACC | TCGATCAGGA | ACGAGGGCTT | CACCGGCTTC | TGATCGCCGT | 1920 |
| GCTTGGGATT | GTTGTTCCAG | TACTTCACCA | TGCGCACGAG | ACCTTTCCAC | TCATTGCCAT | 1980 |
| AGGCTTGGTG | CGCTGCGGTC | GCCTTGTCCT | TATGGATCTC | CGGGTCCGTC | TTGATCCACT | 2040 |
| TTCCGGACGC | CGTATCGGGG | ATCTCATACT | GGTCGCCGGT | GTCGAATGCG | GGCACCGCAT | 2100 |
| CCACGCTGAC | CACCCGGTAG | TCCGTGTTGT | CCTCCGCGTC | GATGTGAACA | CCGAAATCCA | 2160 |
| CGTTGATCGA | GNGCGCCTGT | TTGCGCACGG | CCGCCGAACC | GTATTCTCC | ACCAATGCAG | 2220 |
| AGTGGAAATC | ATCCAGCACT | ACCGATGCGG | CCTTGCCGTG | GTAATGCTTC | TCCGAGTCCT | 2280 |
| TCAGCACGAA | GAAGATGTCG | ATATCCTTGA | GCGGCTTCGT | CTTCGTGTAT | CGAGCATAGG | 2340 |
| ACCCGGTCAG | GAACTGCGCG | CAATGCCGAA | CTTGGTCTGC | AGGTAGTCCC | GCACTTCGTT | 2400 |
| CTGGCGTTGC | GAGGCATTCT | TCTGCTCGCG | TTCGTTGAGT | TCCAGACGCG | ACTTGAACTT | 2460 |
| GCGAAAAGCT | T | | | | | 2471 |

( 2 ) INFORMATION FOR SEQ ID NO:15:

( i ) SEQUENCE CHARACTERISTICS:
        ( A ) LENGTH: 5247 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Pseudomonas aeruginosa
        ( B ) STRAIN: Clinical Isolate P2- 17

( x i ) SEQUENCE DESCRIPTION: SEQ ID NO:15:

| | | | | | |
|---|---|---|---|---|---|
| AAGCTTCGAG | GGGGCTGGGC | GAGGATCGAC | CGGCCCCGCT | CGTGTCGGAA | GGGAAGGCCA | 60 |
| GGGCTGGCCT | GCCCGTTCGG | CGCTTCGGCA | GGCTGGCGCA | GAACGATGCA | AGGTCGTTCG | 120 |
| GGTCAGCATC | AGGGATGAAA | TGACTGACAG | GAGTCGGGAT | GCTGCGTTAC | GTCGTGGGTT | 180 |
| TTCTCGCGTT | CACCGTGCTG | GCGGCCTATC | TGTTGCTGGG | GGTTTCCCAG | CACGCCTTCC | 240 |
| TGCCGTGACC | GGTCGGCATG | GCGGCTTCAG | CTGCGTTGCG | GAAGAGGCTG | TGGCGGCCGT | 300 |
| GCGGGATGCC | GGTTTTCGGC | TTGCCGTGCC | TTGCGTTGCA | GGCGTCGCGC | CGACGCGGCA | 360 |
| CGCCAGGGAA | GGCCCACAGG | GTGACGCCGG | CGAGGCCCAG | CCAGGCGACG | ATCAGCAATG | 420 |
| TGACGAAGGA | TTCGGGAGTC | ATGGTTCGTC | CTCCTCTTAC | CCAAGGATAG | ACCCTGCGGG | 480 |
| AAGGGGAATT | ACTGCAATCG | GTCTTCGACC | ATGGTCTGAA | ACGCGGTCAC | TCGGGGCCGG | 540 |
| CGCCGACCAG | GGCCAGGCAG | CCGGTGAGGC | TGGTCAGCAG | GGGCAGGGCG | AGCAGGAAAG | 600 |
| CCAGCCAGAT | GGCCTCCATG | CGCAACAGCG | TGGCGCCGAG | GAACAGCGCG | ACCAGGAGGA | 660 |
| TGGTCATGAG | CAGGGCGGTC | CAGCCGAAGT | ACATGGCGAA | GTTGTCGATG | CCCAGGCCGA | 720 |
| TGCCCCAGCC | CAGCAGCAGG | GCCCATACCC | CGGCCAGAGC | CAGGCCGAGG | CCAGCATGC | 780 |
| TCGCCAGGGT | CCGGGCGGAC | GGGGCATGCA | GCGGGTGGTT | GCGGAATAGC | TCGTAGAAGA | 840 |
| TCGGCGTATT | CATCGGCGTC | ACCTCCGCAG | GGGAACTTCC | AGCCTAGTCC | AGCGGGCGAG | 900 |

```
ACGGCCCTAG ACCTATTTGT CATTACGAGG CGTGACCTCA GGCCGTTAAC ATCCATCTTT    960
TTCCAGGCGA TGCCGTGCAT CGGGCTGCGG GCCCGCTCAC CGTTCGTCGC GCTGAGTCGA   1020
AAAAGAAACC GAAAGGGTTG CGTGCATGAG TTGGCGAACT CGCCTCGTTC GAGGTGGATG   1080
GGTATCAACT GGTCTATCAG GACCTGGGTG AAGGCACGCC GGTGCTACTG GTCCACGGTT   1140
CGCTGTGCGA CTACCGCTAC TGGCAATGGC AGTTGCGCAG CTCGGCAAGC ACCACCGGCT   1200
GATCGTGCCG AGCCTGCGTC ACTACTACCC CGAGCGCTGG GACGGGCAGG GTGCGGACTT   1260
CACCAGCGCC CGCCACGTCG CCGACCTGCT GGCGCTGGTC GAGCGGCTCG GCGAGCCGGT   1320
ACACCTGCTC GGCCATTCCC GTGGCGGCAA CCTGGCGTTG CGCCTGGCGC TGGCCGCTCC   1380
GGACGCCCTG CGTTCGCTGA GCCTGGCCGA TTCCCGGCGG CGACTATGCC GCCGAGGTCT   1440
ACGCCCACGC CGGCCTGCCT GCGCCCGAGG AACCATTGGA ACGCAACCAG TTCCGGCGCC   1500
AGGCGCTCGA ATTGATCCGT GGCGGCGAGG CGGAACGGGG ACTGGAACTG TTCGTCGATA   1560
CGGTGAGCGG CGCCGGGGTA TGGAAACGCT CGTCGGCGAC GTTCCGCCGA ATGACGCTGG   1620
ACAACGCCAT GACCCTGGTC GGGCAGGTGG CCGACCAGCC GCCGGCGCTG GCGCTGTCGG   1680
AACTGCGCTC GATCGACCTG CCGAGCCTGA TCCTCAATGG CGAACGCAGC CCGCTGCCAT   1740
TCCCGGCCAC CGCCGAGGCG CTGGCGGCGG CCCTGCCGCG CGCCGAGCTG CAACGCATCC   1800
AGGGCGCGTC CCATGGCCTC AATGCCACCC GTCCGGCGGC TTTCAACCGG TCGGTGCTGG   1860
AGTTCCTGGC GCGCGTCGAT GGCGTTGCGC CGGACGTGGA AACGTCCTGA AGCGAGGCCG   1920
GGCGAACTGA CCGCTCGTCA GCTCGCCGCG GATGCTTTAC CATGCGTTCG CGCCGGATCA   1980
GCTCCGGCGT TTTTCGTCAG TATCCATTCC CAGTGATCTC CGTCCGCGCG CTTCGGCGCA   2040
GGGGTGCCGC AAGGCGCCTG CCACTGTGAG GCAGGCCGGC CCGGCGGGCG ACGCTTACTG   2100
GCACATCCCA ACCCACGTGG CCTTTGGTAG GGTCACCACT AGAGAGAGCG CCATGCCCAT   2160
CATTACTCTT CCCGACGGCA GTCAACGTTC CTTCGATCAC CCGGTCTCCG TGGCCGAGGT   2220
GGCCCAATCC ATCGGCGCAG GCCTGGCCAA GGCGACCCTC GCCGGCAAGG TCGACGGCCG   2280
CCTGGTCGAC GCCTGCGACA CCATCGATCG CGACGCGACC CTGCAGATCA TCACGCCCAA   2340
GGACGAGGAA GGACTGGAGA TCATCCGCCA CTCCTGCGCC CACCTGGTCG GCCATGCGGT   2400
CAAGCAGCTC TATCCGACCG CGAAGATGGT CATCGGCCCG GTGATCGAGG AAGGCTTCTA   2460
CTACGACATC TTCTTCGAGC GCCCCTTCAC CCCCGAGGAC ATGGCGGCGA TCCAGCAGGC   2520
ATGCGCGAGC TGATCGACAA GGACTACGAC GTGATCAAGA AGATGACCCC GCGCGCCGAG   2580
GTCATCGAGC TGTTCAAGTC CCGTGGCGAA GACTAACAAG CTGCGCCTGA TCGACGACAT   2640
GCCGGACGAG AAGGCCATGG GCCTGTACTT CCATGAGGAG TACGTGGACA TGTGCCGCGG   2700
CCCGCACGTG CCGAACACTC GCTTCCTCAA GGCGTTCCAG CTGACCAAGA TTTCCGGCGC   2760
CTACTGGCGC GGCGACTCGA AGAACGAGCA GTTGCAACGC ATCTACGGCA CCGCCTGGGC   2820
CGACAAGAAG CAACTGGCGG CCTACATCCA GCGCATCGAA GAGGCCGAGA AGCGCGACCA   2880
TCGCCGCATC GGCAAGCAGC TCGACCTGTT CCACCTGCAG GAAGAAGCGC CGGGCATGGT   2940
GTTCTGGCAC CCGAATGCTG GAGCGTCTAC CAGGTGCTCG AGCAGTACAT GCGCAAGGTC   3000
CAGCGCGACC ATGGCTATGT CGAAGTGCGT ACCCCGCAGG TGGTCGACCG CATCCTCTGG   3060
GAGCGTTCGG GCCACTGGTC GAACTACGCC GAGAACATGT TCACCACCTC CTCGGAAAGC   3120
CGCGACTACG CGGTCAAGCC GATGAACTGC CCGTGCCACG TGCAGATCTT CAACCAGGGC   3180
CTGAAGTCCT ACCGCGACCT GCCNTGCGCC TCGCCGAGTT CGGCGCCTGC CACCGCAACG   3240
AGCCGTCCGG CGCGCTGCAC GGATCATGCG GTACGCGGCT TTACCCAGGA CGACGCGCAT   3300
```

| | | | | | | |
|---|---|---|---|---|---|---|
| ATCTTCTGCA | CCGAAGAGCA | GGTGAAGAAG | GAAGCGGCCG | ATTTCATCAA | GCTGACTTGC | 3360 |
| AGGTCTACCG | CGACTTCGTT | TCACCGACAT | CGCCATGAAG | CTGTCGACCC | GTCCGGCCAA | 3420 |
| GCGCGTCGGT | TCCGACGAGC | TGTGGGATCC | CGAAGGCGCG | CTGGCCGATG | CGCTGAACGA | 3480 |
| ATCCGGCCTG | GCCTGGGAAT | ACCAGCCGGG | CGAGGGCGCG | TTCTACGGGC | CGAAGATCGA | 3540 |
| GTTCACCCTG | AAGGACTGCC | TCGGCCGTAA | CTGGCAGTGC | GGCACCCTGC | AGTACGACCC | 3600 |
| GAACCTGCCG | GAGCGCCTGG | ACGCCAGCTA | CATCGCCGAG | GACAACAACC | GCAAGCGCCC | 3660 |
| GGTGATGCTG | CACCGTGCGA | TCCTCGGGTC | CTTCGAGCGC | TTCATCGGCA | TGCTCATCGA | 3720 |
| GCACTACGCC | GGAGCCTTCC | CGGCCTGCTG | GCGCCGACCC | AGGCAGTGGT | GATGAACATC | 3780 |
| ACCGACAAGC | AGGCCGATTT | CGCCGCCGAG | GTGGTGCGGA | TCCTCGGGGA | AAGCGGATTC | 3840 |
| CGTGCCAAGT | CCGACTTGAG | AAACGAGAAG | ATCGGCTTTA | AATCCGCGA | GCATACTTTG | 3900 |
| CTCAAGGTTC | CCTATCTCTT | GGTTATTGGA | GATCGGGAAG | TTGAATCGAA | GGCCGTCGCG | 3960 |
| GTGCGTACGC | GCGAAGGGGA | AGACCTGGGC | TCCATGCCCG | TCACCCAGTT | CGCTGAGCTG | 4020 |
| TTGGCACAGG | CGGTTTCCCG | GCGTGGTCGC | CAAGACTCGG | AGTAATCATT | ATTAAGCGTG | 4080 |
| AAATGAGACA | GGATAAGCGA | GCTCAACCGA | AACCCCGAT | CAACGAGAAC | ATCTCGGCTC | 4140 |
| GTGAGGTACG | GTTGATTGGA | GCTGATGGCC | AGCAGGTTGG | TGTTGTTTCG | ATCGATGAGG | 4200 |
| CGATCCGCCT | AGCCGAAGAG | GCGAAGCTGG | ACCTGGTTGA | GATTTCGGCC | GACGCGGTGC | 4260 |
| CTCCTGTCTG | CCGCATCATG | GACTACGGCA | AGCACCTGTT | CGAGAAGAAG | AAGCAGGCTG | 4320 |
| CGGTCGCCAA | GAAGAACCAG | AAGCAGGCGC | AGGTCAAAGA | AATCAAGTTT | CGTCCAGGGA | 4380 |
| CGGAAGAAGG | GGATTACCAG | GTAAAACTAC | GCAACCTGGT | ACGTTTCCTT | AGTGAAGGGG | 4440 |
| ACAAGGCCAA | GGTATCCCTG | CGATTCCGCG | GCCGTGAGAT | GGCTCACCAG | GAGCTGGGGA | 4500 |
| TGGAGCTGTT | GAAGCGGGTC | GAAGCCGACC | TCGTGGAGTA | CGGCACCGTC | GAGCAGCATC | 4560 |
| CTAAGCTGGA | AGGACGCCAG | CTGATGATGG | TCATCGCTCC | CAAGAAGAAA | AAGTAACCAC | 4620 |
| CAGGGCACTG | GCAGGCCTTG | CGGTTATGCG | TAATCACTCA | ATGCGGAGTA | TCCGAACATG | 4680 |
| CCAAAGATGA | AGACCAAAAA | GTGGGCGCGG | CCAAGCGCTT | CAAGAAGACT | GCTGGTGGCC | 4740 |
| TCAAGCACAA | GCACGCCTTC | AAGAGCCACA | TCCTGACCAA | GATGACCACC | AAGCGTAAGC | 4800 |
| GTCAACTGCG | CGGCACCTCG | ATGCTGAACA | AGTCTGACGT | TGCGCGCGTA | GAACGCTCCC | 4860 |
| TGCGTCTGCG | CTGATTATTA | AGGTAGAGGA | TTAATTCATG | GCTCGTGTTA | AGCGTGGCGT | 4920 |
| TATCGCCCGT | CGTCGTCACA | AGAAAATTCT | GAAGCTCGCC | AAGGGCTACT | ACGGTGCACG | 4980 |
| CTCGCGCGTG | TTCCGCGTTG | CCAAGCAGGC | GGTGATCAAG | GCTGGCCAAT | ACGCCTACCG | 5040 |
| TGACCGTCGT | CAGCGCAAGC | GTCAGTTCCG | CGCACTGTGG | ATCGCCCGTA | TCAACGCTGG | 5100 |
| TGCTCGTCAG | AACGGTCTGT | CCTACAGCCG | CCTGATCGCC | GGCCTGAAAA | AGGCGGCCAT | 5160 |
| CGAGATCGAC | CGTAAGGTCC | TGGCCGATCT | GGCAGTGAAC | GAAAAAGCGG | CGTTTACCGC | 5220 |
| GATTGTCGAG | AAAGCGAAGG | CAAGCTT | | | | 5247 |

( 2 ) INFORMATION FOR SEQ ID NO:16:

( i ) SEQUENCE CHARACTERISTICS:
        ( A ) LENGTH: 2812 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Pseudomonas aeruginosa (B) STRAIN: Clinical Isolate P4-5

(xi) SEQUENCE DESCRIPTION: SEQ ID NO:16:

| | | | | | | |
|---|---|---|---|---|---|---|
| AAGCTTTGGT | GATCTTAACG | TGACAAGCTC | CTTAGAAAAA | TTTTATGAGT | TTATTAGCGG | 60 |
| GGTCTTTCTT | GATCCGACTG | TACCAAGACT | TTCAACTCGT | AAAATACGCA | AGCACAAAAG | 120 |
| CACTGAAATG | CACTCTGCAC | GTTTGTCGCC | GTCCACGGTA | GCGGCATCCC | TCAATCACAC | 180 |
| CGAAGCGGTG | AATCTTTCTA | CCTATGCAGA | GGCAACACCT | GAACAGCAGC | AATCCGAGTT | 240 |
| CAGCCTGTTT | TGGGATGCAA | TACGCCACGC | TGCTCATGTT | GTGCGTGAGC | GAAGCCGCAA | 300 |
| GGCTGTAGCA | AGTAGTGTCG | CAATAGCGGC | GGGTCACTGC | GAGGATTTCA | ATAAGCCGAC | 360 |
| GTCTGCCACT | GATGTGGGAT | TGATTATAGA | GCCGAACTGC | CGCACCCAAT | ATGGTTGTTT | 420 |
| GTACTGCGAA | AACTATTTAT | GTCACGGCGA | TGAGGAGGAT | CTGCATAAAA | TTCTGAGTTT | 480 |
| GCAATACGTG | GTCAATGCCG | TGCGTAAATC | GGCCCCCGAT | GCAGCGCATA | CTGAGGCACT | 540 |
| TTTCAAAGAG | TTATCTATCC | GGATCGAGTT | TATAGTCGAT | GCTCTTAGTG | AGCGCTCTAG | 600 |
| CTCGGTGAAA | CAGACAGTCG | AAAAGGTTAA | AGCTAAGGTG | TTTGAATACG | GCGAGTTAAC | 660 |
| TAAGTTTTGG | GAAGTCCGGT | TGGGTCGCTA | TGAAAAATG | GGGATCGTAT | TTTGAGTGCT | 720 |
| GCTGTTCAGT | CGATAGGTAG | TCTTTTTTCT | AGCGGCCAGT | TTCCAGTCAC | CAGCCAGCCA | 780 |
| GATAGTGCGG | CTCAGCTGTA | TGGGAAGCCC | GCGTCGGATT | TTGTTATCTG | TCGCACTGAG | 840 |
| TATGGCAATG | CAACGGCAGT | GTACGGCGAG | TCTGTATGGG | ACTTTAACCC | GTACAGGCTG | 900 |
| AGTGCAAAAA | AAATTGGCCG | AATACGCTTC | GATATGGTGT | TCGGTGATTA | TGGTCATGAT | 960 |
| CAGCAAGCGC | TGATCGAAGA | AGCCAAATAT | CTTCTGTATT | GTCTTATTTA | TTTCGCTGGC | 1020 |
| GGTGGGCGGA | TTGGTAAGCT | GAGTGCATCT | ACGATTATTT | CATATTGGGT | TGTGCTGCGC | 1080 |
| ATCGCTATGA | AGTTCTGCTA | TGCGCAGAAA | AAGAAGTCAA | TGGTTGGTGT | GCTGTCCTTG | 1140 |
| CAGCAGCTTT | TTACCGTGCC | TGTTTATCTA | GCGGCTTTTG | TTAGTGAAAG | TAATTTTGAC | 1200 |
| AAGACGGTTC | TTAGTGGGAT | ATTGCACGGA | TTGATTAGTG | TGGGCGAGGA | ACGCCTAGGG | 1260 |
| TATGTTGTGC | TGAATCCAAG | AGTTTTTGAT | TTGAGAAGAC | CTGATTCTAA | ACAGCATTCC | 1320 |
| GGTAATTCCG | ACACGCCTTT | ATTTGAATTT | AATAATATTG | TGGCGACCTG | CTCGATCATC | 1380 |
| TTACTTGGGT | GTTGGGAATA | TTGATTCATT | TATATCGTGC | TTTGCTGATG | AGTATTTCGG | 1440 |
| TCTTACTCCG | CACCGTCAAA | AATCTTTGGG | GGTTGGTGGT | AAGTCGCGCT | ATCGCCCCGG | 1500 |
| TATTCAGCAA | GCAATAGAGG | AATATGGTCT | GGCTGCGGTT | TTTGTCGGTG | AGTTTGCCTG | 1560 |
| TTCCGAAAAG | AGAAAGCTGC | AGCGAGTCCT | TCTCAAGATG | CAGTATGTGG | TGAGAATGGT | 1620 |
| GATACACCTA | TATACCGGCA | TGCGTGATCA | AGAGGTGATG | CGTATGTCTT | ATAACTGCTT | 1680 |
| ATCTGATCAA | GTCGTGAGAT | GTTCAGTGGT | TGATGATCAA | GGTTTTATGC | GCGATCAACC | 1740 |
| GCAATCAGTA | CACATATTAT | CGACTACCAC | GAAGTTTAGC | GGTTACAAGA | AAGAAAGCGC | 1800 |
| ATGGTTCGCG | GCAGGCAAG | TCGTCAAGGC | GGTCGAGGTT | GGCCAGGCGA | TTTGTCGTGG | 1860 |
| TTTAGCCCGG | CTCTATAGGA | TTGAACTGGA | TGATCGTTGT | CCGCTATTCA | TCAATCCGTC | 1920 |
| CGTCCTGTGT | AAAACGAAGA | ATTGTGCAGA | AGTTGGTGTA | ACAGACTTTA | CATTGAGAGC | 1980 |
| AACGATGGCA | GTGCTTTGAA | ATCCTTATCG | ATTCAATCAG | AGGATTTACA | AGAGTTGGCT | 2040 |
| CAGAGCGACC | CTTCTCGTGA | CTTTTACAAT | GAGCCAGATT | TTGCAGTAGG | CCAGCCCTGG | 2100 |
| CCGCTGACTA | GCCATCAATT | CCGACGTTCG | TTGGCCTTCT | ATGGAAGCAG | TAGCGGCTTT | 2160 |
| CTCTCGTTAC | CGACTCTGCG | AGCGCAGTTC | AAGCATATGA | CCCATTCAGA | TGGCGCGCTA | 2220 |
| TTATGCGAAT | GGCTTTGATA | ACTTGCGCAC | CATTTTTGGC | TACTATGACG | AGAAGAAAAT | 2280 |

| | | | | | |
|---|---|---|---|---|---|
| AGACTTCGTG | CTACCATATA | ACCACTTTGC | TTTCGAGTTC | CAGATGGCCA | TGCCGATGTC | 2340 |
| GGTGGCCAAT | CAGTTGATTG | CAGATCTGCT | GTTCAAAGAA | GAACCGCTGT | TTGGTGGCAC | 2400 |
| CGGTTCATAC | ATGCAGAGGC | AGAAAGAACG | TGTTGAAGCT | GGCGAGATAA | AGATTGAAGA | 2460 |
| TATTCGTGCC | GATACAGAGC | TTCGGGTGAA | GAACGGTGCA | ATTAGCTATC | GGCCAACGCT | 2520 |
| ACTCGGTGGT | TGCACCAAGG | TGGGCCGCTG | CGATTCCTTC | ATGCTCGGTG | ACTATACTGA | 2580 |
| ATGTTTGTCC | TGCGAGGGTG | CGATTATCAA | GCCCTCCAGG | TTAAGTGCGG | CCATTGAGGA | 2640 |
| TGCGAAAAAC | GAGTTGTCAA | ACTACGCAGA | AGACTCAGGC | GAATATCAAA | TTGTGAAGGG | 2700 |
| CGATATTGAG | CGCCTAATGG | TTTTCAAGAC | TCGCCTGATC | GACACTGTGG | AGCTTTAGTC | 2760 |
| ATGAAGTCTG | GTGAAGGAAT | AAGCAAGGGG | GTTGGTGCCT | GTCAGGAAGC | TT | 2812 |

( 2 ) INFORMATION FOR SEQ ID NO:17:

( i ) SEQUENCE CHARACTERISTICS:
        ( A ) LENGTH: 3615 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Escherichia coli
        ( B ) STRAIN: Clinical Isolate EC- 24

( x i ) SEQUENCE DESCRIPTION: SEQ ID NO:17:

| | | | | | |
|---|---|---|---|---|---|
| AAGCTTTTCT | TGCGTGTTCT | TGTGAGGCTT | CCTTCGCCAT | TATCATCACG | ATCCACATAA | 60 |
| ATAAAGCCGT | AGCGCTTAGA | CATTTGTGAA | TGAGATGCAC | TGACTAAATC | AATTGGCCCC | 120 |
| CAACTGGTGT | ACCCCATAAT | ATCCACACCA | TCGGCAATCG | CTTCATTTAC | CTGTACCAGG | 180 |
| TGATCGTTTA | AATAGGCAAT | TCGATAATCG | TCCTGTATCG | AACCATCCGC | TTCAACGCTG | 240 |
| TCTTTTGCGC | CTAATCCGTT | CTCGACAATA | AATAACGGTT | TTTGATAACG | ATCCCAAAGC | 300 |
| GTATTTAACA | GAACCCGTAA | TCCAACCGGA | TCAATTTGCC | ACCCCCACTC | TGAACTTTTC | 360 |
| AGATGCGGAT | TGGGGATCAT | ATTCAGTATG | TTGCCCTGCG | CATTTTTATT | AATGCTTTCG | 420 |
| TCGTGGGAAC | ACAACCAGTC | ATGTATAACT | AAAGAGATGA | ATCGACGGTA | TGTTTTAAAT | 480 |
| CTCTGCGTCA | CTTTCAGTCA | TCTCAATGGT | GATATTGTGG | TCGCGGAAGA | AACGCTGCAT | 540 |
| ATAGCCGGGA | TACTGGCCAC | GCGCCTGAAC | ATCACCAAAG | AACATCCAGC | GCCGGTTCTC | 600 |
| TTCCATGGCC | TGCAACATAT | CCTGTGGCTG | GCAGGTGAGG | GGGTAAACCA | GCCCACCGAG | 660 |
| AAGCATATTG | CCGATTTTCG | CTTCGGGGAG | CAGGCTATGA | CAGGCTTTAA | CTGCCCGCGC | 720 |
| ACTGGCAACC | AGTTGATGGT | GGATAGCCTG | ATAAACTTCC | GCCTCGCCAC | TCTCTTCTGC | 780 |
| CAGCCCCACG | CCCGTGAATG | GCGCGTGTAA | CGACATGTTG | ATTTCATTAA | ACGTCAGCCA | 840 |
| TAACGCCACT | TTATGTTGGT | AGCGAGTAAA | GACCGTGCGG | GCGTAATGTT | CGAAGTGATC | 900 |
| GATGACCGCT | CGATTAGCCA | ACCGCCGTAG | TTTTTCACCA | GCCCATATGG | CATTTCGTAA | 960 |
| TGGGATAACG | TTACCAGCGG | CTTGATCCCC | GCCTGCGCCA | TTTCATCAAA | CAGCCGATCG | 1020 |
| TAAAACGCTA | ACCCCGCTTC | ATTCGGTTCG | ACTTCGTCGC | CCTGAGGGAA | AATTCGCGCC | 1080 |
| CAGGCAATGG | AAATACGCAG | ACAGGTGAAG | CCCATCTCGG | CAAATAACGC | GATATCTTCC | 1140 |
| GGGTAACGGT | GATAAAAATC | GATGGCGACA | TCTTTGATAT | TCTCTTTCCC | CAGGATGCGC | 1200 |
| GGTTCCATTT | TTCCCATTAC | GCATGAGGCT | GTAAATCTGA | GGTCGAGATC | CCTTTGCCAT | 1260 |
| CTTCCTGCCA | GGCACCTTCC | ACCTGATTGG | CAGCTGTTGC | GGCACCCCAA | AGAAATGTTT | 1320 |
| CTGGAAATGC | TTTCATAATT | AACTCCTTTT | ATCGTTAGCG | AATGATGGAT | AACAGCGGTT | 1380 |

```
CACCTGCGCT  TATCTGCGCC  GTGCCGTGGG  GTAATACGTC  CGTAAAATCA  TCGCTATTAC    1440
TGATTAATAC  CGGCGTCGTC  AGATCAAATC  CGGCCTCGCG  AATAGCAGGG  ATATCAAAAG    1500
AAATCAGCCG  ATCGCCTGTA  TTGACCTTGT  CACCCACGTT  GACGTGAGCG  GAAAAGAATT    1560
TGCCGTCCAG  TTTTACGGTG  TCGATACCGA  CATGAATCAG  GATCTCCACA  CCATCATCTG    1620
ACTCAATGCC  AATGGCGTGT  AATGTGGCGA  ACAACGAAGC  AATTCGACCC  GCAACCGGAG    1680
AACGCACTTC  ACCAACCGAG  GGCAGAATGG  CAATACCTTT  ACCCAACAGG  CCACTGGCAA    1740
ACGTGGTATC  AGCGACGTGA  ATGAGCGACA  CAATCTCTCC  CGTCATCGGT  GAACAGATAC    1800
CGCCCTGCTC  AGGTGGTGTA  ATAACCTCTG  GTGTTTTCTC  TTCGGGGCAC  CCTGCGCTGG    1860
CTGACGTTTA  GCGGTGATGA  AATGAAGCAT  CACCGTACCG  ACAAATGCGC  AACCGATGGC    1920
AATGACACCG  CCAATAACGC  TGGCCCAGAC  GGTGAAATCA  ATTCCCGTTG  ACGGGATGGT    1980
TTGCATGAAG  GTGAAAATAC  TTGGCAAACC  AAAGGAGTAG  ACTTTCGTTT  GCGCGTAGCC    2040
AATAATGGTG  GCCCCCAAAG  CCCCACTGAT  ACAGGCGATA  ACAAGGGGT   ACTTACGCGG    2100
CAGGTTGACG  CCATATACCG  CTGGTTCGGT  GATACCAAAC  AGACTCGTCA  ACGCCGCTGA    2160
TCCCGCCACC  ACTTTTTTCT  GCGCATCGCG  TTCGCAGAGG  AAGACGCCGA  GCGCCGCCCC    2220
GACCTGCGCC  ATAATGGCGG  GCATTAACAG  CGGGATCATG  GTGTCGTAGC  CCAGCACGGT    2280
GAAGTTATTG  ATACACACCG  GCACCAGGCC  CCAGTGCAGT  CCGAACATGA  CGAAGATTTG    2340
CCAGAAGCCG  CCCATTACCG  CGCCCGCAAA  TGCAGGAACC  GCCTGATAAA  GCCAGAGATA    2400
ACCGGCGGCA  ATCAGTTCGC  TTATCCAGGT  TGATAGCGGC  CCCACCAGCA  GAAAGGTGAC    2460
GGGTGTGATA  ACCATCAGAC  ATAGCAATGG  TGTGAAGAAA  TTTTTGATTG  CCGACGGTAA    2520
CCACGCATTA  AGTCGGCGTT  CCAGAATGCT  GCACAACCAG  GCAGAAAAAA  TAATGGGAAT    2580
AACCGATGAC  GAGTAATTCA  ACAATGTGAC  CGGAATACCC  AGGAAATCCA  GCCCCAGCGC    2640
ATCCGCTTTT  GCGCGTTCTC  GAAAAGCAGT  ACAGAATTAA  TGGATGCACT  AACGCTCCAC    2700
CAATCACCAT  GGCAGTAAAT  GGATTATCGC  CGAAGCGTTT  CCCCGCGGTG  TATCCCAGGA    2760
TTATCGGGAA  GAACCAAAAC  AAGGCATCAC  TGGCGCTGAA  TAAAATTAAA  TAAGTACCAC    2820
TTTGTTCGGG  CGTCCACTGA  AAAGTGAGCG  CCAGAGCCAG  CATACCTTTC  AAGATCCCCG    2880
GTTGCCCGCC  ATCAAACCGA  TACAGAGGCG  TAAAAATACC  TGAAATAACA  TAAACAAAGC    2940
GGTTTAGACA  GATTACCTTT  ATCATACATT  TTCCGGTGCC  TGTTGCGCTT  TTTCGTCAAG    3000
GCCTGCCACA  CTGTTAACCG  CCAGGAAGAC  ATCGGCCACA  TGGTTACCTA  TGACCACCTG    3060
AAACTGGCCA  CCGCTTTCCA  CCACCATAAT  AATACCGGGG  GTCTTTTTCA  GTACCTCTGC    3120
TTGCGCTTTG  CTTTCATCCT  TTAATTTAAA  AACGTAAATC  GCGTTGCGCA  ATGCATCAGA    3180
CTCACAATGT  TATCTGCGCC  CCCGACTCCT  GCGACTATTT  TTCTGGCTAA  CTCCGTCATA    3240
ACTTGCCCTC  TACGCTTTGC  GGCAAAACTC  CAAAAAAAAA  CCTGAAAAAA  ACGGCCTGAC    3300
GTGAATCAAG  CAATTTTTTT  CAGGTTTTGC  CCGCTTAGTG  CGGTAACAAT  CCTTTACTCA    3360
GTAATAATAT  TTCAGTGTTC  TTTGCGCACG  CGCTCTATAT  TTATGGCTAA  AAACATAATC    3420
TCTGCGGGTG  AAATTTTACG  TTGATACTGC  AAACCAATAA  AAATGGCGAT  CCGTTCCGCA    3480
CATTGCCATG  CTTGCGGGTA  ATTTTGTTTT  ACTGCTTGTT  GTAATGATTC  ATCACTATCG    3540
TTAATTGAAG  CATGTTCAAG  AATACGCCAG  GATAAAAACT  TCAGATGTGT  AACCAGTCGC    3600
TGATAACTCA  AGCTT                                                        3615
```

( 2 ) INFORMATION FOR SEQ ID NO:18:

( i ) SEQUENCE CHARACTERISTICS:
    ( A ) LENGTH: 4954 base pairs
    ( B ) TYPE: nucleic acid
    ( C ) STRANDEDNESS: double
    ( D ) TOPOLOGY: linear ( i i ) MOLECULE TYPE: Genomic DNA ( v i ) ORIGINAL SOURCE:
    ( A ) ORGANISM: Escherichia coli
    ( B ) STRAIN: Clinical Isolate EC- 34

( x i ) SEQUENCE DESCRIPTION: SEQ ID NO:18:

```
AAGCTTAACC  GCTCTCATCT  GTTGACCGCA  CGGCATAGCT  ATATTCTGCC  GGTCCTGGGA     60
CGTAGCGAGA  TTGACATGCA  AAAAAACGGT  GCGCAGGCGG  TAACCGTTGA  GGATTCAATG    120
TCGATGATTC  ATGCCTCGCG  TGGCGTGTTA  AAACCCGCCG  GTGTAATGCT  GAAATCAGAG    180
TGTGCAGTGG  TCGCGGGAAT  CGCGCAGGCA  GCACTACCCC  AGAGCGTGGT  AGCCTGGGAG    240
TATCTGGTGG  AAGATTATGA  TCGCATTCGC  AATGACATTG  AAGCTGTGCT  GCCAGAGTTC    300
GCCGACTATA  ACCAGCGCAT  CCGTCATCCC  GGTGGTTTTC  ACCTGATAAA  TGCAGCTGCT    360
GAAAGGCGCT  GGATGACGCC  GTCAGGTAAG  GCTAATTTCA  TTACCAGCAA  AGGGCTGTTA    420
GAAGATCCCT  CTTCAGCGTT  TAACAGTAAG  CTGGTCATGG  CGACAGTACG  CAGCCACGAT    480
CAGTACAACA  CGACGATTTA  TGGTATGGAT  GATCGCTATC  GAGGGGTATT  CGGTCAACGA    540
GATGTGGTCT  TTATGAGTGC  TAAACAAGCT  AAAATTTGCC  GTGTAAAAAA  CGGCGAAAGA    600
GTTAATCTTA  TTGCGCTTAC  GCCAGACGGT  AAGCGCAGTC  ACGCCGCATG  GATAGATTAA    660
AAGTGGTCAT  TTACCCTATG  GCTGACCGCT  CACTGGTGAC  CTATTTTCCA  GAATCGAATC    720
ACATGCTAAC  ACTTGATAAC  CACGATCCAT  TAAGTGGCAT  TCCTGGCTAT  AAAAGTATTC    780
CGCTTGAATT  AGAACCATCA  AATTAATGTC  TCTTCTCATT  TCTTCTGCTG  TCATCCGCAC    840
AGCAGAAGAA  TTCCTCATTG  ACTATTATTT  CGCAATTTGC  TCACATGGAT  TAAATTAAAC    900
TACATACTAT  AAGATATAAA  CTTCTGCCTA  CAGCTGTAAG  AAACTCCGCT  CAGTACTGAA    960
GCACCAGTCC  TATTTCCTCT  TTTCTCCAGC  CTGTTATATT  AAGCATACTG  ATTAACGATT   1020
TTTAACGTTA  TCCGCTAAAT  AAACATATTT  GAAATGCATG  CGACCACAGT  GAAAAACAAA   1080
ATCACGCAAA  GAGACAACTA  TAAAGAAATC  ATGTCTGCAA  TTGTGGGTGT  CTTATTACTG   1140
ACACTTACGT  GATAGCCATT  TTTTCGGCAA  TTGATCAGCT  GAGTATTTCA  GAAATGGGTC   1200
GCATTGCAAG  AGATCTTACA  CATTTCATTA  TCAATAGTTT  GCAAGGCTGT  AAACAAACAG   1260
CAAATTATAA  ATATGAAATG  TTAAAAAGT   ATCGATAAAA  ACTTTATTGT  TTTAAGGAGA   1320
TAAAATGTCG  CTCGTTTGTT  CTGTTATATT  TATTCATCAT  GCCTTCAACG  CTAACATTTT   1380
AGATAAAGAT  TACGCCTTCT  CTGACGGCGA  GATCCTGATG  GTAGATAACG  CTGTTCGTAC   1440
GCATTTTGAA  CCTTATGAGC  GGCATTTTAA  AGAGATCGGA  TTTACTGAAA  ATACCATTAA   1500
AAAATATCTA  CAATGCACTA  ACATCCAGAC  AGTGACGGTG  CCTGTTCCTG  CGAAGTTTTT   1560
ACGTGCTTCA  AATGTACCGA  CTGGATTGCT  TAATGAAATG  ATTGCTTATC  TCAACTCGGA   1620
AGAACGCAAT  CATCATAATT  TTTCAGAACT  TTTGCTTTTT  TCTTGCCTGT  CTATTTTTGC   1680
CGCATGCAAA  GGTTTCATTA  CACTATTAAC  TAACGGTGTG  CTATCCGTTT  CTGGGAAAGT   1740
GAGAAATATT  GTCAACATGA  AGCCGGCGCA  CCCATGGAAG  CTGAAAGATA  TTTGTGACTG   1800
CCTGTACATC  AGTGAAAGCC  TGTTGAAGAA  AAACTTAAGC  AAGAGCAAAC  GACATTCTCA   1860
CAGATTCTTT  TAGATGCAAG  AATGCAGCAC  GCAAAAAATT  TGATACGCGT  AGAAGGTTCA   1920
GTCAATAAAA  TTGCCGAACA  ATGTGGTTAT  GCCAGTACAT  CTTATTTTAT  TTATGCGTTC   1980
```

| | | | | | | |
|---|---|---|---|---|---|---|
| CGCAAACATT | TCGGCAACAG | TCCGAAGAGA | GTTTCTAAGG | AGTACCGTTG | TCAAAGTCAC | 2040 |
| ACGGGTATGA | ATACGGGCAA | CACGATGAAT | GCTTTAGCTA | TTTGATTATT | TGCTAACGAG | 2100 |
| TAGTCAACCA | CACACGCTGC | GTAAGAATTA | AATGGGGCAG | CCATTCCCTG | CCCCGCGTTG | 2160 |
| TTTTTAGGCG | ATATATTTAT | TGAAATAAAT | AAGTGACATC | CATCACATAT | TTATGCACTT | 2220 |
| GCATAACCTG | TTGCATGATT | ATTTATGATC | TCAATTCTGC | ATTTTGTCAG | TAAAATGCAA | 2280 |
| TAATTTATTA | AATATCAATA | AATTAGTTGT | TTATCGGCGA | GAAATTACTT | AATAGAACAG | 2340 |
| AAAGTAATGT | CAACGCTTTA | TGGACTGTTT | TTTCCCTTTT | TTTAGCTAAA | TCTGCTATCT | 2400 |
| CTTTATGTGA | CTAACTTCAC | TTACATCCAC | TTATTTCTCT | TCGTAAAATT | ACTTTGGAAT | 2460 |
| TAAGTACAAT | AAGAAGAGGA | ACATTTATGA | AGTCTGCATT | AAAGAAAGT | GTCGTAAGTA | 2520 |
| CCTCGATATC | TTTGATACTG | GCATCTGGTA | TGGCTGCATT | TGCTGCTCAT | GCGGCAGATG | 2580 |
| ATGTAAAGCT | GAAAGCAACC | AAAACAAACG | TTGCTTTCTC | AGACTTTACG | CCGACAGAAT | 2640 |
| ACAGTACCAA | AGGAAAGCCA | AATATTATCG | TACTGACCAT | GGATGATCTT | GGTTATGGAC | 2700 |
| AACTTCCTTT | TGATAAGGGA | TCTTTTGACC | CAAAAACAAT | GGAAAATCGT | GAAGTTGTCG | 2760 |
| ATACCTACAA | AATAGGGATA | GATAAAGCCA | TTGAAGCTGC | ACAAAAATCA | ACGCCGACGC | 2820 |
| TCCTTTCATT | AATGGATGAA | GGCGTACGTT | TTACTAACGG | CTATGTGGCA | CACGGTGTTT | 2880 |
| CCGGCCCCTC | CCGCGCCGCA | ATAATGACCG | GTCGAGCTCC | CGCCCGCTTT | GGTGTCTATT | 2940 |
| CCAATACCGA | TGCTCAGGAT | GGTATTCCGC | TAACAGAAAC | TTTCTTGCCT | GAATTATTCC | 3000 |
| AGAATCATGG | TTATTACACT | GCAGCAGTAG | GTAAATGGCA | CTTGTCAAAA | ATCAGTAATG | 3060 |
| TGCCGGTACC | GGAAGATAAA | CAAACGCGTG | ACTATCATGA | CACCTTCACC | ACATTTTCTG | 3120 |
| CGGAAGAATG | GCAACCTCAA | AACCGTGGCT | TTGATTACTT | TATGGGATTC | CACGCTGCAG | 3180 |
| GAACGGCATA | TTACAACTCC | CCTTCACTGT | TCAAAAATCG | TGAACGTGTC | CCCGCAAAAG | 3240 |
| GTTATATCAG | CGATCAGTTA | ACCGATGAGG | CAATTGGCGT | TGTTGATCGT | GCCAAAACAC | 3300 |
| TTGACCAGCC | TTTTATGCTT | TACCTGGCTT | ATAATGCTCC | GCACCTGCCA | AATGATAATC | 3360 |
| CTGCACCGGA | TCAATATCAG | AAGCAATTTA | ATACCGGTAG | TCAAACAGCA | GATAACTACT | 3420 |
| ACGCTTCCGT | TTATTCTGTT | GATCAGGGTG | TAAAACGCAT | TCTCGAACAA | CTGAAGAAAA | 3480 |
| ACGGACAGTA | TGACAATACA | ATTATTCTCT | TTACCTCCGA | TAATGGTGCG | GTTATCGATG | 3540 |
| GTCCTCTGCC | GCTGAACGGG | GCGCAAAAAG | GCTATAAGAG | TCAGACCTAT | CCTGGCGGTA | 3600 |
| CTCACACCCC | AATGTTTATG | TGGTGGAGAA | GGAAAACTTC | AACCCGGTAA | TTATGACAAG | 3660 |
| CTGATTTCCG | CAATGGATTT | CTACCCGACA | GCTCTTGATG | CAGCCGATAT | CAGCATTCCA | 3720 |
| AAAGACCTTA | AGCTGGATGG | CGTTTCCTTG | CTGCCCTGGT | TGCAAGATAA | GAAACAAGGC | 3780 |
| GAGCCACATA | AAAATCTGAC | CTGGATAACC | TCTTATTCTC | ACTGGTTTGA | CGAGGAAAAT | 3840 |
| ATTCCATTCT | GGGATAATTA | CCACAAATTT | GTTCGCCATA | CAGTCAGACG | ATTACCCGCA | 3900 |
| TAACCCCAAC | ACTGAGGACT | TAAGCCAATT | CTCTTATACG | GTGAGAAATA | ACGATTATTC | 3960 |
| GCTTGTCTAT | ACAGTAGAAA | ACAATCAGTT | AGGTCTCTAC | AAACTGACGG | ATCTACAGCA | 4020 |
| AAAAGATAAC | CTTGCCGCCG | CCAATCCGCA | GGTCGTTATA | GAGATGCAAG | GCGTGGTAAG | 4080 |
| AGAGTTTATC | GACAGCAGCC | AGCCACCGCT | TAGCGAGGTA | AATCAGGAGA | AGTTTAACAA | 4140 |
| TATCAAGAAA | GCACTAAGCG | AAGCGAAATA | ACTAAACCTT | CATGCGGCGG | ATTTTCCGC | 4200 |
| CGCCTTATTG | AGCGAGATAG | CGATGCACGT | TACAGCCAAG | CCCTCCAGTT | TTCAATGTAA | 4260 |
| TCTCAAATGT | GATTACTGTT | TTTACCTTGA | AAAAGAGTCG | CAGTTTACTC | ATGAAAAATG | 4320 |
| GATGGATGAC | AGCACTTTGA | AAGAGTTCAT | CAAACAATAT | ATCGCAGCGT | CTGGCAATCA | 4380 |

| | | | | | |
|---|---|---|---|---|---|
| GGTCTATTTT | ACCTGGCAAG | GCGGTGAACC | CACTCTGGCT | GGCCTGGATT | TTTTCCGTAA | 4440
| AGTTATTCAC | TATCAACAAC | GCTATGCAGG | CCAAAAACGT | ATTTTTAATG | CATTACAAAC | 4500
| GAATGGCATT | TTATTGAATA | ATGAATGGTG | TGCCTTCTCA | AAGAACATGA | ATTTCTGGTG | 4560
| GTATCTCGAT | CGATGGCCCC | CAGGAGTTAC | ATGACCGTTA | CAGACGCAGT | AATTCAGGTA | 4620
| ACGGTACTTT | TGCAAAAGTG | ATAGCAGCCA | TCGAGCGTCT | GAAATCATAT | CAAGTAGAGT | 4680
| TTAATACGTT | AACCGTCATT | AATAACGTTA | ATGTCCATTA | CCCTCTTGAG | GTTTATCATT | 4740
| TTTTAAAATC | TATCGGCAGT | AAACATATGC | AATTTATCGA | ATTGCTAGAA | ACCGGACGC | 4800
| CGAATATTGA | TTTCAGTGGT | CATAGTGAGA | ACACATTCCG | TATCATTGAT | TTTTCTGTGC | 4860
| CTCCCACGGC | TTATGGCAAG | TTTATGTCAA | CCATTTTTAT | GCAATGGGTT | AAAAACGATG | 4920
| TGGGTGAAAT | TTTCATCCGT | CAGTTTGAAA | GCTT | | | 4954

( 2 ) INFORMATION FOR SEQ ID NO:19:

( i ) SEQUENCE CHARACTERISTICS:
        ( A ) LENGTH: 3796 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Escherichia coli
        ( B ) STRAIN: Clinical Isolate EC- 39

( x i ) SEQUENCE DESCRIPTION: SEQ ID NO:19:

| | | | | | |
|---|---|---|---|---|---|
| AAGCTTAATC | GCGTGAATCA | GGAGTAAAAA | AATGACAACC | CAGACTGTCT | CTGGTCGCCG | 60
| TTATTTCACG | AAAGCGTGGC | TGATGGAGCA | GAAATCGCTT | ATCGCTCTGC | TGGTGCTGAT | 120
| CGCGATTGTC | TCGACGTTAA | GCCCGAACTT | TTTCACCATC | AATAACTTAT | TCAATATTCT | 180
| CCAGCAAACC | TCAGTGAACG | CCATTATGGC | GGTCGGGATG | ACGCTGGTGA | TCCTGACGTC | 240
| GGGCATCGAC | TTATCGGTAG | GTTCTCTGTT | GGCGCTGACC | GGCGCAGTTG | CTGCATCTAT | 300
| CGTCGGCATT | GAAGTCAATG | CGCTGGTGGC | TGTCGCTGCT | GCTCTCGCGT | TAGGTGCGCA | 360
| ATTGGTGCGG | TAACCGGGGT | GATTGTAGCG | AAAGGTCGCG | TCCAGGCGTT | TATCGCTACG | 420
| CTGGTTATGA | TGCTTTTACT | GCGCGGCGTG | ACCATGGTTT | ATACCAACGG | TAGCCCAGTG | 480
| AATACCGGCT | TTACTGAGAA | CGCCGATCTG | TTTGGCTGGT | TTGGTATTGG | TCGTCCGCTG | 540
| GGCGTACCGA | CGCCAGTCTG | GATCATGGGG | ATTGTCTTCC | TCGCGGCCTG | GTACATGCTG | 600
| CATCACACGC | GTCTGGGGCG | TTACATCTAC | GCGCTGGGCG | ACAACGAAGC | GACAACGCGT | 660
| CTTTCTGGTA | TCAACGTCAA | TAAAATCAAA | ATCATCGTCT | ATTCTCTTTG | TGGTCTGCTG | 720
| GCATCGCTGG | CGGGATCATA | GAAGTGGCGC | GTCTCTCCTC | CGCACAACCA | CGGCGGGGAC | 780
| TGGCTATGAG | CTGGATGCTA | TTGCTGCGGT | GGTTCTGGGC | GGTACGAGTC | TGGCGGGCGG | 840
| AAAAGGTCGC | ATTGTTGGGA | CGTTGATCGG | CGCATTAATT | CTTGGCTTCC | TTAATAATGG | 900
| ATTGAATTTG | TTAGGTGTTT | CCTCCTATTA | CCAGATGATC | GTCAAAGCGG | TGGTGATTTT | 960
| GCTGGCGGTG | CTGGTAGACA | ACAAAAAGCA | GTAATAACGA | CTACAGGCAC | ATCTTGAATA | 1020
| TGAACATGAA | AAAACTGGCT | ACCCTGGTTT | CCGCTGTTGC | GCTAAGCGCC | ACCGTCAGTG | 1080
| CGAATGCGAT | GGCAAAAGAC | ACCATCGCGC | TGGTGGTCTC | CACGCTTAAC | AACCCGTTCT | 1140
| TTGTATCGCT | GAAAGATGGC | GCGCAGAAAG | AGGCGGATAA | ACTTGGCTAT | AACCTGGTGC | 1200
| TGGACTCCCA | GAACAACCCG | GCGAAAGAGC | TGGCGAACGT | GCAGGACTTA | ACCGTTCGCG | 1260
| GCACAAAAAT | TCTGCTGATT | AACCCGACCG | ACTCCGACGC | AGTGGGTAAT | GCTGTGAAGA | 1320

| | | | | | | |
|---|---|---|---|---|---|---|
| TGGCTAACCA | GGCGAACATC | CCGGTTATCA | CTCTTGACCG | CCAGGCAACG | AAAGGTGAAG | 1380 |
| TGGTGAGCCA | CATTGCTTCT | GATAACGTAC | TGGGCGGCAA | AATCGCTGGT | GATTACATCG | 1440 |
| CGAAGAAAGC | GGGTGAAGGT | GCCAAAGTTA | TCGAGCTGCA | AGGCATTGCT | GGTACATCCG | 1500 |
| CAGCCCGTGA | ACGTGGCGAA | GGCTTCCAGC | AGGCCGTTGC | TGCTCACAAG | TTTAATGTTC | 1560 |
| TTGCCAGCCA | GCCAGCAGAT | TTTGATCGCA | TTAAAGGTTT | GAACGTAATG | CAGAACCTGT | 1620 |
| TGACCGCTCA | TCCGGATGTT | CAGGCTGTAT | TCGCGCAGAA | TGATGAAATG | GCGCTGGGCG | 1680 |
| CGCTGCGCGC | ACTGCAAACT | GCCGGTAAAT | CGGATGTGAT | GGTCGTCGGA | TTTGACGGTA | 1740 |
| CACCGGATGG | CGAAAAAGCG | GTGAATGATG | GCAAACTAGC | AGCGACTATC | GCTCAGCTAC | 1800 |
| CCGATCAGAT | TGGCGCGAAA | GGCGTCGAAA | CCGCAGATAA | AGTGCTGAAA | GGCGAGAAAG | 1860 |
| TTCAGGCTAA | GTATCCGGTT | GATCTGAAAC | TGGTTGTTAA | GCAGTAGTTT | TAATCAGGTT | 1920 |
| GTATGACCTG | ATGGTGACAT | AAATACGTCA | TCGACAGATG | AACGTGTAAT | ATAAAGAAAA | 1980 |
| GCAGGGCACG | CGCCACCCTA | ACACGGTGGC | GCATTTTATG | GACATCCCGA | ATATGCAAAA | 2040 |
| CGCAGGCAGC | CTCGTTGTTC | TTGGCAGCAT | TAATGCTGAC | CACATTCTTA | ATCTTCAATC | 2100 |
| TTTTCCTACT | CCAGGCGAAA | CGTAACCGGT | AACCACTATC | AGGTTGCATT | TGGCGGCAAA | 2160 |
| GGCGCGAATC | AGGCTGTGGC | TGCTGGGCGT | AGCGGTGCGA | ATATCGCGTT | TATTGCCTGT | 2220 |
| ACGGGTGATG | ACAGCATTGG | TGAGAGCGTT | CGCCAGCAGC | TCGCCACTGA | TAACATTGAT | 2280 |
| ATTACTCCGG | TCAGCGTGAT | CAAAGGCGAA | TCAACAGGTG | TGGCGCTGAT | TTTTGTTAAT | 2340 |
| GGCGAAGGTG | AGAATGTCAT | CGGTATTCAT | GCCGGCGCTA | ATGCTGCCCT | TTCCCCGGCG | 2400 |
| CTGGTGGAAG | CGCAACGTGA | GCGTATTGCC | AACGCGTCAG | CATTATTAAT | GCAGCTGGAA | 2460 |
| TCACCACTCG | AAAGTGTGAT | GGCAGCGGCG | AAAATCGCCC | ATCAAAATAA | AAACTATCGT | 2520 |
| TCGCTTAACC | CGCTCCGGCT | CGCGAACTTC | CTGACGAACT | CTGCGCTGTG | GACATTATTA | 2580 |
| CGCCAAACGA | AACGGAAGCA | GAAAAGCTCA | CCGGTATTCG | TGTTGAAAAT | GATGAAGATG | 2640 |
| CAGCGAAGGC | GGCGCAGGTA | CTTCATGAAA | AAGGTATCCG | TACTGTACTG | ATTACTTTAG | 2700 |
| GAAGTCGTGG | TGTATGGGCT | AGCGTGAATG | GTGAAGGTCA | GCGCGTTCCT | GGATTCCGGG | 2760 |
| TGCAGGCTGT | CGATACCATT | GCTGCCGGAG | ATACCTTTAA | CGGTGCGTTA | ATCACGGCAT | 2820 |
| TGCTGGAAGA | AAAACCATTG | CCAGAGGCGA | TTCGTTTTGC | CCATGCTGCC | GCTGCGATTG | 2880 |
| CCGTAACACG | TAAAGGCGCA | CAACCTTCCG | TACCGTGGCG | TGAAGAGATC | GACGCATTTT | 2940 |
| TAGACAGGCA | GAGGTGACGC | TTGGCTACAA | TGAAAGATGT | TGCCCGCCTG | GCGGGCGTTT | 3000 |
| CTACCTCAAC | AGTTTCTCAC | GTTATCAATA | AAGATCGCTT | CGTCAGTGAA | GCGATTACCG | 3060 |
| CAAAGTGAGC | GCGATTAAAG | ACTCAATTAC | GCGCCATCAG | CTCTGGCGCG | TAGCCTCAAA | 3120 |
| CTCAATCAAA | CACATACCAT | TGGCATGTTG | ATCACTGCCA | GTACCAATCC | TTTCTATTCA | 3180 |
| GAACTGGTGC | GTGTCGTTGA | ACGCAGCTGC | TTCGAACGCG | GTTATAGTCT | CGTCCTTTGC | 3240 |
| AATACCGAAG | GCGATGAACA | GCGGATGAAT | CGCAATCTGG | AAACGCTGAT | GCAAAACGC | 3300 |
| GTTGATGGCT | TGCTGTTACT | GTGCACCGAA | ACGCATCAAC | CTTCGCGTGA | AATCATGCAA | 3360 |
| CGTTATCCGA | CAGTGCCTAC | TGTGATGATG | GACTGGGCTC | CGTTCGATGG | CGACAGCGAT | 3420 |
| CTTATTCAGG | ATAACTCGTT | GCTGGGCGGA | GACTTAGCAA | CGCAATATCT | GATCGATAAA | 3480 |
| GGTCATACCC | GTATCGCCTG | TATTACCGGC | CCGCTGGATA | AAACTCCGGC | GCGCTGCGGT | 3540 |
| TGGAAGGTTA | TCGGGCGGCG | ATGAAACGTG | CGGGTCTCAA | CATTCCTGAT | GGCTATGAAG | 3600 |
| TCACTGGTGA | TTTTGAATTT | AACGGCGGGT | TTGACGCTAT | GCGCCAACTG | CTATCACATC | 3660 |
| CGCTGCGTCC | TCAGGCCGTC | TTTACCGGAA | ATGACGCTAT | GGCTGTTGGC | GTTTACCAGG | 3720 |

5,807,673

-continued

| CGTTATATCA | GGCAGAGTTA | CAGGTTCCGC | AGGATATCGC | GGTGATTGGC | TATGACGATA | 3780 |
| TCGAACTGGC | AAGCTT | | | | | 3796 |

( 2 ) INFORMATION FOR SEQ ID NO:20:

( i ) SEQUENCE CHARACTERISTICS:
        ( A ) LENGTH: 5541 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Escherichia coli
        ( B ) STRAIN: Clinical Isolate EC- 625

( x i ) SEQUENCE DESCRIPTION: SEQ ID NO:20:

| AAGCTTAAGC | CTGCATTTGC | TCAATGAAGC | GCAGAATGAG | CTGGAACTGT | CAGAAGGCAG | 60 |
| CGACGATAAC | GAAGGTATTA | AAGAACGTAC | CAGCTTCCGT | CTGGAGCGTC | GGGTCGCCGG | 120 |
| AGTGGGTCGT | CAAATGGGCC | GCGGTAACGG | CTATCTGGCA | ACCATCGGCG | CGATTTCTCC | 180 |
| GTTCGTTGGT | CTGTTTGGTA | CGGTCTGGGG | CATCATGAAC | AGCTTTATTG | GTATCGCGCA | 240 |
| AACGCAGACC | ACTAACCTGG | CAGTCGTTGC | GCCGGGTATC | GCAGAAGCTC | TGTTAGCAAC | 300 |
| GGCAATCGGC | CTCGTGGCAG | CGATTCCTGC | GGTCGTTATC | TATAACGTAT | TTGCACGCCA | 360 |
| GATTGGCGGC | TTTAAAGCGA | TGCTGGGTGA | TGTTGCAGCG | CAGGTATTGT | TGCTGCAAAG | 420 |
| CCGTGACCTG | GATCTGGAAG | CCAGCGCCGC | TGCGCATCCG | GTTCGTGTCG | CACAAAAATT | 480 |
| ACGCGCAGGA | TAATATCCGA | TGGCAATGCA | TCTTAACGAA | AACCTCGACG | ATAACGGCGA | 540 |
| AATGCATGAT | ATCAACGTGA | CGGCGTTTAT | CGACGTGATG | TTGGTTCTGC | TGATTATCTT | 600 |
| TATGGTGGCG | GCACCGTTAG | CGACGGTAGA | TGTGAAGGTG | AACTTGCCTG | CTTCTACCAG | 660 |
| CACGCCGCAG | CCGCGGCCGG | AAAAACCGGT | TTATCTGTCG | GTGAAGGCAG | ACAACTCGAT | 720 |
| GTTTATCGGT | AACGATCCGG | TCACCGATGA | AACAATGATT | ACGGCGTTGA | ATGCGTTAAC | 780 |
| CGAAGGCAAG | AAAGACACCA | CCATCTTCTT | CCGAGCGGAT | AAAACCGTCG | ATTACGAGAC | 840 |
| GTTGATGAAG | GTAATGGATA | CGCTGCATCA | GGCGGGTTAC | CTGAAGATAG | GTCTGGTCGG | 900 |
| CGAAGAAACC | GCCAAAGCGA | AGTAAAGTAG | AATTGCCTGA | TGCGCTACGC | TCATCAGGCC | 960 |
| TACAAAATCT | ATTGCAACAT | GTTGAATCTT | CGTGCGTTTG | TAGGCCGGAT | AAGGCGTTCA | 1020 |
| CGCGCATCCG | GCATTAGGTG | CTCAATGCCT | GATGCGCTAC | GTTTATCAGG | CCTACAAAAT | 1080 |
| CTATTGCAAC | ATGTTGAATC | TTCATGCGTT | TGTAGGCGGA | TAAGGCGTTT | CGCACATCA | 1140 |
| GGTAAGAGTG | AATTCACAAT | GATGCCCGGT | TGCTTTTCAC | AACCGGGCAT | TTTTTAACC | 1200 |
| TAAATGCTCG | CCGCCGCACA | CACCGTGCAC | TTCTGCGGTG | ACGTAGCTCG | ACTCCTGACT | 1260 |
| TGCCAGATAA | ACATATACTG | GGGCCAGTTC | CGCCGGTTGC | CCCGCACGCT | TCATCGGCGT | 1320 |
| TTTCTGACCA | AACTGCGGGA | TCTTATCCTG | CGTTTGTCCG | CCGGAAATTT | GCAGTGCCGT | 1380 |
| CCAGATAGGG | CCTGGCGCGA | CAATATTCAC | CCGAATACCT | TTCTCCGCGA | CCTGTTTTGC | 1440 |
| CAGGCCACGG | CTGTAGTTCA | GAATCGCCGC | CTTCGTAGCC | GCATAGTCCA | GTAAATGCGG | 1500 |
| ACTTGGCTGG | TATGCCTGGA | TTGACGAAGT | GGTGATAATA | CTTGCACCTT | TCGGTAGCAG | 1560 |
| GGGGATCGCT | TCCTGGGTTA | GCCAGAACAG | CGCGAAAACG | TTAATGGCAA | AGGTCTTTTG | 1620 |
| AAACTGTTCG | CTGGTGAGGT | CTGCAATATC | AGGAATGGCA | ACCTGTTTCC | CGGCGACCAG | 1680 |
| CGCCATAATA | TCCAGCCCGC | CTAACGCCTT | GTGCGCTTCG | TGAACCAGCG | AACGGGCGAA | 1740 |

-continued

| | | | | | | |
|---|---|---|---|---|---|---|
| TTTCTCATCG | CTTAAATCGC | CTGGCAGCAG | AACGGCTTTG | CGTCCGCATT | CTTCAATGAT | 1800 |
| CTTTTTCACA | TCCTGAGCGT | CTTCTTCTTC | CACGGGAAGA | TAACTGATCG | CCACGTCAGC | 1860 |
| CCCTTCACAC | GCGTAAGATG | GCGGCAGCGC | GACCGATTCC | GGAATCGCCC | CCTGTCACCA | 1920 |
| GTGCTTTACG | ATCTTTCAGG | CGACCGCTAC | CAACATAGGT | TTTCTCGCCG | CAATCCGGTA | 1980 |
| CCGGTGTCAT | CTTCGCCTGG | ATGCCTGGCG | TCGTTGTTT | CTGTTTGGGA | TATTCACCAG | 2040 |
| TGTAATACTG | CGTGGTCGGG | TCTTTTAAAT | GAGACATCGT | TTTTCTCCCT | TCAGGTTCAA | 2100 |
| CGTCCTTTAA | GGGTAGACGC | TCTCGATGCG | TTGATAAGGG | AACCAGGAAG | ATCCCTAACC | 2160 |
| CTCAGAATTA | TGCGACAAAG | GTTAACGGA | TATGTTGATT | TGCTGTTGCG | CGCTGTTTAC | 2220 |
| TCAATTGCGA | TATACTGTTG | CCCGTTTTAA | CTACACGACA | GGAATGTATG | AACGTTTTC | 2280 |
| TTGAAAATGC | AATGTATGCT | TCTCGCTGGC | TGCTTGCCCC | CGTGTACTTT | GGCCTTTCGC | 2340 |
| TGGCGTTAGT | TGCCCTGGCG | CTGAAGTTCT | TCCAGGAGAT | TATTCACGTA | CTGCCGAATA | 2400 |
| TCTTCTCGAT | GGCGGAATCA | GATTGATCC | TCGTGTTGCT | GTCGCTGGTG | GATATGACAC | 2460 |
| TGGTTGGCGG | TTTACTGGTG | ATGGTGATGT | TTTCCGGTTA | TGAGAATTTC | GTCTCGCAGC | 2520 |
| TGGATATCTC | CGAGAACAAA | GAGAAGCTGA | ACTGGCTGGG | GAAAATGGAC | GCAACGTCGC | 2580 |
| TGAAAAACAA | AGTAGCAGCG | TCGATTGTGG | CAATTCTTC | CATTCACTTA | CTGCGCGTCT | 2640 |
| TTATGGATGC | GAAAAATGTC | CCTGATAACA | AACTGATGTG | GTACGTCATT | ATCCATCTGA | 2700 |
| CGTTTGTGCT | CTCTGCATTT | GTGATGGGCT | ATCTTGACCG | ACTGACTCGT | CATAATCACT | 2760 |
| GATCTTATGC | GGGCGCGGTT | CTCGCGCCCG | TTATTAACAG | GTCATTTATC | GGAAGACGCC | 2820 |
| TGCCACAGAT | TCAGCTCGCC | ATCGGCGATA | TGCTGATCAA | TCTGCGCCAG | CTCCTCGGTG | 2880 |
| CTAAATGTCA | GATTATTCAG | CGCCTGCACG | TTCTCCTCAA | GTTGTCCGCG | CGGCTGGCAC | 2940 |
| CAATCAATAC | CGACGTCACG | CGATCATCTT | TCAGCAACCA | GCTTAACGCC | ATTTGCGCCA | 3000 |
| TTGATTGTCC | ACGCTGCTGT | GCCATTTCAT | TCAATAAGTG | TAGGCTGTTG | AGGTTGGCTT | 3060 |
| CGGTAAGCAT | TTTCGGCGTC | AGACCACGAA | CTTTATTCCC | TTCACGATGC | ATCCGTGAAT | 3120 |
| CTTGCGGAAT | GCCGTTGAGA | TATTTTCCGG | TCAGCAATCC | CTGAGCCAGA | GGAGTAAAGG | 3180 |
| CAATACAGCC | CACGCCGTTA | TTTTGCAGGG | TATCCAGCAG | GCCGCTTTTA | TCCACCCAGC | 3240 |
| GGTTCAGTAA | ATTGTACGAA | GGTTGATGAA | TTAACAGCGG | AATTTTCCAC | TCGCGCAGCA | 3300 |
| ACTCAACCAT | TTTTTGCGTC | CGCTCTGGCG | AGTAAGAGGA | GATCCCGACA | TAAAGCGCCT | 3360 |
| TACCGCTTTG | TACCGCATGA | GCCAGCGCAG | AGGCGGTTTC | TTCCATCGGC | GTATTTTCAT | 3420 |
| CGACGCGATG | AGAGTAAAAG | ATATCGACAT | ACTCAAGCCC | CATACGCTTC | AGGCTTTGGT | 3480 |
| CGAGGCTGGA | GAGCAGGTAT | TTACGTGAAC | CGCCAGAGCC | GTAAGGGCCG | GCCACATAT | 3540 |
| CGTAGCCAGC | CTTGGTAGAG | ATAATCAGTT | CATCGCGATA | AGCGGCAAAA | TCCTCCCGCA | 3600 |
| GCAGGCGACC | AAAGTTCTCT | TCTGCGCTTC | CTGGAGGCGG | CCCGTAATTG | TTGGCTAAAT | 3660 |
| CAAAGTGCGT | AATGCCTAAA | TCAAACGCTT | TACGCAGGAT | TGCACGCTGT | GATTCCAGCG | 3720 |
| CGTTAACGTG | ACCGAAATTG | TGCCATAAAC | CGAGCGATAA | CGCGGGCAGG | CGTAAACCAC | 3780 |
| TTTTTCCGCA | ATAGCGGTAC | TGCATCTGCC | CGTAACGTTC | GGGTTCGCTA | ACCAGACCAT | 3840 |
| GACCTCTCCT | TTCCACCGTT | CAATTTCGAA | ACAATGTTTC | TAGTTTAGCG | ATTCGCCAGC | 3900 |
| GCGTATCCCG | TAGTCTGGCT | CACAGAGTGA | CGAAAAATTG | GCAAAAACAC | GCGCTTATGC | 3960 |
| TTTGCTTAAA | AAAACACCAG | TTGAGGAGTG | CAACGATGCC | GCGTTTAACC | GCCAAAGATT | 4020 |
| TCCCACAAGA | GTTGTTGGAT | TACTACGACT | ATTACGCTCA | CGGGAAAATC | TCGAACGTG | 4080 |
| AGTTCCTCAA | TCTTGCGGCG | AAGTATGCGG | TGGGCGGGAT | GACGGCATTA | GCGTTGTTTG | 4140 |

-continued

| | | | | | | |
|---|---|---|---|---|---|---|
| ATTTGCTCAA | GCCAAATTAT | GCGCTGGCGA | CTCAGGTAGA | GTTTACCGAC | CTGGAGATTG | 4200 |
| TTGCTGAGTA | CATCACGTAT | CCTTCGCCAA | ATGGTCACGG | CGAGGTACGG | GGTTATCTGG | 4260 |
| TGAAACCCGC | AAAAATGAGC | GGCAAAACGC | CAACCGTGGT | GGTGGTGCAT | GAGAATCGTG | 4320 |
| GACTGAATCC | GTATATCGAA | GATGTGGCAC | GGCGAGTGGC | GAAGGCGGGG | TATATCGCCC | 4380 |
| TGGCACCTGA | CGGCTTAAGT | TCCGTTGGAG | GTTATCCGGG | AAATGATGAT | AAAGGTCGTG | 4440 |
| AGCTGCAACA | GACAGGTTGA | TCCAACCAAA | CTGATGAATG | ATTTCTTTGC | CGCAATTGAG | 4500 |
| TTTATGCAAC | GCTATCCGCA | AGCGACAGGC | AAAGTGGGTA | TTACCGGATT | TTGCTATGGC | 4560 |
| GGTGGCGTAT | CGAACGCGGC | GGCTGTCGCG | TATCCGGAAC | TGGCCTGCGC | GGTGCCGTTT | 4620 |
| TATGGTCGTC | AGGCACCCAC | TGCCGATGTG | GCGAAGATTG | AAGCGCCTTT | ACTACTCCAC | 4680 |
| TTCGCGGAAC | TGGACACCCG | AATCAACGAG | GGCTGGCCTG | CTTACGAGGC | GGCGTTGAAA | 4740 |
| GCCAATAATA | AGGTTTATGA | GGCGTATATC | TATCCGGGGG | TTAATCACGG | ATTCCATAAT | 4800 |
| GATTCCACGC | CCCGTTATGA | CAAATCTGCC | GCCGATCTTT | CCTGGCAAAG | GACACTGAAA | 4860 |
| TGGTTCGATA | AATATCTCTC | CTGATAGGTT | TATCTCTTAC | GGGATTACGT | CTTAAACAAG | 4920 |
| CATGAAAAAA | TAGCGTGCGC | AAAAGTCGTT | CTTTGCCTAA | AATATCGCTA | TATATAACAA | 4980 |
| TATATAGCGA | ATGAGGTGAA | CGATGAATAA | CCATTTTGGT | AAAGGCTTAA | TGGCGGGATT | 5040 |
| AAAAGCAACG | CATGCCGACA | GTGCGGTTAA | TGTGACAAAA | TACTGTGCCG | ATTATAAACG | 5100 |
| CGGTTTTGTA | TTAGGCTACT | CACACCGGAT | GTACGAAAAG | ACCGGAGATC | GCCAGCTTAG | 5160 |
| CGCCTGGGAA | GCGGGTATTC | TGACGCGCCG | CTATGGACTG | GATAAAGAGA | TGGTAATGGA | 5220 |
| TTTCTTTCGT | GAGAATAATT | CCTGTTCTAC | GTTGCGCTTT | TTTATGGCCG | GTTATCGCCT | 5280 |
| CGAAAATTGA | TCAAACATAC | GTATTATCTT | GCTTTAATTA | ATTACACTAA | TGCTTCTTCC | 5340 |
| CTTCGTTTTA | GCGCCCCGCC | GCAGTATCAT | GATATCGATA | ACCATAATAA | ATGTGTGGTA | 5400 |
| AATGGCGCAT | CGATCGCATT | ATTGATTTTG | CGATTGAGGC | AAAATATATG | CCAGGTCTTC | 5460 |
| GCAACGGAAT | AACTATAAAT | GACTGGAGAT | AACACCCTCA | TCCATTCTCA | CGGCATTAAC | 5520 |
| CGTCGTGATT | TCATGAAGCT | T | | | | 5541 |

( 2 ) INFORMATION FOR SEQ ID NO:21:

( i ) SEQUENCE CHARACTERISTICS:
        ( A ) LENGTH: 6317 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Enterobacter cloacae
        ( B ) STRAIN: Clinical Isolate ET- 12

( x i ) SEQUENCE DESCRIPTION: SEQ ID NO:21:

| | | | | | | |
|---|---|---|---|---|---|---|
| AAGCTTGCCC | GCATCATTCA | GGAGCAGGGG | CGTCGCGACC | AGTTAGGTGT | GAAGTTTGGC | 60 |
| AGCGGTGACA | GCCCGGACTG | CCGGGGGATC | ACGGTTCCGG | AACTGCAGAG | TATCGACTTC | 120 |
| GACAAAATCA | ACTTCTCTGA | CTTCTACGAG | GATTTGATGA | AGAACCAGAA | AATCCCCGAT | 180 |
| ACCAGCGCGC | AGGTCAAGCA | GATTAAGGAT | CGCATCGCCG | CGCAGGTGAA | CCAGCAGGGA | 240 |
| GGTGGCAAAT | GAAGCGTGTC | CTCTGTGGCC | TGCTTATGGC | GCTGGCGAGC | CATACGGCAC | 300 |
| TGGCCGATGA | GATTGTGACG | CCGGCTGAGC | CGTTCACCGG | CTGGTCCTGG | TACAACGAAC | 360 |
| CGAAAAAGCC | CCCTGAGCAG | CCCCGGAAAC | CGCAGCAGCC | AGCACCGCAG | CCATTCCGGA | 420 |
| TCTCAGCAAA | ATGTCCCCGA | TGGAGCAGGC | CAGGGTGCTG | AAAGGGTATA | CACAGGAGGC | 480 |

```
GCTTAACCGC  GCCATCCTGT  ACCCCTCAAG  GGAAAACACG  GCGACGTTCC  TGCGCTGGCA   540
GAAGTTCTGG  ACGGACCGGG  CATCGATGTT  CAGCCAGTCC  TTTGCGGCGG  CGCAGCTGAG   600
CCATCCGGAC  CTCGACTACA  ACCTGGAGTA  TCCGCACTAC  AACAGCATGG  CGCCGTTTAT   660
GCAGACCCGT  GACCAGCAGA  CGCGGCAGAG  CGCCGTGGAG  CAGCTTGCGC  AGAGTACGGT   720
CTGTTCTACT  TCTACCGGGG  CAGTGACCCG  ATTGATGTGC  AGATGGCGGG  CGTGGTGGCT   780
GACTTTGCGA  AAACCAACGG  GATCTCACTC  ATTCCGGTCT  CGGTTGACGG  ACAGGTGGCG   840
GCCACCCTGC  CGCAAAGCCG  TCCGGACACC  GGACAGTCCC  GGTCGATGAA  TATCACGCAC   900
TTTCCGGCGC  TCTTCCTGGT  TGACCCGCGC  AACCAGAACT  ACCGTGCCCT  GTCCTATGGC   960
TTCATGACCC  AGGATGACCT  GTCAAAACGA  TTCCTGAACG  TGGCCACCGG  CTTTAAACCC  1020
AATTCCTGAG  AGCCTTTTAT  GACAAAAACA  CTGTTTACCT  CATCCGCGAT  GCAGGGCGGG  1080
CTGCCCTGTA  TTCCTTCGTC  CTCGGCCCGG  CACTGGTGCT  GTATGTGTTT  GTGATGCTGG  1140
CGGCATCAGA  CGGCTCACTT  TCCCGGCAAT  TCCTGACGAC  CTTTCATCAC  CTGACTGAGG  1200
GTGCGCCTGC  CGGCAAGGTG  ATGGGATGTG  TTAATGAACA  TGAGATGGCA  GGGCGTTTCT  1260
CGCCACCTGA  ACCCGGAGAG  TCGTTAAAGC  CCGTGCCTTC  CGTTTTAGAT  AAAGCACCGC  1320
CTGAAGTGTT  ATGTCAGCTC  GGGCCCGTTG  ACAGCGATTC  GTGGGCGCGT  ACGACAGATG  1380
CAACGTTGCT  CAACACCTGG  ATTATCTCGG  TGATGTTTGG  CTTTGGTGTG  TGGTTTGTTT  1440
TATATGGCCT  GTCCCGGGCC  GCTCAGCGTC  GCATTTCACC  AGACACACAT  TCTGTACTGG  1500
TACGGCAGAA  CAAGGAGACA  CAGGAATGAA  ACCAACTCTT  CTCGCAGGAC  TGATTTTCTG  1560
GGGCATGATG  GCGCGCCGTA  CTGAGCGAGC  TGATGACCTG  GTCCGTGGAG  CATACACAGC  1620
AGGGCCTGCT  GTGGCTGTGC  AATGGGATGT  GGGCCGGGGC  GGCTGGCATG  GTGATTTATG  1680
CAGGTTATCG  CTGGTACCGT  GACGAAAGAG  GGCAAACGCA  TAAGGAAGGC  GATCATGAAC  1740
ATTAAAACCG  GACTCACGGC  TCTGCTGATG  TGCCTGCCCC  TGCTGGCGAA  CGCGGGGGCG  1800
CGCGAGGAGT  TAATGGCGCT  TGAAGCGACA  AAAACAACCT  CTGCTGACGC  TGCAGCCATC  1860
ACCGCCTCCA  CCATTCCGGT  ACCTGCGCCG  GCCAGCCTGA  TGGCGCTGCC  GGACGGACGT  1920
CGGGCTAACA  TGAAAGATTA  TGCCGTGGTG  CTTTTTATGC  AGGCACACTG  CCAGTACAGC  1980
GCGAAGTTTG  ACCCGCTGCT  GAAGGCTGG   GCTGATGAGC  ATTCTGTCAG  GGTTTATCCA  2040
TACACCCTGG  ACGGCGGCGG  TGATGTGTCT  TACCGACGCC  GATGATCCCG  CGCAAGACGG  2100
ACCCGAATTC  TCCCATTGCA  GACGAGATTG  TCACCTTCTT  CGGAAACGGG  CTGCCGATTG  2160
CGACACCAAC  GGCCTTTATG  GTCAACGTTA  ACACCCTGAA  AGCCTACCCG  CTGACCCAGG  2220
GTGTGATGGA  CATCCCCGCT  CTTGAGAGCC  GTATGGCCAG  CCTGATTCAG  GCTGACATGG  2280
ACAACGTCGA  TCCGAAAACG  CTGCCGCCCA  TGCCGGCAAG  TGCGCAGGTC  ACCCCTCAGT  2340
AATACAAACG  GACTACAAAA  TGACGACAAA  TACGTATGCG  TTATCGCGTA  CCGAGCGCGT  2400
GTGGCTGTTA  TTCAGCGTGA  CGCTGCTTGT  GTCCGCAGCT  TTCTATGGGG  TACTGGCCCA  2460
CCGGGTGGTC  AGCGTCTGAC  CGTCAGACTG  ACAACTGTTT  GCAGGACTTT  CCGGTGCTCC  2520
TGCTTATCTC  GCTGAGTATC  GGATTCTTTT  TCACCGTCAC  CGGGCTGTAC  GTCTGCCGGC  2580
AGACCCTGGT  CAGGAAACCC  CGGGAGGAGA  TTGCATGAGG  CACATCAGAC  TGAAGACGTT  2640
TATCCGAAAC  CAGGCTATCG  GGATACTGAA  AGACAGTAGT  GAGGATACGG  AAACCCGAAA  2700
ATGGACGGAT  TTGTTAACCC  TGAAACTGTT  TTTATGCCTT  AATTTTTACC  GCCGTAGTCG  2760
AAAGGGTATA  CGTGAAGTGC  GCCATCACAA  CGCTCAGTGC  GATCTCCGTT  GACCGCTCCG  2820
AACAGTTTAC  GCTCTCGCTT  CTCATCCACT  ATCCACAGTA  CCTGTTGTGG  GGCGTTATGG  2880
```

-continued

```
CCGCGATTAT CGCGCTCATT GCGGTGAATT TACTCGTCTG CGGCTGGTTC TGTCTGGCCA    2940
CATATCTTTG CCGCAAACTG AACCGGACTG ACATCCCGGC AGGCAAGGAT ATGCAAGCTG    3000
TGGAGGTGCC TAATGATTAA GGCGCTTATT ACGGCAGGGG TTGTGTTCTT CTCAGGTCTG    3060
GCAGCGCTGC CTGCTCAGGC GGACGTCAAT GGTGACTCAA CGGCTTCTTT GGCAAGCTGG    3120
GCTACAGCGG CAACGTCTCT CAGGCGCAGG CCTGGCAGGG CAGGCGGCC  GGGTATTTCT    3180
CCGGCGGGTC GGTCTACCTG CGAAACCCCG TCAAAAACGT TCAGCTGATC TCGATGCAGC    3240
TGCCGTCCCT GAACGCCGGC TGCGGCGGTA TCGATGCCTA CCTGGGGTCA TTCAGCATGA    3300
TCAGCGGTGA GGAAATTCAG CGATTCGTGA AGCAAATCAT GAGTAACGCG GCTGGCTATG    3360
CATTCGACCT GGCACTGCAG ACGATGGTCC CGGAGCTGAA GCAGGCGAAA GATTTCCTGC    3420
AGAAGCTGGC CAGTGATGTT AACTCCATGA ACATGAGTTC GTGCCAGGCC GCTCAGGGCA    3480
TCATAGGCGG GTTGTGGCCC GTAACGCAGG TGTCACAGCA GAAAATCTGC CAGGACATTG    3540
CCGGCGAAAC CAACATGTTT GCTGACTGGG CGGCCTCCCG CCAGGGCTGC ACCGTCGGAG    3600
GACAGGGGGA TAAAGTCACG GCCAAAGCCG GCGACGCAGA AAAAGACCC  AGGTACTGAA    3660
AAACAAAAAC CTTATCTGGG ACACGCTCAG TAAGAACGGG CTGCTTGGTA ACGATCGCGC    3720
CCTGAAGGAG CTGGTCATGA GTACTGTCGG CTCCATCATT TTCAACAAAA CCGGAGACGT    3780
GACATCCTGA CGCCGCTGGT CGATACCGCG ACCTGATTAA AGTTCTGATG CGCGGGGAA    3840
CAGCGAAGGT CTACGGGTGC GATGAGGCAA CACTCTGTCT GGGGCCTGTC GTTACTAACC    3900
TGACGATTAC TGAGTCCAAC GCTCTGGTCA CACTGGTCAA AAAACTGATG CTCTCGATGC    3960
AGAACAAACT TGTCGATGAC AAACCGCTGA CCGATCAGGA AAAAGGCTTC GTGAACACCA    4020
CCTCTGTGCC GGTACTGAAA TACCTGACCA ACGCCCAGAG TATGGGGATG AGCGCCACGT    4080
ACCTCCTGCA GGTTTCCGAC TTCATCGCGC AGGACCTGAT GATCCAGTAC CTCCAGGAAC    4140
TGGTGAAACA GGCAAGCCTG TCTCTGGCTG GTAAGAACTT CCCGGAAGAG GCCGCTGCGA    4200
AGTGCGCGAC AACATCATTC ATGCCCAGGG ACTGCTGGCC GACATGAAGC TGCAGTCTGC    4260
GGCAGACCAG AACGCACTGG ACGGCATCGA CCGCAACATG CAGTACTGCA GCAGCAGGTG    4320
TCCACCATTG TTTCAGGCTC CTATCAAAGC AACTATCACT GGGGTGATCG CTGATGCTTG    4380
AGATATACAC CATTTATGGC GGGGGAATGT GGAAAAACGC GCTGGACGCC GTTGTCACCC    4440
TTGTCGGTCA GAATACCTTC CACACCTTAA TGCGTATTCG CCCGGCACCT TCGGGGTGCT    4500
GGCTGTATTG CTCACTTTCA TCAAACAACG TAACCCGATG GTCTTCGTCC AGTGGCTGGC    4560
GATCTTCATG ATCCTGACGA CCATCCTGCT GGTACCGAAA CGTTCAGTAC AGATAATTGA    4620
CCTCTCAGAC CCCGGCTGCG GTGTGGAAAA CCGATAATGT ACCGGTCGGT CTGGCTGCCA    4680
TCGCGTCACT GACGACCAGC ATCGGTTACA AAATGGCATC GGTGTACGAC ATGCTGATGG    4740
CCAGACCTGA CTCGGTAACC TACAGCAAGA CCGGTATGCT GTTTGGCTCG CAGATTGTGG    4800
CGGAAACCAG TGACTTCACC ACGCAAAACC CGGAACTGGC TCAGATGCTG CCGGACTACG    4860
TGGAAAACTG TGTGATCGGC GACATTCTGC TGAACGGTAA ATACACCATC AATCAGCTGC    4920
TCAATTCCAC TGACCCGCTG ACGTTGATAA CCAGTAACCC AAGCCCGCTG CGGGGCATCT    4980
TTAAGATGAC CTCCACCTCG CGCCAGTTCC TGACCTGTCA GCAGGCGGCA ACGGAGATTA    5040
AGACGCTGGC GAATACCGAC GTCAATCCGG GCAGTGCGAC GTTCACCTGG CTGACGCGGA    5100
AGGTATTCGG CAACAAGCTG AATGGTGCCT CGCTTCTGCC AACGCTATGG GTGAGAGCTA    5160
CGGATTCTTC TATGCCGGGG GAATGACGGC TGCGCAGATC ATGAAGAACA ACATCACGAA    5220
CAGTGCAGTT CGGCAGGGGA TTAAGGGTTT CGCCGCTCGC TCATCCGACA CGGCTAACCT    5280
```

|             |            |            |            |            |            |      |
|-------------|------------|------------|------------|------------|------------|------|
| GCTGAACCTG  | GCCACCGAGA | ACGCTGCAAC | CAAACAGCGT | CTCAGCTGGG | CTGCGGGTAA | 5340 |
| TGAGCTTGCC  | ACCCGAACTC | TGCCGTTTGC | ACAGTCCCTG | CTGATGCTTA | TCCTGGTGTG | 5400 |
| CCTGTTCCCG  | TTGATGATTG | CGCTGGCCGC | ATCAAATCAC | ACTATGTTTG | GGCTGAACAC | 5460 |
| CCTGAAAATA  | TACATTTCCG | GTTTTATCTA | TTTCCAGATG | TGGCCGGTGA | TGTTCGCCAT | 5520 |
| CCTTAACTAT  | GCTGCCAACT | ACTGGCTGCA | GAGTCAGTCC | GGGGCACGC  | CTCTGGTGCT | 5580 |
| GGCCAACAAG  | GATGTAGTGG | CACTGCAGCA | TTCGGACGTG | GCGAATCTGG | CAGGGTATCT | 5640 |
| GTCGTTGTCC  | ATTCCGGTGC | TGTCGTTCGT | ATCTGACCAA | GGGGCTGCG  | GCGATGGGCT | 5700 |
| CTCAGGTGGC  | AGGCAGTGTC | CTCAGTTCGG | GCGCCTTCAC | GTCGGCAGGT | GTGGCAGCAA | 5760 |
| CCACGGCGGA  | CGGGAACTGG | TCGTTAACA  | ACATGTCAAT | GGACAATGTC | AGCCAGAACA | 5820 |
| AGCTGGATAC  | CAACCTGATG | CAGCGTCAGG | CCAGCAGACG | TGGCAGGCAG | ATAATGGTTC | 5880 |
| CACGCAGACG  | CAGACGCCGG | TGGCCATACG | GTATCGACGG | CTCAGGCGCA | ATGTCGAATC | 5940 |
| TGCCGGTGAA  | CATGAAGCTC | AGCCAGCTGG | CCAGCAGTGG | TTTCCAGGAG | TCTGCCCGCC | 6000 |
| AGTCGCAGGT  | CCAGGCGCAG | ACGGCGCTCG | ATGGCTACAA | CCACAGTGTC | ACCAGTGGCT | 6060 |
| GGTCGCAGCT  | CTCACAGCTG | TCTCACCAGA | CCGGTACCAG | CGACAGCCTG | ACCAGCGGCA | 6120 |
| GTGAAAACAG  | CCAGGCCACT | AACTCAACGC | GCGGCGCGAG | CATGATGATG | TCGGCCGCTG | 6180 |
| AAAGCTATGC  | GAAAGCTAAC | AATATCTCGA | CGCAGGAAGC | CTATAACAAG | CTGATGGATA | 6240 |
| TCAGTAATCA  | GGGTTCTGTA | TCTGCAGGCA | TTAAAGGTAC | GGCCGGAGGG | GGACTTAATC | 6300 |
| TGGGCGTTGT  | TAAGCTT    |            |            |            |            | 6317 |

(2) INFORMATION FOR SEQ ID NO:22:

(i) SEQUENCE CHARACTERISTICS:
        (A) LENGTH: 6914 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Enterobacter cloacae
        (B) STRAIN: Clinical Isolate ET-49

(xi) SEQUENCE DESCRIPTION: SEQ ID NO:22:

|             |            |            |            |            |            |     |
|-------------|------------|------------|------------|------------|------------|-----|
| AAGCTTTTCG  | AGTTCGCCAT | CCGGCAACAG | CTCACTGAGC | TTTTACGCGC | CCAGGGTGCC | 60  |
| TTTGAACTCA  | ATTCCCAGCT | CAGTAAGGCG | GTCCTGAATA | ATCTCTTTGC | GAGATTTTTC | 120 |
| ACTGGTACCG  | GCATCAGGTG | TTGCAGGTTT | CAGCTCGCCA | CCAGCCTCGC | CCTTCATCAG | 180 |
| CCGGACGTTA  | GACTTCAGCG | CCGGGTGAAG | ATCTTTCAAC | TCCACCACGT | CGCCAACCTT | 240 |
| TACGCCGAAC  | CATGGGCGCA | CAACTTCGTA | TTTAGCCATG | CTGTTTCCTT | ACGCCAGGTT | 300 |
| AGCGCCGTAG  | ACAACGCCAG | ACAGGCCTGA | TCGTCTGCAG | TAATTTGCAG | GCCTTCAGCA | 360 |
| GACATGATCT  | GGAAGTTGTA | GTTAACGTTA | GGCAGTGGGC | GCGGCAGTGG | CACAACGCCA | 420 |
| ACAGCCATAC  | CCACCAGTGG | GGAGATCACG | TCACGACGAC | GAACGTACGC | GATAAACTCG | 480 |
| TTACCGGTCA  | GCGCGAAGTC | ATGCGGATTT | CTTTCACCGG | TGCGAATGGC | AGAACAGCCT | 540 |
| GCAGGAGAGT  | GCCGCTCACC | ACACCATTAA | CTACGTATGG | CTGAGCCATA | TTTGCCCAGA | 600 |
| TCTCAGGGGA  | AACCCACATC | ACATCATACT | GAGCTACTTT | GTTGGTGCGT | GCGGTGGTAC | 660 |
| CGAATGCTCC  | TTTACCAAAG | AACTCAAAAT | ATTGAGTCGT | GGTTGCGCTG | GTCAGGTCGA | 720 |
| TGTTCGCACC  | ACCAGCACCA | GAACCGAGGT | TAATCTTCTT | GGTGTTGCGG | TGGTTCTTGA | 780 |

-continued

| | | | | | |
|---|---|---|---|---|---|
| TGCCCTGCGC | CGGGTAGGAC | TGAACCTGAA | TTTTTGAATC | GCCGTTCAGG | TAGTAGTTGA | 840
| CGCGCTTCTG | GTTGAACTTG | CGCATCTTCG | CCATCTGCGA | ATCCAGAACC | AGATCAATGC | 900
| CTACAGAGTT | AAGGCCAGCA | GCATGACGCC | AGTAACACC | GTAGCCAGCA | GTAACACCG | 960
| GAATCGGGTC | GCCATCGCTC | GCGTAGTCAG | TGTGGTCGAA | GGAGAATGGC | GCCTGACCAT | 1020
| CGATGCTTAC | TGACACGTCG | TCAGCGATGT | CGCCGACCAC | GTTATACAGC | TTGGCGGTTT | 1080
| TACCAACCGG | CAGCACGGTC | TGAACGCCGA | TCAGGTCGTT | TACGATTTCC | ATGCCAACTT | 1140
| CCTGATCCCG | CAGCTGCAGC | ACCTGGTTGT | CAATCTCAGC | CCAGAAGTCA | CGGGAGAAAC | 1200
| CGCCAACAGC | GTTACAAGCC | AGCATGTCAG | GCGTCATCAT | TGCGCGGTTA | GCTGCAATGA | 1260
| TGGAATCGTT | CTGTAGGTTC | CACATGTTGC | GGTTTGCCCA | CAGCTCACTC | CAGTGCCCGC | 1320
| CGAGGCGGGA | GTTAGTCGCC | AGCGTCTCTT | TAGAGAAGTA | CATATGTGTT | TGTCCTTTTG | 1380
| TTACGCGCCA | GCTGCGGCGA | CAGTGCCAAC | GCGCATACGC | ACGCGAATGA | AGTCAGTGGT | 1440
| GCTGGCCGCG | ATGGTGTATT | CATCCTGGCT | GTAGCCGATC | ACTGAATCAG | TGTCGGATGT | 1500
| GGCAAGGGTA | AACTGACCGG | CAGTTCCCAG | CTTGATCGGG | CTGTCTTTTT | TATACGCACC | 1560
| AGGCAGGCAG | CGCAGCGCCA | GCTCACGACC | TTCTTCGACG | TAGTTACCTA | CTGCCGAATC | 1620
| CCCGGCAGGG | ATTTCTTCGG | TGATTGTCAG | GCCCTGGTGA | TAACCGACAT | CGATGATGTA | 1680
| CAGGCGGCCG | GTTAGCGCGG | TGGCCTGAGC | GAATTATCG | GATGAGTTGA | TGGTTGCGGC | 1740
| GGTGCCAGGA | AGCAACCCGG | CGGCCGTTGT | GCGGGTTTCG | GTCTTGTACA | GAGACTGACC | 1800
| GTCGATATTA | ACGCGACGAT | AACGTGGCAT | TATTCCGGCT | CCTTACTTGA | AGTGTTCGTC | 1860
| TGCGGCTGGT | GCGCCGGTTT | CTTTGTGCTG | CTGAGCATTG | TTGGTGCCCA | GCGACTTGAA | 1920
| CATCGCGTCC | AGAGCTTCGC | CTGACAGAGC | GTTCGCGAGC | GATATCGCCA | TGGACCTTCG | 1980
| CAACCGCTTC | GCGCTTTGCT | TTCTCTTCGG | CACGGGAGTT | CGCGGTAAGG | GTTTCCGCGA | 2040
| GTTGCTTCTG | ATTGGCCTGC | AGCGCATCAA | CCTTTTCCGC | GAGAGGCTTA | ATAGCCGCTT | 2100
| CAGTATTGGT | CGCAACAGCC | TGGCCGATCA | TGCTGCCGAT | TTGTTCCAGT | TCTTCTTTGG | 2160
| TTAAAGGCAT | GTCGCCTCCG | TTTTGTGGTT | TGGTGCAGGC | TGTTCCTGCG | GTGTGAATAG | 2220
| AGCTTTGAAT | TGTTAGCGAC | GACTGCCACC | CACGACTCCT | GGCGCGCTAC | TGCGGTTCCG | 2280
| GTATCGTCGA | TTGTGATCTT | CCCGCCATCA | GCGAATACCG | TAAACCTGAG | CATCACCGCC | 2340
| ATTTCGCACG | ATGACCACCT | GCGAGTCAGT | GAGTCAGCAA | CCCAGGCATA | TTCATCCGTG | 2400
| CCCGGCGCAA | ACTTGGCTTT | GGCTGCCCGA | TCGAGACGCT | GCTCGCGCTC | CCGGTAGGAT | 2460
| TCACCCACCA | GCGCGCCGGA | GTTCGCTTTA | AGCGGCTGCG | CCAGATCGGC | GTTTACCATC | 2520
| AGGCCAACGC | CCTGCTCAGG | GGTGGCGGCT | CCGACTTCGT | GCAGTAGGAT | CGCGTCGTGG | 2580
| TCCATGCTGT | GAATCTTCGC | CACCCACTCG | GCACCCGTAG | CTCTCTGTTG | TTCGTTAGGC | 2640
| TCAAGCTGGT | CGAGGAAAGC | GGCGACACTG | GTATGAATCG | GCGGAACGTC | ATCGCCGCGC | 2700
| TCGATGGCTG | CGACGCGCTC | AAGTAGTTCT | CGGCCACCTT | CAGACTCACC | GGCGCGGGCA | 2760
| ACATCAACCC | ACTTTTCGAG | GTAGATACGA | TTACCGGACT | TCTTAACGTT | GCGGTTCCAC | 2820
| GCGCCGATAT | GGCCTGCGTT | AATCCCTCC | GGGGAGAAAG | CAGACACGAA | CTGACCATTA | 2880
| ACCTGAGGGT | GGCCCAGCGG | CGCCAGGGTA | CCTTCCAGCC | CCTTATAGTG | GGCGTCGATT | 2940
| TGCTCTTGCG | TGTACAAGCC | GCCATTCATG | ACGACGTTAG | CTGGAAGTGT | GTAGCTCGGC | 3000
| AGCACCAGGT | GCTCACGCCC | GTTGTATGTT | TCGCGCCGGA | TAGACTGGCT | GTTCACCTTT | 3060
| GTGGTGATGT | TGACCTGAAT | ATGCTCACCA | TGTTTCGGTG | CCTGGATTGG | ACGCTGTGCT | 3120
| TCGTGGTTTA | CCTGGAATTT | CATGAGTTAT | TTCTCCGCCC | AGGCGTAACC | GCTCGCCTGC | 3180

```
ATCGATTTAT ATTCCTGTTT GAGTTTCGTG ATGGTGTCCG GGTATTCCGG CTTGCCGTCC   3240
GCATCCACCA GCACCGACTG CTGGCTGCAT TTGCAGTTGA TGGAGTTGCC ATCTTTGCTG   3300
TACCAGTCAC GCACCTCTTC GTTGGTGTAG AGGTGGGCAT GGGCGCACTG CGTGGGTATG   3360
TCGCGTTGTC GGCGACAGAG CTGAGATGTG AACCAGCAGC GTTTAAGGC CGAACAGGTC    3420
ATTCGCCTCT TGGTCTTCAT CCCACTTGGC CCGGCGCAGC GCGGTAGTCA CTTCAGTGCG   3480
TGCTATCCGG TTAGCCCGGC GTTTCTCGAT GCCGGTCTGG TCTGTCAGGT TGCGGGCAAT   3540
GTCCAGAGGA TTGAGCCCGC GCCCAACACC ATCAGTAAGA CACGCGCCAT GTCGCGCTTA   3600
ACGTCAGCCG TCAGCCCCTT CATTTCCTCA AATACACGCG CATGCACCAG CGCCATGCGT   3660
TTCTGATACT GGTCGCTTGC GAGGATGGAG GCCAGCGACT CACGCCCGGC TGCGTACACC   3720
GGGGATTGCT GACTGAGGTT GTAGAACGAC TGCCCGGTCC CTTTTTCCGA AGCCAGATCG   3780
ATGTACTCGT AAAACCACAG GTCGTAATCG CCACCTTCAA GCAGTACCTG ATCAACCAGG   3840
TAACTGGCAT CGTTCAGGAT GATGGAGAGT AGCATTGGGT TTAGCTGGTA TTCGTATCTG   3900
GCGTTTACTG CGAGGGAGGA AGGTATTTTG TTGAGTGCTG ATTTGTACGC CTTGCCAATC   3960
TTATTCATCC GCCTGGCGAA GTCTTTCATT GCCCGGCGTT CCAGCGCATC GGCTCCGGTC   4020
GGATCCTGAT AGTTACGCGG CAGAATCGGT GGCTTCGTCT TCTTCGTCGC CATCCTCTTC   4080
TCCTAATGGA AATTCATCGA CGTTTTCATA ACCGGCAGCA GTGCGGAATT TCTTCACGAC   4140
TAAAGGCTGG TTTTTCTCCG CTCCCCTGGA ACGTCTGGTT AATCTCTGCC ATGGTTTTGG   4200
CATTTGCGAG TTTCTCAGTT CCAGTCTGTT CGTTGAGGTC ATCCAGATA ACCGTCTTCT    4260
CGCTGACTGC ATCAATAATT TTCAGGTCGA TGAGCTTGTC ACTGAAGTCT TCAATTTCGA   4320
ATGACAGGTC ACCGCGCCGT GACTGGCAGC GCGCGTTGAA ATATTTCTGA TCCTCGGTGC   4380
TTGCCCTTTC ACCCGTCTGC ATCCCAACCA GAACCTTCAC AGGGATATCA ACAGATGCAG   4440
CGAAGGTTTG CAGGTTGACG TTATAGGTCG CTGACGGATC CGCTACAGCT GTGACCAGTG   4500
GTGTGACTGT AGCCCCTTGG GTTGTCATCA GAACATCGTT ACCACGGTTC ATTTCCCCGG   4560
CAACTTCGTT AAACTTATCC TGCAACTCGT CCATGTCACG CCATAAAGTG ACGCGAGATT   4620
GTTGAAATCG ATTTCCTTCT CAAAGTTGAC ATTAAGCTGC CGCGCGGCGT TCTTTAGGAA   4680
TGACTCACCA GAACCACCCT CGACCTTCTC AAGGCTGACG CAGGCGTTAT AGCCAGGCTC   4740
AAGGAAGCCA ATAGCATCAT TAGAATAGTC ACCAAGGATA AAGACGCGAT CGGGATGTAC   4800
GAAGCGCTGA TTAGTTCCAC CGCTTGGAAG GCTCTCAACA TATTTCCACT GCTTTGGCTG   4860
CCCGTAGCCT GCCGATTTCT GGTCAGTTAC CCACTCGCTG ACTGTTAATG ACCCAGCCCA   4920
TGCGATCGTA ACCTTTTTTA GTGACTTGCC ACGAACAACA GGCTGATCCC ATGTTCTGGA   4980
ATCATTGATA TGCAGCAGGA TACCCGCATA ACGTCCGACC TGTCGGCGGC GGTCTGCTTC   5040
AGCAAAAGCC CGCCAAAGGC GCTTTGTGAA AACCTTTTTG GTGTTCTTCT CCCAGGCAGT   5100
TTCATCCTTA CTCTCGTCGG CATCATCACC CTCGATGATT TCCGGGTTGG TCTGCCAGCA   5160
CTTGCCCACC AGCTTCTCTA CTGCGCCGTG GGCTATTCCA CCGCGACGAT ACAGTGCGTA   5220
GAGGTTTTCG TAAGTGACCT GCTCAGGGAA TCCATACTCG CACCATGCGG AATGGCGCTT   5280
ATTGTCCAGC CCCATTGTAG GCGCCAACAG CCCCATACGG GCACGGGCCA TCCGCGCATC   5340
GTTCAACGCA TGGTTGACGG CGAGAGTTAA TTTGTCAGTC ATGGTTTGTC CGTTGGTGGA   5400
TTTAAGGCAT AAAAAAAGGC CGCTTTGGCG ACCTTGTGGC TATTTAAAAA GCTAAACTCT   5460
GTTGAACGAA ATAAACATAA TCTGCTCAGG CTTAACGCCA TAATCACTTG CCAACTTCTG   5520
AGTGCACTCA ATTAAGACAG TTGATGCAGA TTTCGAAGAG CTTGCACCAT AAATTTCGAA   5580
```

```
GTTTTCAAAT   ACTCCGCCGT   TGGTGTGGTA   AATCTTATAT   GACATAAACC   AATCATTCAT      5640
AATATCTACT   CCCTTACAGA   ATTGAGTAGA   TATTATCGGC   AAGTGCATAT   GTTTCTTTAA      5700
ATTATCTCAA   CCTTTTCGGG   ATCATCATCC   CGGCCATCTG   GCCCTTACGT   TTAATGTGTC      5760
CGTCGAGGCT   GTAGCGAATA   CCGTCCCAGC   AGTGTTCGTA   ACCGTCTGCC   AGTTTAGGCA      5820
ATACCTCGCC   GGTGATGCGG   TCCGTTTTGT   AGGACCACAT   GCGGGCCTCT   CTCGCCACAT      5880
TCTTGCAGCG   AGGATGGATA   ATGATTTCGT   CAAAGCCGCG   AAGATGCGCG   ATACCGTCCT      5940
CAACACTCCC   CTGCCATTTC   TCGGCAGCCG   AGATGTTGAA   GCCCTGGCGC   TTGAGATAGC      6000
TGATAGTCTC   GGGTCGGGCG   GAGTCGGCCT   TGATGGGCCA   GTCACGCGAT   CCGGGGATTG      6060
TGTCGTATAG   CTCTGGCATA   TGGTCGAGCT   CTGTCTGCTG   ACCGTATGCC   TCGTATTCGA      6120
TGTACAGCCG   GTTGTGCAGG   ATGAACGAGC   GCACCAGCGT   GTTAGGGTCT   TTGGCGAAAC      6180
CGAAGTCAGC   ACCGAAGAAA   AGGCGATCGG   CCTCTTTCCA   TAGCTGGTCC   GAGAACTCAG      6240
CGATCCGGTA   TTTACCGGCC   AGCACCTGCT   TATCAGAGTT   TTCGAGGTAA   GCACCTTCCC      6300
AAACCCACGC   GTATGTTGCC   GGGTCAAGGC   GGCGCTGATC   GTTCTGTCGC   TCACCTTCCA      6360
GCACGTCGGG   GAACCATGGA   TTATCCGTGT   AGTTCATCTC   AACGTGATAC   AGTCGTCGCC      6420
AGCCTCTTTA   CGGAAACGCT   TATCCGTGCG   CTGCCGTCGC   GCTCCGGGTT   CCATGTCACC      6480
CAAATCTCTG   AACCTTCCTC   ACGAACGGTC   GGGCTCAGCT   TCTGCCAGGC   TATTTCGCTG      6540
ACTGATTCAG   CCTCATCAAC   CCAACAGAGC   AAGATGCGCG   CTTTCGACTT   GATGCTGTCG      6600
AGGTTATGCC   GCAGACCGCA   GAACACGTAG   TTAACGCTCT   TGTCGATGGT   GCGGATGTAC      6660
TTCTCGCCGA   TATCAAAGTT   GGAAGCCAGC   CAGGGAACAG   ACAGGATAGC   CTGTTTCACC      6720
TCCTGCATAC   TCGACTCTTC   CAGTGAGTTC   ATGAATTCAC   GCGCACAGAG   CACCACGCCG      6780
CTTTCACCGT   TCATCATCGA   CTGATACGCC   TTTACGGCTG   TCATCAGCGC   AAAAGTGCGC      6840
GTCTTGGCAC   TACCACGCCC   ACCATGCGAG   CACCGGTAAC   GCTTATTCTC   GGCGATGAAC      6900
AGTGGCGCAA   GCTT                                                              6914
```

( 2 ) INFORMATION FOR SEQ ID NO:23:

( i ) SEQUENCE CHARACTERISTICS:
        ( A ) LENGTH: 5975 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Klebsiella pneumoniae
        ( B ) STRAIN: Clinical Isolate KI- 50

( x i ) SEQUENCE DESCRIPTION: SEQ ID NO:23:

```
AAGCTTATTC   CACGCTGGAG   GCGTCCGGGA   TTATCGGCGT   CAACGCTATC   GCCGGCATCG       60
CCGGGACCAT   CATCGCCGGC   ATGCTCTCCG   ACCGCTTTTT   CAAACGCAAC   CGCAGCGTGA      120
TGGCCGGATT   CATCAGCCTG   CTGAACACCG   CCGGCTTCGC   CCTGATGCTC   TGGTCGCCGC      180
ACAATTACTA   CACTGATATT   CTGGCGATGA   TTATCTTCGG   GGCCACCATT   GGCGCTCTGA      240
CCTGCTTCCT   TGGCGGGCTG   ATCGCCGTCG   ATATCTCTTC   GCGCAAGGCC   GCCGGGGCCG      300
CGCTCGGCAC   CATCGGCATC   GCAGCTACGC   CGGCGCCGGC   CTGGGCGAGT   TTCTCACCGG      360
GTTCATTATT   GATAAAACGG   CTATCCTTGA   AAACGGCAAA   ACGCTGTATG   ATTTCAGCAC      420
GTTGGCGCTG   TTCTGGGTGG   GTACGGTCTG   GGTTCNGCGC   TACTCTGTTT   TACCACTGCC      480
GCCATCGTCG   CCCGGCGCCA   TGCCGTCGAA   CGGCAGACCT   CGTTCTCCTC   ATAACCGATT      540
```

| | | | | | | |
|---|---|---|---|---|---|---|
| AACGAATAAG | GAAGAAGATA | TGATGCCTGC | AAGACATCAG | GGGCTGTTAC | GCCTGTTTAT | 600 |
| CGCCTGCGCG | CTGCCGCTGC | TGGCGCTGCA | ATCTGCCGCC | GCCGCGGACT | GGCAGCTGGA | 660 |
| GAAAGTGGTC | GAGCTCAGCC | GCCACGGTAT | TCGTCCGCCG | ACGGCCGGCA | ACCGGGAAGC | 720 |
| CATCGAGGCC | GCCACCGGCC | GACCGTGGAC | CGAGTGGACC | ACCCATGACG | GGGAGCTCAC | 780 |
| CGGCCATGGC | TATGCCGCCG | TGGTCAACAA | AGGGCGTGCG | GAAGGCCAGC | ATTACCGCCA | 840 |
| GCTCGGCCTG | CTGCAGGCCG | GATGCCCGAC | GGCGGAGTCG | ATATACGTGC | GCGCCAGCCC | 900 |
| GCTGCAGCGG | ACGCGAGCGA | CCGCCCAGGC | GCTGGTGGAT | GGCGCCTTCC | CCGGCTGCGG | 960 |
| CGTCGCTATC | CATTATGTCA | GCGGGGATGC | CGATCCCCTG | TTTCAGACCG | ACAAGTTCGC | 1020 |
| CGCCACGCAA | ACCGACCCCG | CCCGCCAGCT | GGCGCGGTGA | AAGAGAAGGC | CGGGGATCTG | 1080 |
| GCGCAGGTCG | GCAGGCGCTG | GCGCCGACCA | TCCAGCTATT | GAAACAGGCG | GTTTGTCAGG | 1140 |
| CCGATAAGCC | CTGCCCGATC | TTCGATACCC | CGTGGCAGGT | CGAGCAGAGC | AAAAGTGGGA | 1200 |
| AGACCACCAT | TAGCGGACTG | AGCGTGATGG | CCAATATGGT | GGAGACGCTG | CGTCTCGGCT | 1260 |
| GGAGTGAAAA | CCTGCCTCTC | AGCCAGCTGG | CGTGGGGCAA | GATCACCCAG | GCCAGGCAGA | 1320 |
| TCACCGCCCT | GCTGCCGCTG | TTAACGGAAA | ACTACGATCT | GAGTAACGAT | GTGTTGTATA | 1380 |
| CCGCGCAAAA | ACGCGGGTCG | GTGCTGCTCA | ACGCTATGCT | CGACGGCGTC | AAACCGGAGC | 1440 |
| GAATCGAACG | TACGCTGGCT | GCTGCTGGTG | GCCATGACAC | CAATATCGCC | ATGGTGCGCA | 1500 |
| CGCTGATGAA | CTTTAGCTGG | CAGCTGCCGG | GCTACAGCCG | GGGAAATATC | CCGCCGGGCA | 1560 |
| GCAGCCTGGT | GCTGGAGCGC | TGGCGCAACG | CGAAGAGCGG | AGAACGCTAT | CTGCGGGTCT | 1620 |
| ATTTCCAGGC | CCAGGGCCTC | GACGACCTGC | GTCGTCTGCA | GACGCCGGAC | GCGCAGACCC | 1680 |
| CGATGCTGCG | TCAGGAGTGG | CATCAGCCGG | GCTGCCGTCA | GACCGATGTC | GGTACGCTGT | 1740 |
| GTCCCTTCCA | GGCGGCTATT | ACCGCCCTCG | GTCAGCGTAT | CGACCGATCA | TCCGCCCCGG | 1800 |
| CGGTAGCATG | GTCCTGCCGT | AGCGGCGCGG | TGTTTGTCCG | GGCCCGGGAA | AACCTTTTTT | 1860 |
| TCCAGGCCGG | CACGACGTCC | GTTATCCGTT | GTCCGGCGCA | AACGCCCCGG | CGGCGACCTG | 1920 |
| CGCCGGGGTG | ACACCCGCTG | TCCAGCACCC | AGCCGCTTAT | CAGCCCAGCA | GGCGTGACGT | 1980 |
| CGAACGCCGG | ATTGTAAACG | GTGGCCCCCG | TCGGCGCCCA | CTGTACCGCG | CCGAAGCTGC | 2040 |
| CCGCCACTCC | GGTCACTTCC | GCCGCCGCGC | GCTGCTCAAT | GGGGATCGCC | GCCCGTTCG | 2100 |
| GGCAATGGCG | GTCGAGGGTG | GTCTGCGGGG | CAGCGACGTA | AAACGGGATC | TGGTGATAAT | 2160 |
| GGGCCAAAAC | CGCCAGAGAA | TAGGTGCCGA | TTTTATTCGC | CACGTCGCCG | TTGGCGGCGA | 2220 |
| TACGGTCGGC | GCCGACCCAC | ACCGCATCCA | CCTGCCCCTG | CGCCATCAGG | CTGGCGGCCA | 2280 |
| TTGAATCGGC | GATCAGCTGA | TAGGGCACGC | CCAGCTCGCC | CAGCTCCCAG | GCGGTTAAAC | 2340 |
| GACCGCCCTG | CAGCAGCGGC | CGGGTTTCAT | CAACCCATAC | GTTGGTCACT | TTTCCCTGCC | 2400 |
| GGTGCGCCAG | CGCGATAACG | CCGAGGGCGG | TCCCTACCCC | GGCGGTCGCC | AGGCCACCGG | 2460 |
| TGTTGCAGTG | GGTCAGCAGT | CGACTGCCGG | GCTTCACCAG | CGCACTGCCC | GCCTCAGCGA | 2520 |
| TGCGGTCGCA | CAGCTGTTTA | TCTTCTTCGA | CCAGACGCAA | GGCTTCCGCT | TCCAGCGCCT | 2580 |
| GCGGGTAATC | TCCGGGCCAG | CGCTGCTTCA | TGCGATCAGA | TTATTCATCA | GGTTGACCGC | 2640 |
| CGTCGGCCGC | GCCGCGCGCA | GTCTCCAGCG | CCTGCTGGAG | TGCATCCCGG | TTCAGGCCGC | 2700 |
| GCTGGGCCAG | CAGGGCCAGC | AGCAGGCTGG | CGGACAGGCC | AATCAGCGGC | GCGCCGCGCA | 2760 |
| CCCCGCAGGT | ATGAATATGG | TCCACCAGCA | GCGCAACGTT | ATCCGCCGCC | AGCCAGCGTT | 2820 |
| TTTCCTGCGG | CAAGGCCTGC | TGGTCGAGAA | TAAAAAGCTG | ATTTTCACTC | ACCCGCAGGC | 2880 |
| TGGTGGTCTG | TAATGTCTGC | ATGTCGTTAA | ATCCCTGTTG | CGTTGTTGTA | TCACATTGTG | 2940 |

```
TCAGGATGGA ATCCAGAAGT ATAGACGTCT GAACGGCTTA ATCAGAATTC GAGGATCGAG     3000
GCAATGTCGC AATACCATAC CTTCACCGCC CACGATGCCG TGGCTTACGC GCAGAGTTTC     3060
GCCGGCATCG ACANCCATCT GAGCTGGTCA GCGCGCAGGA AGTGGGCGAT GGCAACTCAA     3120
TCTGGTGTTT AAAGTGTTCG ATCGCCAGGG CGTCACGGGC GATCGTCAAA CAGGCTCTGC     3180
CCTACGTGCG CTGCGTCGGC GAATCCTGGC CGCTGACCCT CGACCGCGCC CGTCTCGAAG     3240
CGCAGACCCT GGTCGCCCAC TATCAGCACA GCCCGCAGCA CACGGTAAAA ATCCATCACT     3300
TTGATCCCGA GCTGGCGGTG ATGGTGATGG AAGATCTTTC CGACCACCGC ATCTTGCGCG     3360
GAGAGCTTAT CGCTAACGTC TACTATCCCC AGGCGGCCCG CCAGCTTGGC GACTATCTGG     3420
CGCAGGTGCT GTTTCACACC AGCGATTTCT ACCTCCATCC CCACGAGAAA AAGGCGCAGG     3480
TGGCGCAGTT TATTAACCCG GCGATGTGCG AGATCACCGA GGATCTGTTC TTTAACGACC     3540
CGTATCAGAT CCACGAGCGC AATAACTACC CGGCGGAGCT GGGAGGCCGA TGTCGCCGCC     3600
CTGCGCGACG ACGCTCAGCT TAAGCTGGCG GTGGCGGCGC TGAAGCACCG TTTCTTTGCC     3660
CATGCGGAAG CGCTGCTGCA CGGCGATATC CACAGCGGGT CGATCTTCGT TGCCGAAGGC     3720
AGCCTGAAGG CCATCGACGC CGAGTTCGGC TACTTCGGCC CCATTGGCTT CGATATCGGC     3780
ACCGCCATCG GCAACCTGCT GCTTAACTAC TGCGGCCTGC CGGGCCAGCT CGGCATTCGC     3840
GATGCCGCCG CCGCGCGCGA GCAGCGGCTG AACGACATCC ACCAGCTGTG GACCACCTTT     3900
GCCGAGCGCT TCCAGGCGCT GGCGGCGGAG AAAACCCGCG ACGCGGCGCT GGCTTACCCC     3960
GGCTATGCCT CCGCCTTTCT GAAAAAGGTG TGGGCGGACG CGGTCGGCTT CTGCGGCAGC     4020
GAACTGATCC GCCGCAGCGT CGGACTGTCG CACGTCGCGG ATATCGACAC TATCCAGGAC     4080
GACGCCATGC GTCATGAGTG CCTGCGCCAC GCCATTACCC TGGGCAGAGC GCTGATCGTG     4140
CTGGCCGAGC GTATCGACAG CGTCGACGAG CTGCTGGCGN GGGTACGCCA GTACAGCTGA     4200
GTGCGCCTGT TTCCCTCACC CCAACCCTCT CCCACAGGGA GAGGGAGCAC CCCCTAAAAA     4260
AGTGCCATTT TCTGGGATTG CCCGGCGNGN TGCGCTTGCC GGGCCTACAG ATAGCCGCAT     4320
AACGGTTTGA TCTTGCACTC TTTCGTAGGC CGGGTAAGGC GAAAGCCGCC ACCCGGCAGA     4380
CATGCGAGTA CAATTTTGCA TTTACCTTAC CCTCACCCCA GATACTCAAT CACCGATAGC     4440
CCGCCGTTGT AATCGGTGCT GTAGATAATG CCTTGCGCAT CGACAAACAC GTCACAGGAC     4500
TGGATCACCC GCGGGCGGCC GGGACGGGTA TCCATCATTC TCTCAGCGCA GCCGGCACCA     4560
GCGCCCCGGT CTCCAGCGGG CGATACGGGT TGGAAATGTC GTAAGCCCGC ACGCCGGCAT     4620
TCTGATACGT GGCAAAAATC AGCGTTGAGC TGACAAAGCT CCCCGGCCGG TTCTCATGCA     4680
GGTTGTGCGG ACCGAAATGC GCCCCTTTCG CCACGTAATC CGCTTCATCC GGCGGCGGGA     4740
AGGTGGCGAT GCTCACCGGG TTGGTTGGCT CGCGGATATC AAACAGCCAG ATCAGCTTCT     4800
CGCCGTCCTC CTGGTTATCG AGCACCGCTT CATCCAGCAC CACCAGCAGA TCGCGATCCG     4860
GCAGCGGCAG CGCGGTATGC GTTCCGCCGC CGAACGGCGG GCTCCAGTTG CGATGGCTAA     4920
TCAGCCTCGG CTGGGTACGG TCTTTGACAT CCAGCAGCGT CAGGCCGCCG TCGCGCCAGC     4980
TGCGTAGGCG TATCCCCGGC AATAATGGCG TGATGCAGCG CATAGCGTTT GCCCTGCGGC     5040
CAGTCCGGTG TTTCACCGCC CGCCTGGTGC ATCCCGGCA GCCACCAGCG CCCGGCTACT     5100
TCGGGCTTAC GCGGATCGGC CAGATCGATG GTCAGGAAGA TGTAGTCGGT AAAACCGTCG     5160
ATCAGCGCAG ACACATACGC CCAGCGCCCG CCGACGTACC AGATGCGGTG AATACCGATG     5220
CCGTTAAGCG ACAGGAAACT GATTTCCCGC GCTGCGCGGG AGTGGAAATA TCAAAGATGC     5280
GCAGCCCGGC GCTCCAGCCC CTGTCCTGCA CATCGCTGAC CGTGTCACCC ACCGAGCGGG     5340
```

-continued

```
TGTAGTACAC  CTTCTCATCA  GCAAAACGGG  CGTCAGCAAA  CAGATCCCGG  GCGTTGATCA      5400

CCAGCAGCAG  ATCGTCATGC  GCCTGGAGTG  CACGTTCCAG  GTGCCCGGCG  GCGCGGCAAT      5460

ATAGTTGACG  GTGGTGGGCC  GGGTCGGATC  GCGAACATCG  ACCACGGAAA  AACCCTGCGA      5520

CACCATATGG  CCGATATAGG  CGAATCCGCG  GTGCACCATC  AGCTGCACGC  CGTCCGGACG      5580

ACCGCCCTGA  TCGCTATGGC  CAATCAGCCG  CATATTGCGG  CTGTATTCGG  GGGAAGGTAA      5640

TGCTGACATA  GGGGATCCCT  CTCGCCCGGT  GGCATGGTTT  TCCCCCCTCT  CCTGCGGAGA      5700

GGGCCGGGGC  GAGGGCACCA  GGCCGCCGCC  CACCGCCACC  CGGCTTGATT  TTATTTGTTC      5760

TTCGCTTCCA  GCGTCGCGAA  CCACGGCGCG  ATAAAGTCTT  CGGTCTGGCC  CCAGCCAGGG      5820

ATAATTTTCC  CCAGCGACGC  CACGTTTACC  GCTCCCGGCT  GGGCCGCCAG  CAGCGCCTGG      5880

GGAATCGCTG  CCGCCTTGAA  GTCGTAGGTG  GCTGGCGTCG  GCTCGCCGGC  GATCTTGTTG      5940

GCGATCAGCC  GCACGTTGGT  CGCGCCGATA  AGCTT                                   5975
```

( 2 ) INFORMATION FOR SEQ ID NO:24:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "primer"

( x i ) SEQUENCE DESCRIPTION: SEQ ID NO:24:

```
CGACGTTGTA  AAACGACGGC  CAGT                                                  24
```

( 2 ) INFORMATION FOR SEQ ID NO:25:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "primer"

( x i ) SEQUENCE DESCRIPTION: SEQ ID NO:25:

```
CAGGAAACAG  CTATGAC                                                            17
```